US012221600B2

(12) United States Patent
Afshar et al.

(10) Patent No.: US 12,221,600 B2
(45) Date of Patent: Feb. 11, 2025

(54) SYSTEMS AND METHODS FOR AUTOMATED CELL CULTURING

(71) Applicant: MYTOS BIO LIMITED, London (GB)

(72) Inventors: Ali Afshar, London (GB); James Cunningham, London (GB); Henry Miskin, Stroud (GB); Ignacio Willats, London (GB)

(73) Assignee: MYTOS BIO LIMITED, London (GB)

( * ) Notice: Subject to any disclaimer, the term of this patent is extended or adjusted under 35 U.S.C. 154(b) by 621 days.

(21) Appl. No.: 17/238,644

(22) Filed: Apr. 23, 2021

(65) Prior Publication Data

US 2021/0238532 A1 Aug. 5, 2021

Related U.S. Application Data

(62) Division of application No. 16/543,369, filed on Aug. 16, 2019, now Pat. No. 10,988,726.

(60) Provisional application No. 62/719,652, filed on Aug. 19, 2018.

(51) Int. Cl.
*C12M 1/34* (2006.01)
*G01N 35/00* (2006.01)
*G01N 35/10* (2006.01)

(52) U.S. Cl.
CPC ....... *C12M 41/32* (2013.01); *G01N 35/00584* (2013.01); *G01N 35/1002* (2013.01); *G01N 2035/00673* (2013.01)

(58) Field of Classification Search
CPC ............. C12M 41/32; G01N 35/00584; G01N 35/1002; G01N 2035/00673
See application file for complete search history.

(56) References Cited

U.S. PATENT DOCUMENTS

| 4,146,364 A | 3/1979 | McCormick |
| 6,399,375 B2 | 6/2002 | Vajta |
| 8,383,395 B2 | 2/2013 | Hata et al. |

(Continued)

FOREIGN PATENT DOCUMENTS

| AU | 2011218747 A1 | 9/2011 |
| CN | 107083328 A | 8/2017 |

(Continued)

OTHER PUBLICATIONS

Office Action for JP Application No. 2021-505715, mailed Jun. 2, 2023 (with English translation).

(Continued)

*Primary Examiner* — William H. Beisner
*Assistant Examiner* — Danielle B Henkel
(74) *Attorney, Agent, or Firm* — Ambrose, Mills & Lazarow, PLLC

(57) ABSTRACT

Systems and methods for automated cell culturing are disclosed. In some embodiments, one or more cell culture vessels are fluidly connected with one or more multiport valves and one or more fluid pumps. The fluid pumps may pump various fluids into and out of the cell culture vessels as necessary to support cell growth, routed by the one or more multiport valves. In some embodiments, one or more components may be removable from other components so that some components may be prepared and sterilized independently prior to usage.

14 Claims, 67 Drawing Sheets

(56) References Cited

U.S. PATENT DOCUMENTS

| | | |
|---|---|---|
| 8,445,261 B2 | 5/2013 | Greenberger et al. |
| 8,445,266 B2 | 5/2013 | Kiyota et al. |
| 8,785,173 B2 | 7/2014 | Thompson et al. |
| 8,808,643 B1 | 8/2014 | Benner et al. |
| 9,695,393 B2 | 7/2017 | Nankervis et al. |
| 9,783,768 B2 | 10/2017 | Larcher et al. |
| 9,983,222 B2 | 5/2018 | Peltier |
| 10,119,970 B2 | 11/2018 | Miltenyi et al. |
| 10,858,621 B2 | 12/2020 | Kawarai et al. |
| 10,988,726 B2 | 4/2021 | Afshar et al. |
| 11,579,063 B2 | 2/2023 | Ikehata et al. |
| 2005/0051723 A1 | 3/2005 | Neagle et al. |
| 2005/0095705 A1 | 5/2005 | Kadan et al. |
| 2006/0275888 A1 | 12/2006 | Hibino et al. |
| 2008/0248552 A1 | 10/2008 | Castillo Fernandez |
| 2011/0207209 A1* | 8/2011 | Hammons .............. C12M 23/42 |
| | | 435/303.1 |
| 2011/0287534 A1 | 11/2011 | Rowley et al. |
| 2013/0038727 A1 | 2/2013 | Clark |
| 2013/0203106 A1* | 8/2013 | Shvets .................. C12M 41/40 |
| | | 435/375 |
| 2016/0017271 A1 | 1/2016 | Nozaki et al. |
| 2016/0152936 A1 | 6/2016 | Bargh et al. |
| 2016/0178490 A1 | 6/2016 | Civel et al. |
| 2017/0037357 A1 | 2/2017 | Cattaruzzi et al. |
| 2017/0145373 A1 | 5/2017 | Lianides et al. |
| 2017/0204359 A1 | 7/2017 | Ando et al. |
| 2017/0342365 A1 | 11/2017 | Nozaki et al. |
| 2018/0127695 A1 | 5/2018 | Nam et al. |
| 2018/0171296 A1 | 6/2018 | Murthy et al. |
| 2018/0179483 A1 | 6/2018 | Amino et al. |
| 2018/0251723 A1 | 9/2018 | Murthy et al. |
| 2020/0056140 A1 | 2/2020 | Afshar et al. |
| 2023/0087656 A1 | 3/2023 | Afshar et al. |

FOREIGN PATENT DOCUMENTS

| | | |
|---|---|---|
| CN | 107287119 A | 10/2017 |
| DE | 102011054363 A1 | 4/2013 |
| EP | 1944359 A1 | 7/2008 |
| JP | H04179471 | 6/1992 |
| JP | 2018-050550 | 4/2018 |
| WO | WO2006/122089 A2 | 11/2006 |
| WO | WO2018/005521 A2 | 1/2018 |
| WO | WO2019/155032 A1 | 8/2019 |
| WO | WO2020/038874 | 2/2020 |
| WO | WO2021/165397 | 8/2021 |

OTHER PUBLICATIONS

Corning, Life Sciences, "Corning® Reusable Gas and Media Handling Fitting with Dual Inlets (1 long, 1 short tube) for Angled Sidearm Flasks," [online] [retrieved on Aug. 15, 2019] Retrieved from the Internet <URL: https://ecatalog.corning.com/life-sciences/b2c/US/en/Cell-Culture/Cell-Culture-Vessels/Flasks%2C-Culture/Corning%C2%AE-Reusable-Gas-and-Media-Handling-Fitting-with-Dual-Inlets-%281-long%2C-1-short-tube%29-for-Angled-Sidearm-Flasks/p/gasOrMediaHandlingFittingsAngledSidearmFlasksCombinationStyle> (undated), 1 page.

THERMOFISHER Scientific, "Cell Culture Flasks/Tissue Culture Flasks," [online] [retrieved on Aug. 15, 2019] Retrieved from the Internet <URL: https://www.thermofisher.com/US/en/home/life-science/cell-culture/cell-culture-plastics/cell-culture-flasks.html> (undated), 4 pages.

Office Action for U.S. Appl. No. 16/543,369, mailed Jun. 16, 2020.

Final Office Action for U.S. Appl. No. 16/543,369, mailed Jan. 7, 2021.

International Application No. PCT/EP2019/072115, Invitation to Pay Additional Fees and, Where Applicable, Protest Fee, mailed Nov. 28, 2019.

International Application No. PCT/EP2019/072115, International Search Report and Written Opinion mailed Jan. 23, 2020.

International Application No. PCT/EP2021/054027, Invitation to Pay Additional Fees and, Where Applicable, Protest Fee mailed Jun. 1, 2021.

International Application No. PCT/EP2021/054027, International Search Report and Written Opinion mailed Jul. 29, 2021.

Final Office Action for JP Application No. 2021-505715, mailed Dec. 1, 2023 (with English translation).

Office Action for CN Application No. 201980054549.X, mailed Dec. 9, 2023 (with English translation).

* cited by examiner

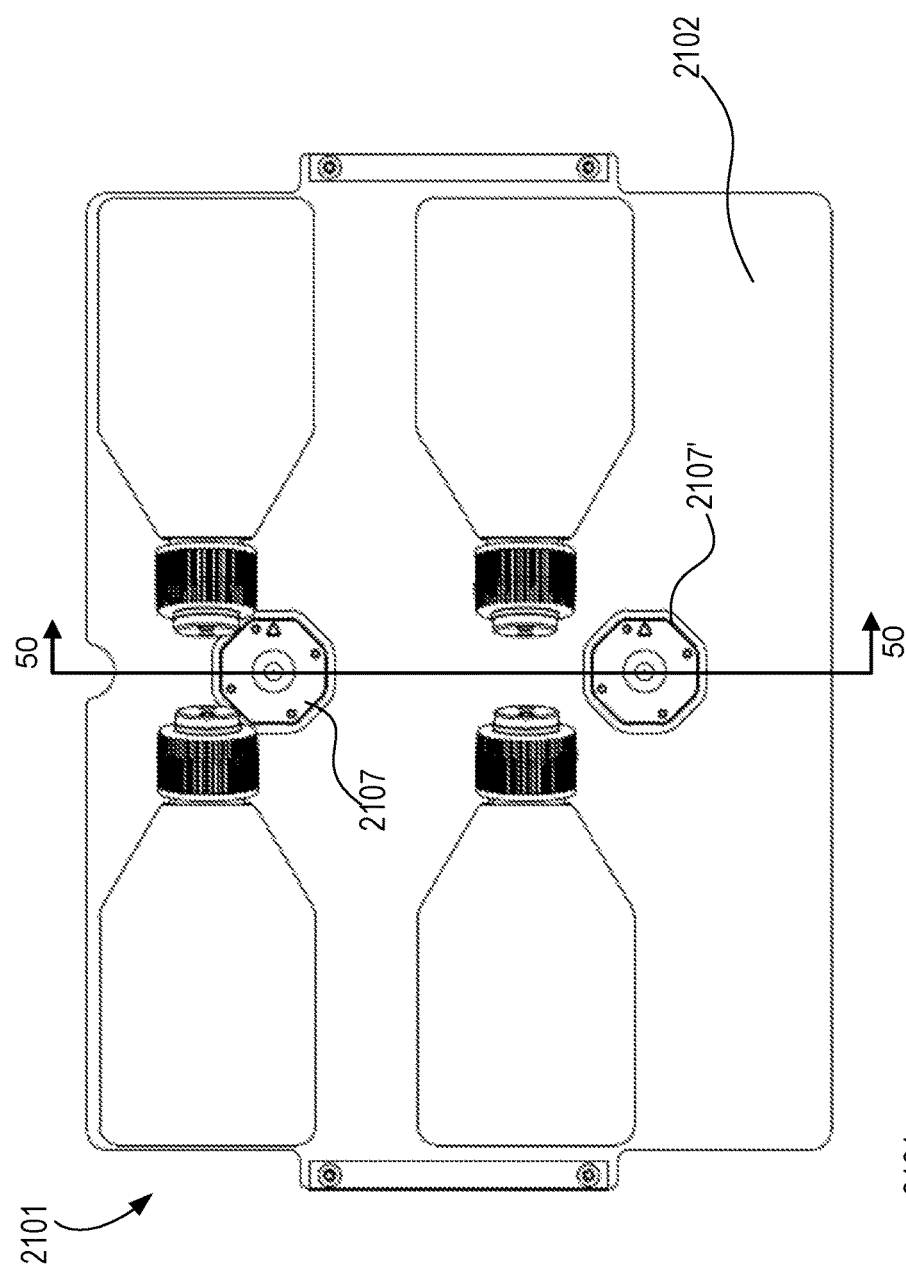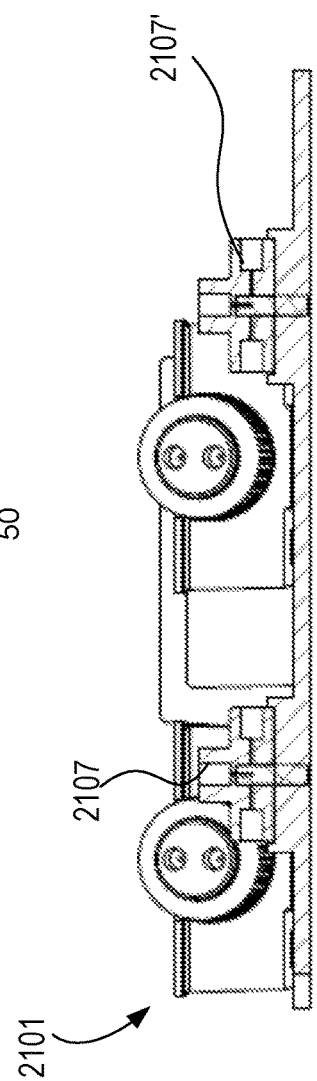

| Vessel | Type | Volume | Location |
|---|---|---|---|
| Fresh media (F) | GL45 | 250ml | Fridge |
| Fresh holding | Falcon | 50ml | Incubator |
| Pump holding | Falcon | 50ml | Incubator |
| PBS | Falcon | 50ml | Incubator/Room temp location |
| Trypsin | Falcon | 15ml | Incubator/Room temp location |
| Harvest | Falcon | 50ml | Incubator |
| Waste | GL45 | 250ml | Room temp location |

FIG. 60

TABLE 2

Cell passaging example (maintenance of adherent culture)

| Purpose of step | Source | Destination | Fluid | Flask 1 state after step | Flask 2 state after step |
|---|---|---|---|---|---|
| | | | | Spent media + attached cells | Empty |
| Remove spent media | Flask 1 | Waste | Spent media | Attached cells | Empty |
| Wash off old media | PBS | Flask 1 | PBS | PBS + attached cells | Empty |
| Remove PBS | Flask 1 | Waste | PBS | Attached cells | Empty |
| Add enzyme | Trypsin | Flask 1 | Trypsin solution | Trypsin solution + attached cells | Empty |
| Incubation time for enzyme | N/A | N/A | N/A | Trypsin solution + detached cells | Empty |
| Quench enzyme | Fresh holding | Flask 1 | Fresh media | Trypsin + fresh media + detached cells solution | Empty |
| Reduce total number of cells by pumping some to waste | Flask 1 | Waste | Trypsin + fresh media + detached cells solution | Trypsin + fresh media + detached cells solution | Empty |
| Move cells to new flask | Flask 1 | Flask 2 | Trypsin + fresh media + detached cells solution | Empty and not usable | Trypsin + fresh media + detached cells solution |

FIG. 61A

TABLE 2 - CONTINUED

| Top up fresh holding with media from fridge | Fresh | Fresh holding | Fresh media | Empty and not usable | Trypsin + fresh media + detached cells solution |
|---|---|---|---|---|---|
| Incubation time for media in fresh holding to warm up | N/A | N/A | N/A | Empty and not usable | Trypsin + fresh media + detached cells solution |
| Incubation time for cells to attach | N/A | N/A | N/A | Empty and not usable | Trypsin + fresh media solution + attached cells |
| Remove remaining trypsin | Flask 2 | Waste | Trypsin + media solution | Empty and not usable | Attached cells |
| Add fresh media | Fresh holding | Flask 2 | Fresh media | Empty and not usable | Fresh media + attached cells |

FIG. 61B

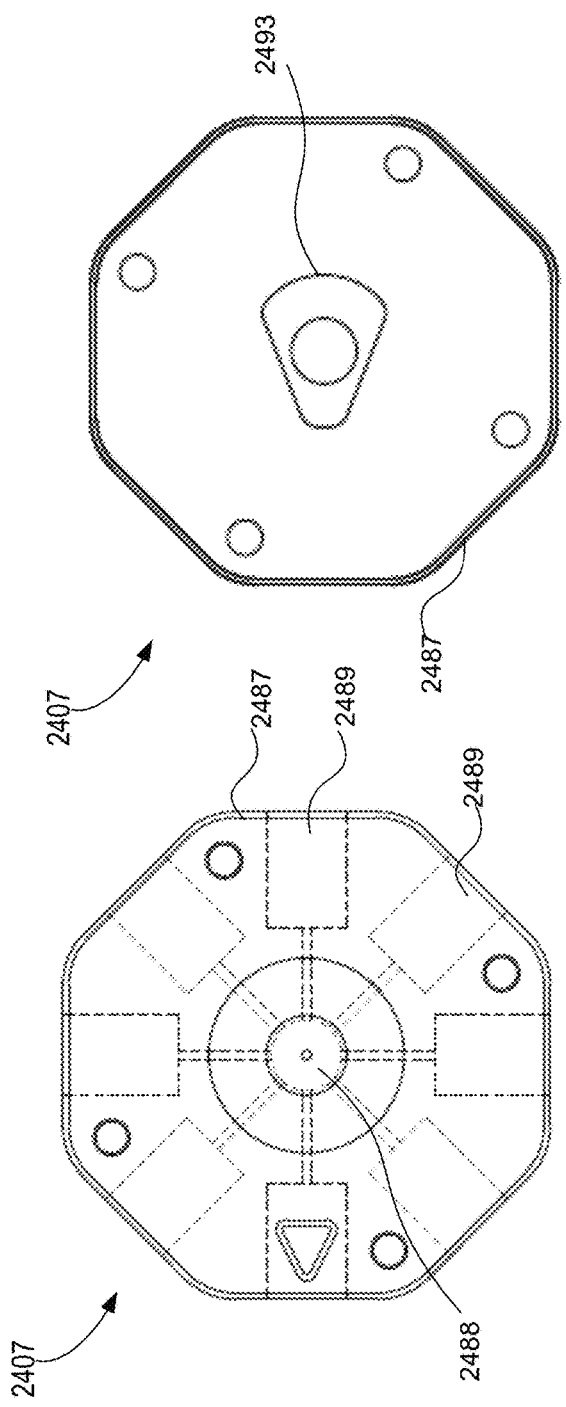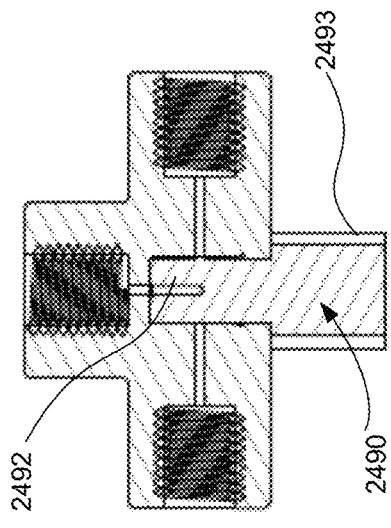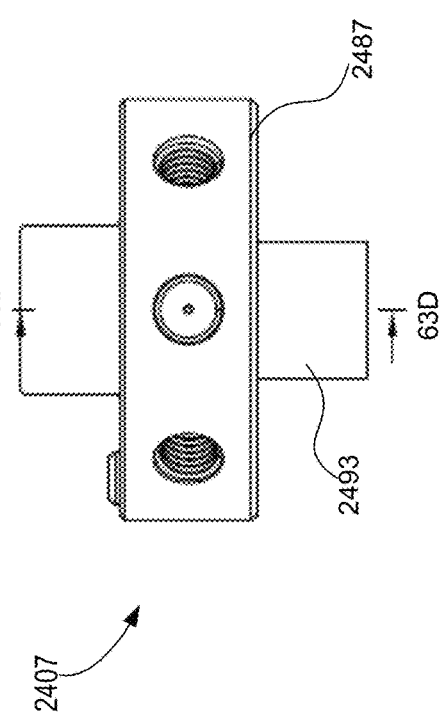
FIG. 63A
FIG. 63B
FIG. 63C
FIG. 63D

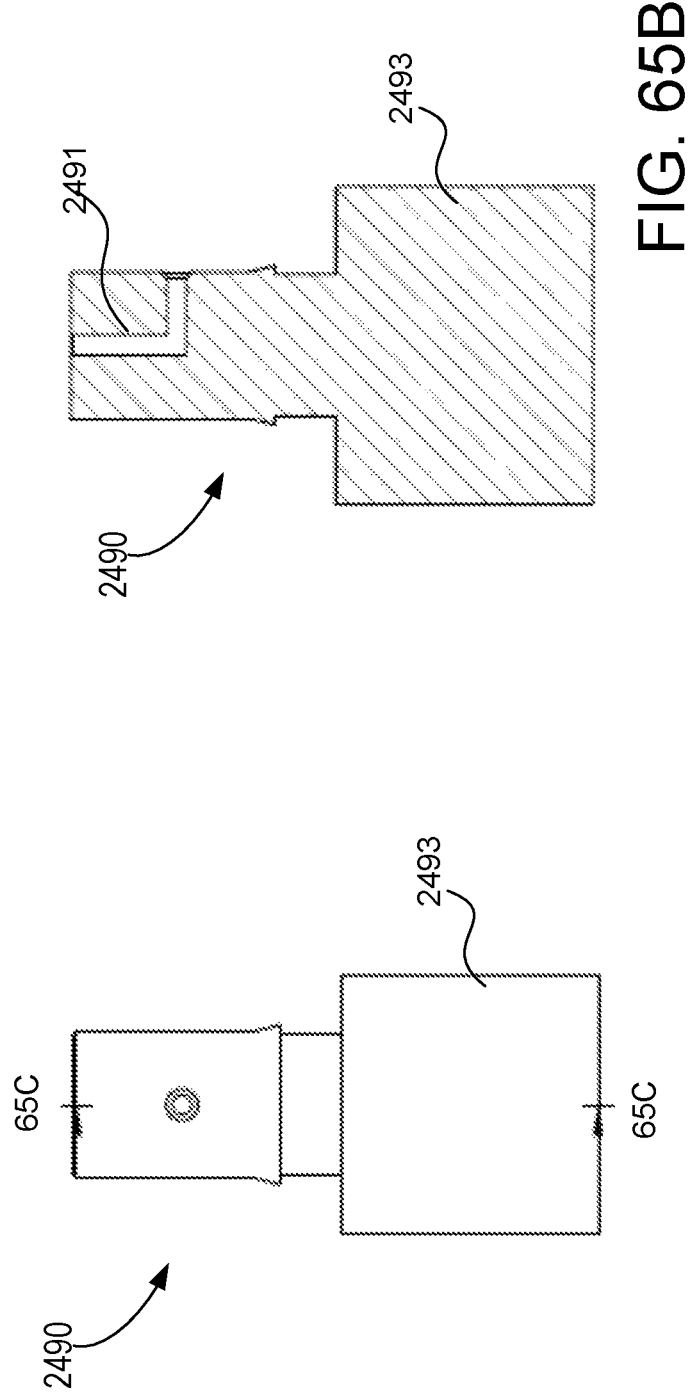
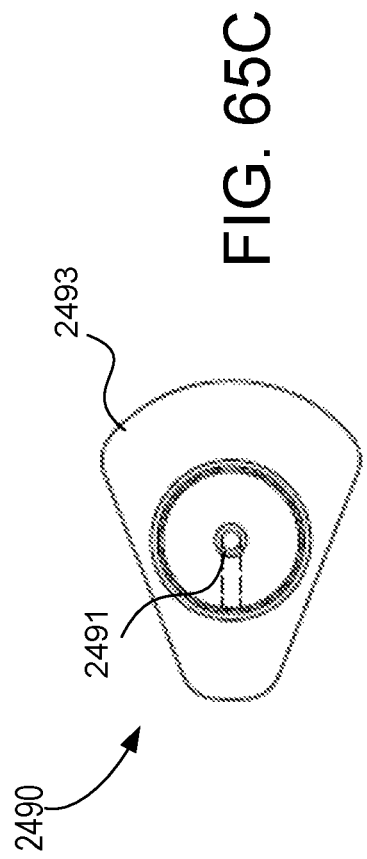
FIG. 65B
FIG. 65C
FIG. 65A

SYSTEMS AND METHODS FOR AUTOMATED CELL CULTURING

CROSS-REFERENCE TO RELATED APPLICATIONS

This application is a divisional of U.S. application Ser. No. 16/543,369, entitled "Systems and Methods for Automated Cell Culturing," filed Aug. 16, 2019 (now U.S. Pat. No. 10,988,726), which claims benefit of priority to U.S. Provisional Application No. 62/719,652 entitled "Automated Cell Culture," filed Aug. 19, 2018, each of which is incorporated herein by reference in its entirety.

FIELD OF INVENTION

This specification generally relates to systems and methods for culturing cells.

BACKGROUND

Cells may be grown, or cultured, under controlled conditions in a laboratory or industrial setting for various purposes. Typically, cells are grown in an enclosed vessel and covered with a solution referred to as a cell culture medium that provides essential nutrients and other supplements to help the cells grow. Examples of vessels used in cell culture include flat circular dishes such as Petri dishes or laboratory flasks. As cells grow and multiply they consume the nutrients in the cell culture medium and produce waste byproducts. For this reason, the cell culture medium must be periodically changed so that the cells continue to flourish. In addition, cell cultures may be expanded by transferring a portion of a cells to new vessels, providing additional volume or area within which the cells can grow. This process of transferring a portion of cells to new vessels may be referred to as passaging or subculturing. Additionally, cells can be removed from the vessel in preparation for their use. The process of separating cells from the vessel they are grown in may be referred to as harvesting.

Cell cultures usually proliferate following a standard growth pattern. The first phase of growth after the culture is seeded is the lag phase, which is a period of slow growth when the cells are adapting to the culture environment. The lag phase is followed by the logarithmic phase in which cells proliferate exponentially and consume nutrients in the growth medium. As a cell culture reaches the capacity of the environment by either consuming all the nutrients in the growth medium or occupying all of the space available, growth slows, and cells enter a stationary or plateau phase in which the proliferation is greatly reduced or ceases entirely. Known cell culture procedures often include passaging the cells prior to entering this stationary phase to optimize growth.

Adherent cells grow attached to a surface, such as the bottom of a culture flask or dish. The amount of cells in the flask is normally measured as the percentage of the growth surface covered by cells, referred to as percentage confluency. Adherent cells have to be detached from the surface before they can be removed from a vessel. Cells may be detached by one of several methods, including mechanically scraping or using enzymes such as trypsin to cleave adhesion to the vessel surface. The detached cells are then resuspended in fresh growth medium and allowed to settle back onto a growth surface.

These processes of removing spent medium from cell culture vessels, adding fresh medium, detaching adherent cells, and transferring cells from one vessel to another are typically carried out by laborious manual procedures. For example, known cell culturing methods often include repeated operations that involve moving the cells (within the cell culture vessels) between various work stations and/or opening the cell culture vessels to move fluids into and out of the vessels. Specifically, known methods include first loading the cells and cell culture medium into the vessels in an aseptic environment (e.g., a laminar flow hood). After being prepared, the cell culture vessels are closed (to minimize contamination) and moved to an incubator to facilitate growth. The cell culture containers are often manually monitored to determine the appropriate time to change the cell culture medium, as well as periodically manually monitoring to inspect parameters such as, for example, confluence and cell morphology, by removing the vessels from the incubator and imaging under a microscope. These manual monitoring steps usually require travelling to the lab just to check on the cultures and determine whether other operations need to be performed. When it is time to change the cell culture medium, the cell culture vessels are then moved from the incubator to an aseptic environment, opened (or otherwise connected to a source of waste and fresh cell culture medium), and the fluids are transferred to and/or from the cell culture vessels. The vessels are also moved and/or opened to complete other operations, such as cell passaging or cell harvesting.

Such known procedures are inefficient, costly, and susceptible to contamination. For example, repeatedly opening the cell culture system and moving the cell culture vessels between lab stations potentially exposes the cells to contamination. Additionally, every operation that is manually performed is expensive and also susceptible to contamination (or cell damage) due to the operator not following proper procedures. Further, determining when to change medium or when to passage cells is typically done according to a predetermined schedule, which may not be optimal. Adhering to set schedules can result in additional (and potentially unnecessary) use of a laminar flow hood (the operation of which can consume large amounts of energy and can therefore be costly). Adhering to set schedules can also result in reduced efficiency for cell growth (e.g., if the cell growth reaches the plateau phase before the cell culture medium is exchanged).

Thus, a need exists for cell culturing systems that improve the efficiency and limit potential contamination during cell culturing. Specifically, a need exists for systems and methods for automating the cell culture procedures, for maintaining the cell culture system in a closed aseptic environment during the culturing, and for allowing efficient set-up and use. A need also exists for an automated cell culturing system that can optionally operate with existing off-the-shelf cell culturing vessels.

SUMMARY

According to one implementation, this specification describes systems and methods for automatically culturing cells. Automated cell culture systems disclosed herein enable scientists to accelerate their research and development by automating manual cell culture. Systems and methods disclosed in various embodiments may provide for automated cell growth media replenishment, automated passaging of cells, and/or automated cell culture analysis. These automated cell culture systems and methods may increase efficiency and decrease error compared to manual cell culture operations. Furthermore, these embodiments increase the quantity and quality of data points on cell culture available to scientists via integrated automated analysis mechanisms.

An automated cell culture system according to an embodiment includes a housing with a valve actuator and a fluid pump disposed within the housing. The automated cell culture system also includes a removable tray configured to removably mate to the housing. A plurality of cell culture vessel brackets attached to the removable tray are configured to hold a respective plurality of cell culture vessels, where each cell culture vessel is capped with an aseptic lid. A selector valve is configured to couple to the valve actuator of the housing when the removable tray is mated with the housing. A plurality of media sources may be provided that are, in some embodiments, external to the housing and removable tray. The multiport selector valve is configured to fluidly connect a master port to a selected one of a plurality of selectable ports, where the master port of the multiport selector valve is fluidly connected to the fluid pump, and each of the plurality of cell culture vessels and media sources are directly fluidly connected to a respective one of the plurality of selectable ports of the multiport selector valve. In some embodiments, the plurality of cell culture vessels and their aseptic lids, the multiport selector valve, and the fluid connections therebetween form a first aseptically sealed system attached to the removable tray:

In some embodiments, a method of cell line maintenance using an automated cell culture system includes transmitting a command to a movable imaging system of an automated cell culture system to image the cells within a selected vessel of the automated cell culture system: receiving from the imaging system an image of the cells within the selected vessel; based on the image of the cells within the selected vessel, measuring a cell passaging criterion; comparing the cell passaging criterion to a threshold cell passaging criterion: based on the comparing, determining to initiate passaging of the cells within the selected vessel to a subculture vessel. The method of cell line maintenance also includes passaging a configured portion of the cells of the selected vessel to the subculture vessel: and transmitting a notification that the automated cell culture system has passaged the configured portion of cells of the selected vessel to the subculture vessel. Other embodiments of this aspect include corresponding computer systems, apparatus, and computer programs recorded on one or more computer storage devices, each configured to perform the actions of the methods.

The details of one or more implementations of the subject matter described in this specification are set forth in the accompanying drawings and the description below: Other potential features, aspects, and advantages of the subject matter will become apparent from the description, the drawings, and the claims.

BRIEF DESCRIPTION OF THE DRAWINGS

The present disclosure will become more fully understood from the detailed description and the accompanying drawings, wherein:

FIGS. 18-20 are each an example screenshot showing various GUI elements produced in connection with operation of the electronic control system.

FIG. 49 is a top view of the tray assembly of FIG. 48.

FIG. 50 is a cross-sectional view taken along line 50-50 in FIG. 49.

FIG. 60 is a table illustrating the contents shown in FIG. 59.

FIGS. 61A-61B include a table illustrating an example of a cell passaging procedure.

FIG. 63A is a top view of a multiport valve, according to an embodiment; and FIG. 63B is a bottom view of the multiport valve of FIG. 63A.

FIG. 63C is a side view of the multiport valve of FIG. 63A and FIG. 63D is a cross-sectional view taken along line 64D-64D in FIG. 63C.

FIG. 65A is a side view of a valve rotor of the multiport valve of FIG. 63A: FIG. 65B is a cross-sectional view taken along line 65B-65B in FIG. 65A: and FIG. 65C is a top view of the valve rotor.

DETAILED DESCRIPTION

Figure 1A:
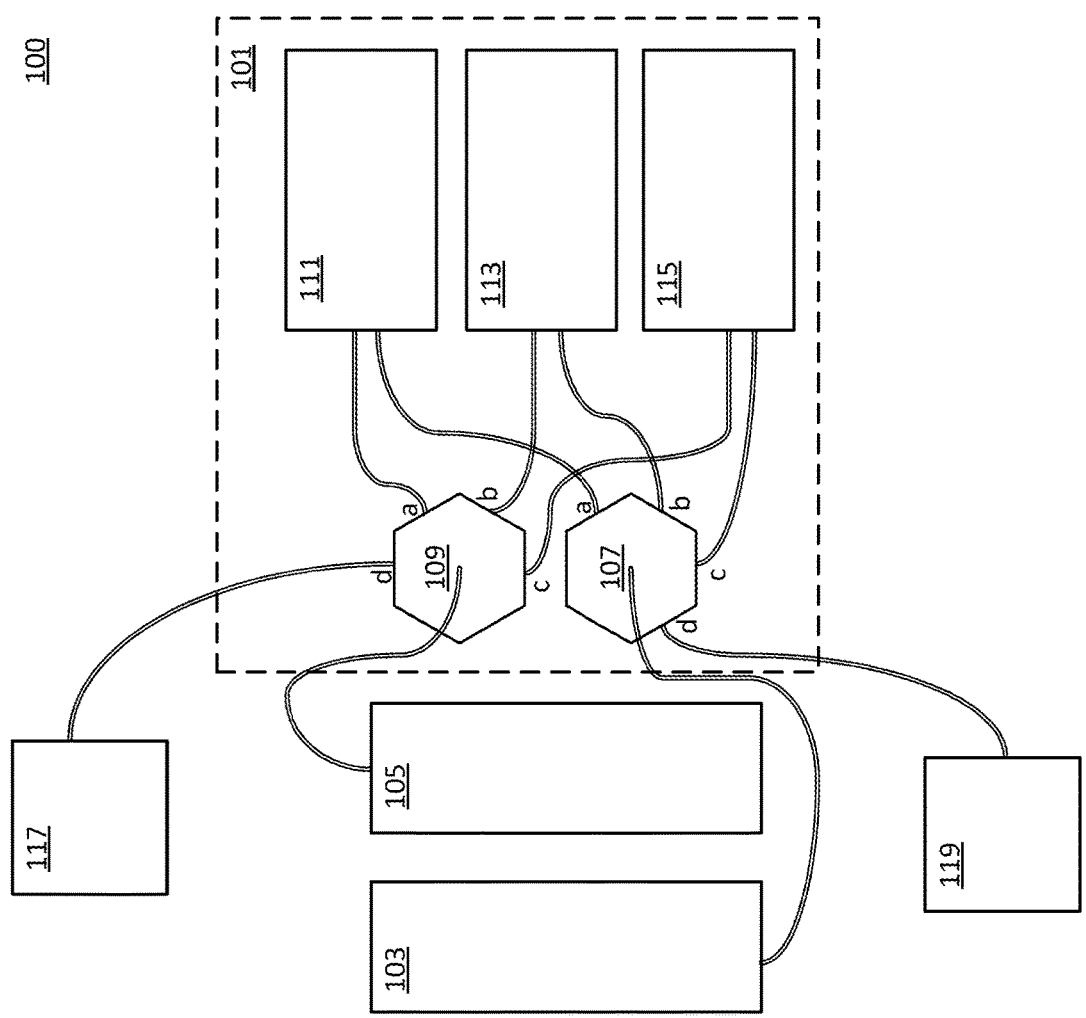
FIG. 1A illustrates a schematic view of an automated cell culture system according to an embodiment.

In some embodiments, an apparatus includes a tray, a first lid, a second lid, and a multiport valve. The tray is configured to be removably coupled to a housing of a base unit. The tray has a first coupler configured to couple a first container to the tray and a second coupler configured to couple a second container to the tray. The first lid is configured to be coupled to the first container and includes a first liquid exchange port and a first gas exchange port. The second lid is configured to be coupled to the second container and includes a second liquid exchange port and a second gas exchange port. The multiport valve coupled to the tray and including a master port and a set of selectable ports. The multiport valve is configured to engage a valve actuator of the base unit and be coupled to a fluid pump coupled to the base unit. A first selectable port of the set of selectable ports is aseptically coupled to the first liquid exchange port of the first lid. A second selectable port of the set of selectable ports aseptically coupled to the second liquid exchange port of the second lid.

In some embodiments, the first coupler maintains the first container in a fixed position on the tray and the second coupler maintains the second container in a fixed position on the tray during operation of the apparatus. In some embodiments, the first container is a cell culture container configured to receive a cell sample and the second container is one of a waste container, a reagent container, or a cell harvest container. In some embodiments, the first coupler is configured to removably couple the cell culture container to the tray. In some embodiments, the cell culture container and the tray each include a transparent portion. The first coupler is configured to couple the cell culture container to the tray such that the transparent portion of the cell culture container is aligned with the transparent portion of the tray.

In some embodiments, the multiport valve and the fluid pump are configured to transfer fluid between the first container and the second container in a closed, aseptic system. In some embodiments, the multiport valve is removably coupled to the tray and is also configured to be removably coupled to a valve actuator of the base unit. In some embodiments, the pump includes a pump actuator and a pump body defining a pumping chamber. The pump body is configured to be coupled to the master port of the multiport valve.

In some embodiments, the tray is configured to engage an agitator coupled to the base unit. The agitator is configured to agitate the tray when actuated.

In some embodiments, the apparatus includes a counting chip coupled to the tray and coupled to a third selectable port of the multiport valve. The counting chip is configured to receive a portion of a cell sample mixture from the first container at periodic time intervals.

In some embodiments, the tray, the first lid, the second lid, and the multiport valve are enclosed within a wrap. In some embodiments, the tray, the first lid, the second lid, and the multiport valve are sterilized within the wrap.

In some embodiments, a base unit of a cell culturing system includes a housing, a pump actuator, and a valve actuator. The housing defines (or includes) a receiving portion configured to removably receive a cell culture tray assembly. The cell culture tray assembly includes a tray; a first lid coupled to the tray that can be removably coupled to a first container, and a second lid coupled to the tray that can be removably coupled to a second container. The first lid and the second lid each include a liquid exchange port and a gas exchange port. The cell culture tray also includes a multiport valve coupled to the tray and including a master port and a set of selectable ports. The pump actuator is coupled to the housing and configured to be operatively coupled to a fluid pump coupled to the master port of the multiport valve. The valve actuator is coupled to the housing and is configured to be coupled to the multiport valve when the cell culture tray assembly is coupled to the receiving portion of the housing. The valve actuator and the pump actuator are collectively configured to selectively move a fluid into and out of the first container coupled to the first lid and into and out of the second container coupled to the second lid.

In some embodiments, the multiport valve is configured to be removed from the tray and coupled to the valve actuator while a first port of the multiport valve is aseptically coupled to the first lid and a second port of the multiport valve is aseptically coupled to the second lid. In some embodiments, the valve actuator includes a keyed drive member configured to matingly engage the multiport valve.

In some embodiments, the fluid pump is aseptically coupled to the master port of the multiport valve via a length of tubing. In some embodiments, the fluid pump is any one of a piston pump, a peristaltic pump, or a vane pump.

In some embodiments, the base unit further includes an agitator coupled to the housing and configured to engage the cell culture tray assembly when the cell culture assembly is coupled to the housing. The agitator is configured to agitate the cell culture tray assembly when actuated. In some embodiments, the receiving portion of the housing includes a support plate coupled to the agitator. The support plate includes a surface to which the cell culture tray assembly can be removably coupled.

In some embodiments, the base unit further includes (or is coupled to) an electronic (or computer) control system configured to control movement of the fluid into and out of the first container coupled to the first lid and into and out of the second container coupled to the second lid. In some embodiments, the base unit includes a sensor movably coupled to the housing and configured to produce a cell signal associated with a quantity of cells within the first container. In some embodiments, sensor is an imaging device coupled to the housing and configured to image the contents within the first container such that at least one of a confluence or a density of the cells within the first container can be determined. In some embodiments, the sensor is configured to monitor a color of the contents of the first container. The first container can contain a color-based pH indicator such that a pH of the contents of the first container can be determined.

In some embodiments, a base unit of a cell culturing system includes a housing, a pump actuator, a valve actuator, and an electronic control system. The housing defines a receiving portion configured to removably receive a cell culture tray assembly. The cell culture tray assembly includes a tray; a first lid coupled to the tray that can be removably coupled to a first container, and a second lid coupled to the tray that can be removably coupled to a second container. The cell culture tray also includes a multiport valve coupled to the tray and including a master port and a set of selectable ports. The pump actuator is coupled to the housing and configured to be operatively coupled to a fluid pump. The valve actuator is coupled to the housing and is configured to be coupled to the multiport valve when the cell culture tray assembly is coupled to the receiving portion of the housing. The valve actuator and the pump actuator are collectively configured to selectively move a fluid into and out of the first container coupled to the first lid and into and out of the second container coupled to the second lid. The electronic control system includes a cell sensor, a cell sensor module, and an actuator module. The cell sensor is configured to produce an output associated with the contents within the first container. The cell sensor module is implemented in at least one of a memory or a processing device of the electronic control system and produces a cell signal associated with a quantity of cells within the first container based on the output of the cell sensor. The actuator module is implemented in at least one of the memory or the processing device and receives the cell signal and produces, based on the cell signal, at least one of a valve control signal or a pump signal to cause movement of cells out of the first container.

In some embodiments, the actuator module is configured to control movement of a first volume of fluid out of the first container and into a waste container, and movement of a second volume of fluid out of a reagent container and into the first container. In some embodiments, the actuator module is configured to control movement of a volume of an enzyme into the first container to facilitate cell dissociation of adherent cells within the first container.

In some embodiments, the apparatus includes an agitator coupled to the housing and configured to engage the tray assembly when the tray assembly is coupled to the receiving portion. The agitator is configured to agitate the tray assembly. The actuator module of the electronic control system is configured to control the actuation of the agitator (e.g., when to agitate and the time period of the agitation).

In some embodiments, the cell sensor is movably coupled to the housing. The sensor module is configured to control movement of the cell sensor relative to the housing such that the cell sensor can be aligned with the first container.

In some embodiments, the base unit includes a valve sensor configured to produce a valve position signal associated with a rotation position of the valve actuator. The valve position signal indicates a selection of one of the selectable ports of the multiport valve. The actuator module is configured to produce the valve control signal based in part on the valve position signal. In some embodiments, the base unit includes a pump sensor configured to produce a pump signal associated with a position of the pump actuator during operation. The actuator module is configured to produce the pump control signal based in part on the pump signal.

In some embodiments, the electronic control system further includes a radio configured to electronically communicate with a computing device. The radio is configured to send to the computing device a wireless signal associated with a measurement associated with a quantity of cells within the first container.

In some embodiments, a base unit of a cell culturing system includes a housing, a pump actuator, a valve actuator, and an electronic control system. The housing defines a receiving portion configured to removably receive a cell culture tray assembly. The cell culture tray assembly includes a tray, a first cell culture container, a second cell culture container, a reagent container, a waste container, and a multiport valve. The multiport valve includes a master port and a set of selectable ports. A first selectable port is coupled to the first cell culture container, a second selectable port is coupled to the second cell culture container, a third selectable port is coupled to the reagent container, and a fourth selectable port is coupled to the waste container. The pump actuator is coupled to the housing and configured to be operatively coupled to a fluid pump coupled to the master port of the multiport valve. The valve actuator is coupled to the housing and is configured to be coupled to the multiport valve. The electronic control system is operably coupled to the valve actuator and the pump actuator. The electronic control system includes an actuator module implemented in at least one of a memory or a processing device, and that is configured to produce a series of valve control signals and pump control signals. Specifically, the actuator module can produce a first valve control signal to cause the valve actuator to actuate the multiport valve and a first pump control signal to cause the pump actuator to actuate the fluid pump to move a cell culture media from the first cell culture container to the waste container. The actuator module can produce a second valve control signal to cause the valve actuator to actuate the multiport valve and a second pump control signal to cause the pump actuator to actuate the fluid pump to move a reagent from the reagent container to the first cell culture container. The actuator module can produce a third valve control signal to cause the valve actuator to actuate the multiport valve and a third pump control signal to cause the pump actuator to actuate the fluid pump to move a plurality of cells from the first cell culture container to the second cell culture container.

In some embodiments, the electronic control system includes a cell sensor module implemented in at least one of the memory or the processing device. The cell sensor module receives an output from a cell sensor and produces a cell signal indicating a dissociation of cells within the first cell culture container. The actuator module is configured to produce at least one of the third valve control signal or the third pump control signal in response to the cell signal. In some embodiments, the cell sensor is microscope and the output from the microscope is an image. The cell sensor module is configured to produce the cell signal indicating the dissociation of cells based on the image. In some embodiments, the cell sensor module is configured to produce an alignment signal to move the cell sensor into alignment with the first cell culture container.

In some embodiments, the base unit includes an agitator coupled to the housing and configured to engage the tray assembly. The agitator is configured to agitate the tray assembly. The actuator module of the electronic control system is configured to produce an agitator signal to cause agitation of the tray assembly.

In some embodiments, a computer-implemented method includes receiving at an electronic control system of a cell culture assembly, a sensor output from a sensor of the cell culture assembly. The cell culture assembly includes a disposable cell culture tray assembly couplable to a reusable base unit. The cell culture tray assembly includes a tray, a first lid coupled to a first container, a second lid coupled to a second container, and a multiport valve coupled to the tray: The multiport valve includes a plurality of selectable ports and a master port coupled to a fluid pump. At least one of the first container or the second container contains a plurality of cells. A cell signal associated with a quantity of the plurality of cells within one of the first container and the second container is produced based on the sensor output. Based on the cell signal, at least one of a valve control signal to actuate the multiport valve or a pump control signal actuate the fluid pump is produced at the electronic control system to initiate flow of fluid out of at least one of the first container or the second container.

In some embodiments, the sensor is a part of an optical measurement assembly configured to move the sensor, and the method further includes sending a position signal to the optical measurement assembly to move the sensor into a measurement position relative to at least one of the first container or the second container. In some embodiments, the cell sensor is microscope and the sensor output from the microscope is an image. The electronic control system can produce the cell signal indicating a dissociation of cells within the first container or the second container based on the image.

In some embodiments, the base unit includes an agitator operably coupled to the tray of the tray assembly. The method optionally includes sending from the electronic control system to the agitator an agitator signal to actuate agitation of the tray assembly to maintain cells within at least one of the first container or the second container in suspension. In some embodiments, the method includes sending, after the sending an agitator signal, at least one of an actuator signal or a pump signal to cause flow of a fluid mixture out of one of the first container and the second container and into a counting chip fluidically coupled to the one of the first container and the second container.

In some embodiments, a computer-implemented method can control fluid movement within a cell culture assembly that includes a disposable cell culture tray assembly coupled to a reusable base unit. The method includes producing, via an actuator module of an electronic control system of the cell culture assembly, a first valve control signal and a first pump control signal. The first valve control signal causes a valve actuator of the base unit to actuate a multiport valve to fluidically couple a first selectable port of the multiport valve to a master port of the multiport valve. The master port is fluidically coupled to a fluid pump and each selectable port is fluidically coupled to one of a first cell culture container, a second cell culture container, a reagent container, or a waste container. The first pump control signal causes a pump actuator of the base unit to actuate the fluid pump to move a cell culture media from the first cell culture container to the waste container. A second valve control signal is produced causing the valve actuator to actuate the multiport valve to fluidically couple a second selectable port to the master port and a second pump control signal causing the pump actuator to actuate the fluid pump to move a reagent from the reagent container to the first cell culture container. A third valve control signal is produced causing the valve actuator to actuate the multiport valve to fluidically couple a third selectable port to the master port and a third pump control signal causing the pump actuator to actuate the fluid pump to move a plurality of cells from the first cell culture container to the second cell culture container.

In some embodiments, the method includes producing, via the actuator module, a fourth valve control signal causing the valve actuator to actuate the multiport valve to fluidically couple a fourth selectable port to the master port and a fourth pump control signal causing the pump actuator to actuate the fluid pump to move a wash media from a wash container into any one of the multiport valve, a holding volume, or a tube coupled to the multiport valve, or a cell culture vessel.

In some embodiments, the base unit includes a cell sensor and the method includes receiving an output from the cell sensor. A cell signal is produced indicating a dissociation of cells within the first cell culture container. The actuator module produces at least one of the third valve control signal or the third pump control signal in response to the cell signal. In some embodiments, the method includes producing an alignment signal to move the cell sensor into alignment with the first cell culture container.

In some embodiments, a computer-implemented method can control fluid movement within a cell culture assembly based on measured or calculated values of the amount of fluid within one or more containers. The cell culture assembly includes a disposable cell culture tray assembly coupled to a reusable base unit. The method includes producing, via an actuator module of an electronic control system of the cell culture assembly, a first valve control signal and a first pump control signal. The first valve control signal causes a valve actuator of the base unit to actuate a multiport valve to fluidically couple a first selectable port of the multiport valve to a master port of the multiport valve. The master port is fluidically coupled to a fluid pump. Each selectable port is fluidically coupled to one of a cell culture container, a second cell culture container, or a cell culture media container. The first pump control signal causes a pump actuator of the base unit to actuate the fluid pump to move a first volume of cell culture media from the cell culture media container to the first cell culture container. A volume of fluid within the first cell culture container is determined. The method includes producing, via the actuator module when the volume of fluid is below a threshold volume, a second valve control signal and a second pump control signal. The second valve control signal causes the valve actuator to actuate the valve or otherwise maintain the fluidic coupling of the first selectable port and the master port of the multiport valve. The second pump control signal causes the pump actuator of the base unit to actuate the fluid pump to move a second volume of cell culture media from the cell culture media container to the first cell culture container. The method includes producing via the actuator module when the volume of fluid is above the threshold volume, a third valve control signal and a third pump control signal. The third valve control signal causes the valve actuator to actuate the multiport valve to fluidically couple a second selectable port of the plurality of selectable ports to the master port of the multiport valve. The third pump control signal causes the pump actuator of the base unit to actuate the fluid pump to move a plurality of cells from the first cell culture container to the second cell culture container.

In some embodiments, a method includes removing a cell culture tray assembly from an outer protective wrap. The tray assembly includes a tray, a first lid, a second lid, and a multiport valve. The first lid is coupled to the tray and configured to be removably coupled to a first container. The first lid includes a first liquid exchange port and a first gas exchange port. The second lid is coupled to the tray and configured to be removably coupled to a second container. The second lid includes a second liquid exchange port and a second gas exchange port. The multiport valve is coupled to the tray and includes a master port and a plurality of selectable ports. A first selectable port of the plurality of selectable ports is aseptically coupled to the first liquid exchange port of the first lid, and a second selectable port of the plurality of selectable ports is aseptically coupled to the second liquid exchange port of the second lid. At least one cell is added to a first container through an opening of the first container. The first lid is secured to the first container to close the opening. The tray assembly is couple to a base unit. A valve actuator of the base unit is engaged with the multiport valve of the tray assembly after coupling the tray assembly or simultaneous with coupling the tray assembly to the base unit. A fluid pump is coupled to a pump actuator of the base unit.

In some embodiments, the method includes, after coupling the tray assembly and coupling a fluid pump, moving the base unit with the tray assembly coupled thereto to an incubation environment. In some embodiments, the method includes removing the multiport valve from the tray assembly and coupling the multiport valve to the base unit such that that the valve actuator of the base unit matingly engages the multiport valve. In some embodiments, removing the multiport valve is performed while the first selectable port of the multiport valve is aseptically coupled to the first lid and the second selectable port of the multiport valve is aseptically coupled to the second lid. In some embodiments, the removing, adding, and securing are done in an aseptic environment. In some embodiments, before securing the first lid to the first container, a volume of reagent and at least one cell are added to the first container. In some embodiments, after securing the first lid to the first container, the first container is coupled to a coupler of the tray assembly. In some embodiments, the method further includes coupling the fluid pump to a port of the multiport valve via tubing. In some embodiments, coupling the fluid pump to the multiport valve includes coupling a master port of the multiport valve to the fluid pump via the tubing.

The term "about" when used in connection with a referenced numeric indication means the referenced numeric indication plus or minus up to 10% of that referenced numeric indication. For example, "about 100" means from 90 to 110. The term "substantially" when used in connection with, for example, a geometric relationship, a numerical value, and/or a range is intended to convey that the geometric relationship (or the structures described thereby), the number, and/or the range so defined is nominally the recited geometric relationship, number, and/or range. For example, two structures described herein as being "substantially parallel" is intended to convey that, although a parallel geometric relationship is desirable, some non-parallelism can occur in a "substantially parallel" arrangement. By way of another example, a structure defining a volume that is "substantially 0.50 milliliters (mL)" is intended to convey that, while the recited volume is desirable, some tolerances can occur when the volume is "substantially" the recited volume (e.g., 0.50 mL). Such tolerances can result from manufacturing tolerances, measurement tolerances, and/or other practical considerations (such as, for example, minute imperfections, age of a structure so defined, a pressure or a force exerted within a system, and/or the like). As described above, a suitable tolerance can be, for example, of +10% of the stated geometric construction, numerical value, and/or range.

As used herein, the term "reagent" includes any substance that is used in connection with any of the reactions described herein. For example, a reagent can include a buffer, an enzyme, a cell culture medium, a wash solution, or the like. A reagent can include a mixture of one or more constituents. A reagent can include such constituents regardless of their state of matter (e.g., solid, liquid or gas). Moreover, a reagent can include the multiple constituents that can be included in a substance in a mixed state, in an unmixed state and/or in a partially mixed state. A reagent can include both active constituents and inert constituents. Accordingly, as used herein, a reagent can include non-active and/or inert constituents such as, water, colorant or the like.

As used herein, the term "set" can refer to multiple features or a singular feature with multiple parts. For example, when referring to set of walls, the set of walls can be considered as one wall with multiple portions, or the set of walls can be considered as multiple, distinct walls. Thus, a monolithically-constructed item can include a set of walls. Such a set of walls can include, for example, multiple portions that are either continuous or discontinuous from each other. A set of walls can also be fabricated from multiple items that are produced separately and are later joined together (e.g., via a weld, an adhesive, or any suitable method)

FIG. 1A illustrates a schematic view of an automated cell culture system according to an embodiment. This example automated cell culture system 100 has three cell culture vessels 111, 113, and 115. These vessels may be laboratory flasks or dishes, for example. The cell culture vessels hold cell cultures, growth medium, and any other additives or reagents associated with cell culture. The cell cultures within the vessels maybe any kind of adherent or suspension cell cultures.

Fluid pumps 103 and 105 pump are one-port fluid pumps that contain an internal fluid reservoir. An example of a one-port fluid pump is a syringe mated to a syringe driver. A syringe fluid pump may draw fluid into its internal reservoir through creating suction in the reservoir by pulling out the syringe's plunger. Similarly, the syringe pump may push fluid out of the reservoir by pushing the plunger back in to the syringe. In other embodiments, one or both of fluid pumps 103, 105 may comprise a bi-directional in-line pump with a separate reservoir. The bi-directional pump may be, for example, a peristaltic pump or impeller-based fluid pump that is capable of pumping fluid in two directions along a fluid channel. A bi-directional in-line pump may be mated to a dedicated reservoir on one end and the other end used as an input and output port with behavior similar to the syringe pump. The dedicated reservoir mated to the pump may be flexible and sealed, e.g., a bag or pouch, such that air pockets do not form in the reservoir when fluid is pumped out of it.

Fluid pumps 103 and 105 are each respectively fluidly connected to multiport valves 107 and 109. Multiport valves 107 and 109 have one master port and a plurality of selectable ports. The multiport valves may selectively fluidly connect the master port to one of the selectable ports at a time. If the master port of a multiport valve is connected to a selected port, other selectable ports are sealed off and not fluidly connected to the master port. When a master port of a multiport valve is fluidly connected to a selectable port, fluid may flow in either direction through the valve. That is, fluid may flow into the multiport valve through the master port and out through the selected port, or fluid may flow in the opposite direction, flowing into the multiport valve through the selected port and out through the master port. In some embodiments, the multiport valve may be a mechanical valve apparatus, and in other embodiments the multiport valve may be comprised of microfluidic chip components.

Fluid pumps 103 and 105, multiport valves 107 and 109, and cell culture vessels 111, 113, and 115 are all fluidly interconnected by fluid channels. In an embodiment, the fluid channels are comprised of flexible tubing. In other embodiments, some or all of the fluid channels may be rigid tubing, or channels in a substrate. In the illustrated example in FIG. 1A, fluid pump 103 is fluidly connected to the master port of multiport valve 107 by flexible tubing. Multiport port 107 has several selectable ports, 107a-d. Selectable port 107a is fluidly connected to cell culture vessel 111, selectable port 107b is fluidly connected to cell culture vessel 113, and selectable port 107c is fluidly connected to cell culture vessel 115. Selectable port 107d is fluidly connected to container 119. Container 119 may be any kind of fluid container for either supply fluid to the automated cell culture system or receiving fluid from the automated cell culture system. For example, container 119 may be a waste container for receiving waste product from the automated cell culture system. In another example, container 119 may contain fresh cell culture media to supply cell culture vessels with fresh media.

Fluid pump 105, multiport valve 109, and container 117 are configured similar to fluid pump 103, multiport valve 107, and container 119. Multiport port 109 has several selectable ports, 109a-d. Selectable port 109a is fluidly connected to cell culture vessel 111, selectable port 109b is fluidly connected to cell culture vessel 113, and selectable port 109c is fluidly connected to cell culture vessel 115. Selectable port 109d is fluidly connected to container 117.

In operation, the combination of fluid pumps, multiport valves, containers, and cell culture vessels in the example illustrated in FIG. 1A may be used to transfer liquids to and from the cell culture vessels and the containers. In some embodiments, a first fluid pump 103 is used for adding media to cell culture vessels from container 119 and a second fluid pump 105 is used for removing media from cell culture vessels to container 117. In another embodiment, a single fluid pump is used for both adding and removing from cell culture vessels and containers. In some embodiments, the components of group 101 including cell culture vessels 111, 113, 115 and multiport valves 107 and 109 may be separable from fluid pumps 103 and 105 and containers 117 and 119. The fluid connections between components in group 101 may be established independently in a first stage of assembly, and then the additional components connected at a later stage. The components of group 101 may be independently sterilized or processed in the first stage, and then introduced to the remainder of components in the second stage. The fluid connections between components of group 101 and other components may be made with aseptic connections so that contaminants are not introduced to the sterilized components of group 101. Cell culture vessels 111, 113, 115 may be connected to the valves 107 and 109 using tubing and aseptic connections, such that the vessels can be aseptically disconnected from the system when the cells in the vessels are to be removed for usage or analysis.

Figure 1B:
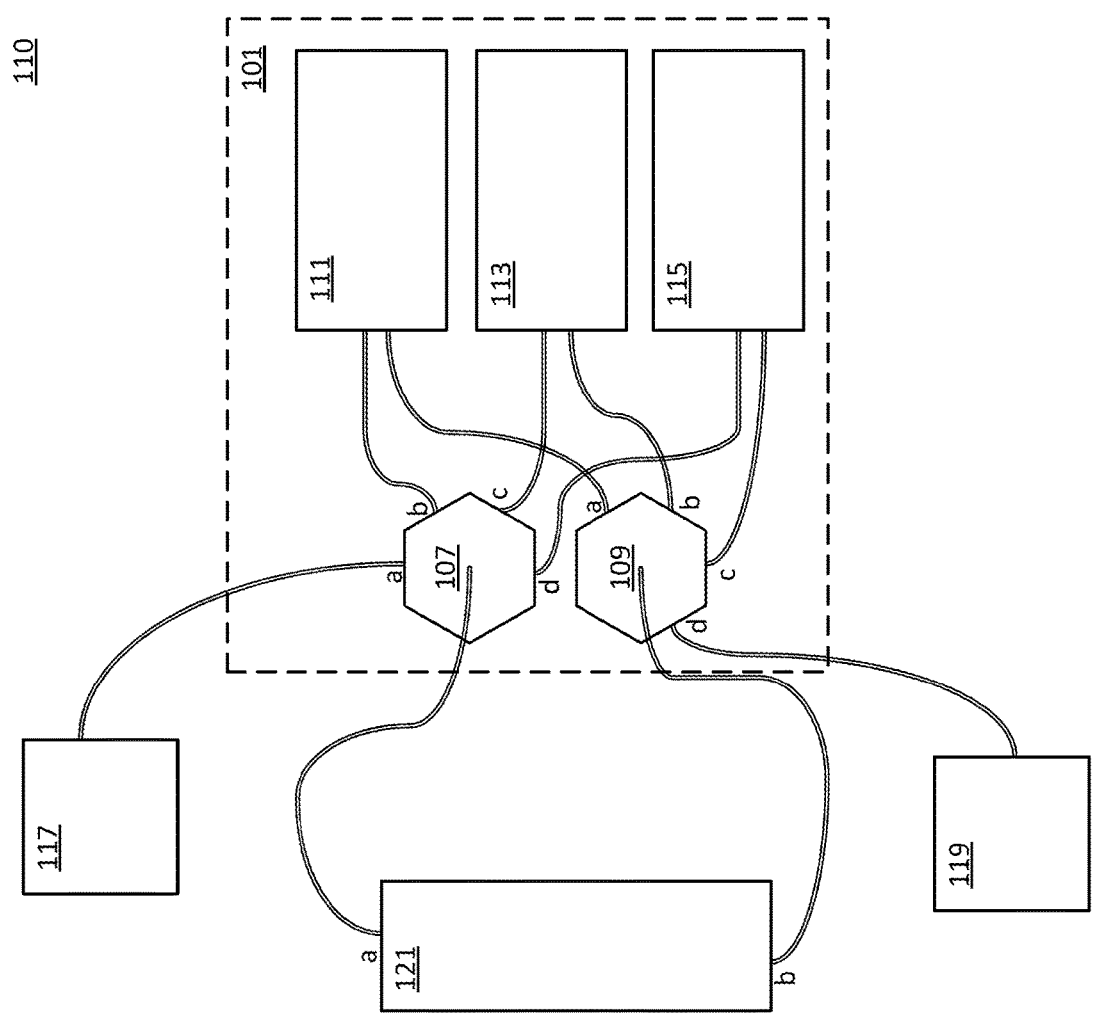
FIG. 1B illustrates a schematic view of an automated cell culture system according to an embodiment.

FIG. 1B illustrates a schematic view of an automated cell culture system according to an embodiment. Automated cell culture system 110 includes one bi-directional fluid pump 121. In this embodiment, cell culture vessels 111, 113, 115, multiport valves 107 and 109, and containers 117 and 119 are the same as described in connection with FIG. 1A. In FIG. 1B, fluid pump 121 is a two-port fluid pump such as a peristaltic pump. A first port 121a of two-port fluid pump 121 is fluidly connected to the master port of multiport valve 107, and a second port 121b of fluid pump 121 is fluidly connected to the master port of multiport valve 109. The fluid pump 121 is capable of pumping fluid in two directions. In a first mode of operation, fluid pump 121 pumps fluid from port 121a to port 121b, and in a second mode of operation fluid pump 121 pumps fluid from port 121b to port 121a.

Figure 2:
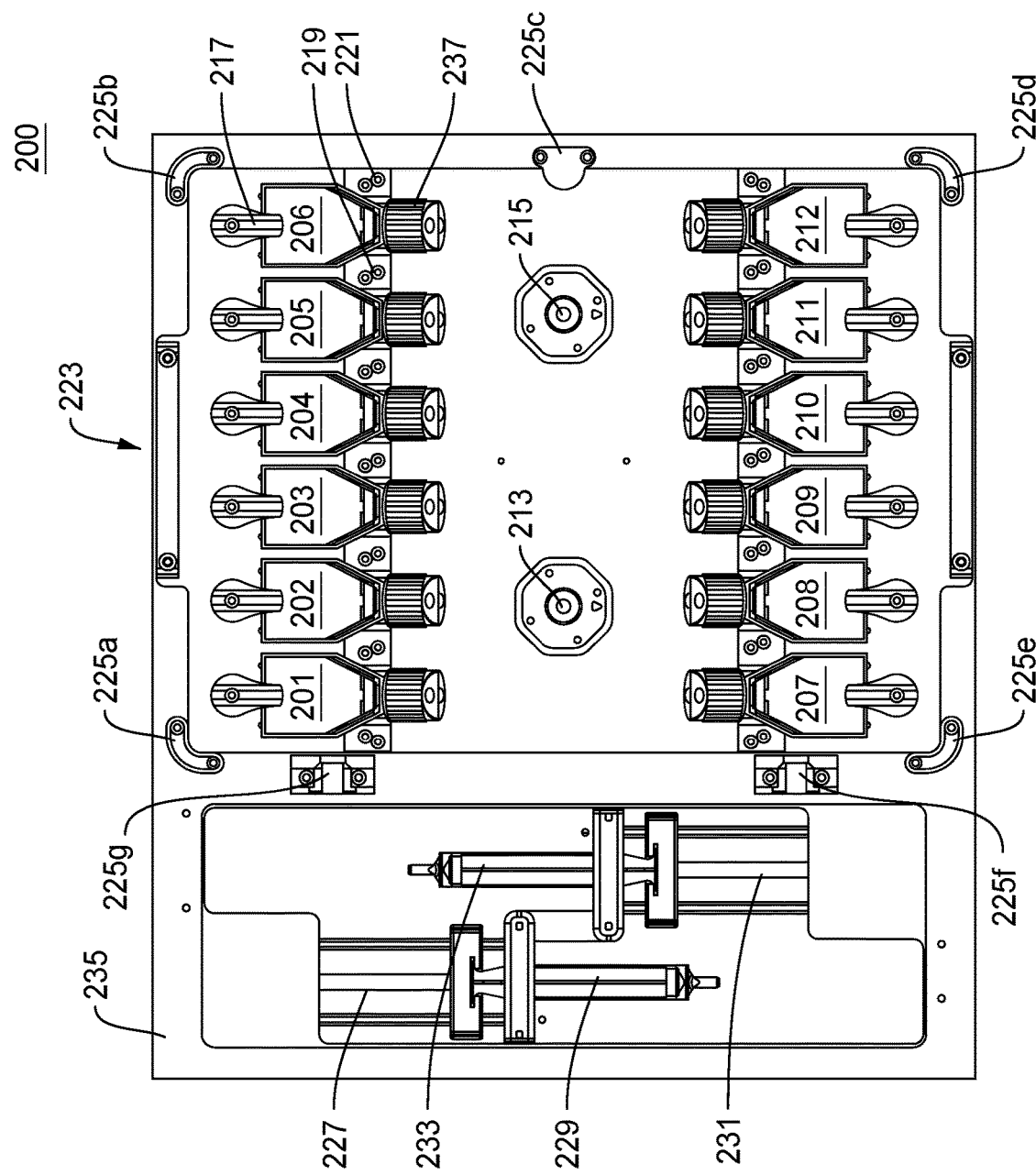
FIG. 2 illustrates a top view of an automated cell culture system according to an embodiment.

FIG. 2 illustrates a top view of an automated cell culture system according to an embodiment. Automated cell culture system 200 has two fluid pumps, two multiport valves, and 12 cell culture vessels. No fluid connections are included in the illustrated example for clarity, however it is to be understood that at least some of the various components of an automated cell culture system would be fluidly connected when in use. Removable tray 223 contains cell culture vessels 201-212 and multiport valves 213 and 215. Each cell culture vessel is capped by an aseptic lid such as aseptic lid 237 which caps cell culture vessel 206. Each cell culture vessel is removably affixed to removable tray 223 by brackets such as brackets 217, 219, and 221 which hold cell culture vessel 206. Removable tray 223 is removably inserted into base housing 235, and guided in by way of guides 225a-f. Base housing 235 contains two syringe-style fluid pumps. A first fluid pump is comprised of syringe 229 and syringe actuator 227. Syringe actuator 227 pushes and pulls on the plunger of syringe 229, effecting fluid flow into and out of the syringe. In an embodiment, syringe actuator is a linear actuator, however any other method of pushing and pulling a syringe plunger may be used. A second pump is comprised of syringe 233 and syringe actuator 231.

Figure 3A:
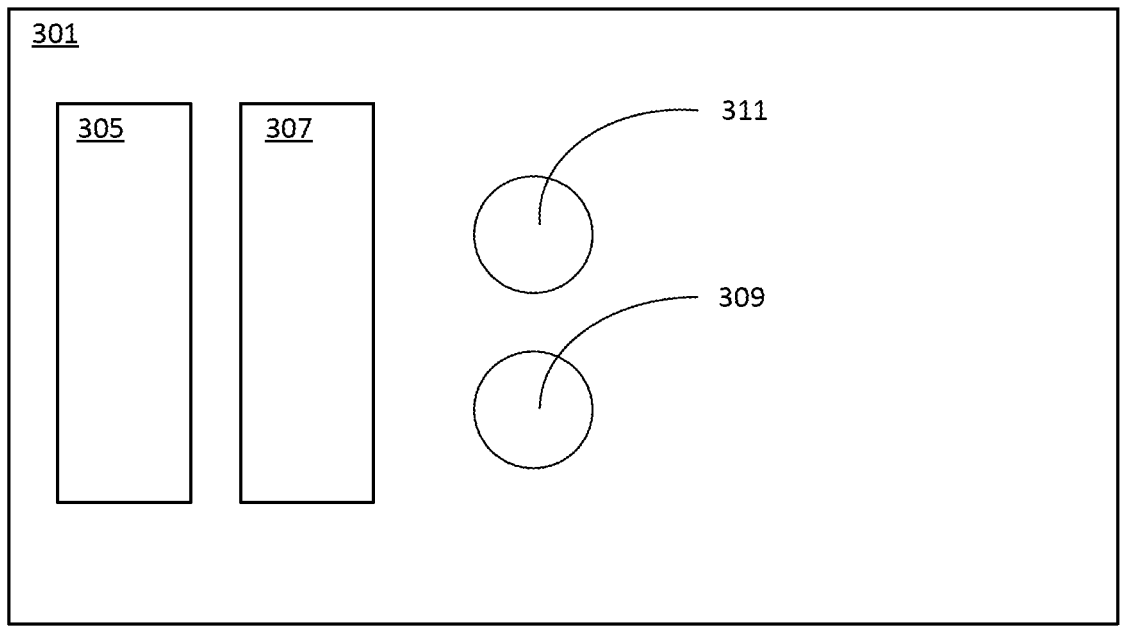
FIG. 3A illustrates a top-down view of a base housing of an automated cell culture system according to an embodiment.

FIG. 3A illustrates a top-down view of a base housing of an automated cell culture system according to an embodiment. The illustrated example base housing 301 contains fluid pumps 305 and 307 and multiport valve actuators 309 and 311. Base housing 301 also includes a controller which controls actuation of fluid pumps, multiport valves, and any other systems such as automated cell counter systems, hemocytometers, imaging systems, microscopes, or other measurement or analysis systems to facilitate automated cell growth. The controller may include one or more processors configured to execute instructions contained on one or more memory systems to control the automated cell culture system and other corresponding systems. In addition, the controller may include one or more network interfaces through which various notifications or data transfers may be sent or received.

Figure 3B:
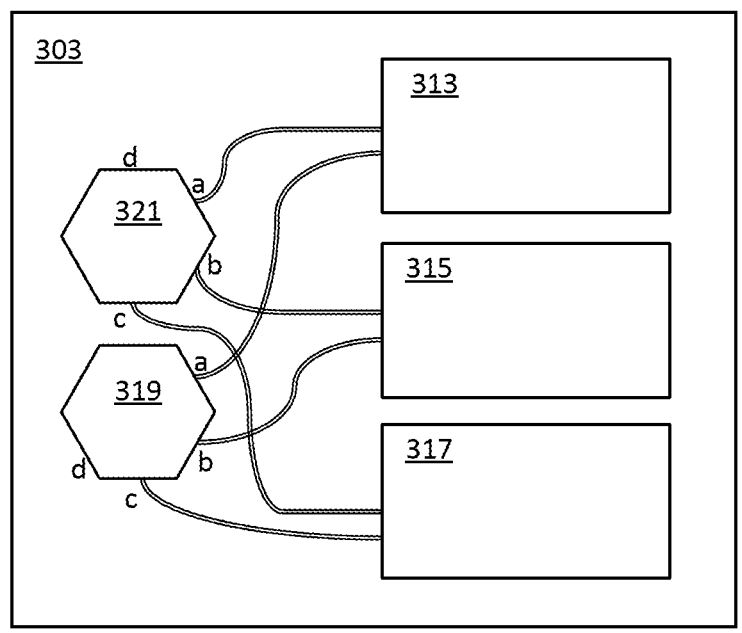
FIG. 3B illustrates a removable tray assembly of an automated cell culture system according to an embodiment.

FIG. 3B illustrates a removable tray assembly of an automated cell culture system according to an embodiment. Removable tray assembly 303 is configured to mate to base housing 301. When removable tray assembly 303 is placed on top of base housing 301, multiport valve actuators 309 and 311 mechanically couple with multiport valves 319 and 321, respectively. For example, in an embodiment, multiport valve actuator 309 rotates an internal member of multiport valve 319 to align a master port of multiport valve 319 with one of the selectable ports 319a-d. Multiport valves 319 and 321 and cell culture vessels 313, 315, and 317 are carried on removable tray 303. When base housing 301 and removable tray 303 are combined, fluid pumps 305 and 307 may be fluidly connected to the master ports of multiport valves 319 and 321.

In some embodiments, base housing 301 may also include an agitator configured to agitate the removable tray assembly 303 in relation to the base housing. This agitator may agitate the tray in a rocking motion, vibrating motion, circular swirling motion, or other motions useful in cell culturing. In some embodiments, individual cell culture vessels may be independently agitated by independent agitators displaced between the cell culture vessel and the removable tray: Independent agitators may be used in applications where it would be disadvantageous to agitate all cell culture vessels of a tray when only a subset of cell culture vessels require agitation. In some embodiments, independent agitators may be integrated into a bracket or brackets used to affix cell culture vessels to the removable tray. In some embodiments, agitators may have active components disposed within the base housing that mechanically mate to passive components on the removable tray, similar to how multiport valves on the removable tray may mechanically couple to actuators in the base housing.

In use, removable tray 303 may be configured with any number or configuration of multiport valves, cell culture vessels, and fluid tubing as required separate from base housing 301. The removable tray 303 and its associated components may then be sealed and sterilized before being introduced to base housing 301. In some embodiments, the cell culture vessels may be added to the tray 303 in a sterile environment after sterilization of the tray 303. The base housing 301 may remain stationary, and any electromechanically components such as valve actuators and pump mechanisms disposed within the base housing need not be subject to transport or sterilization procedures as the components of the base housing are not in fluid contact with the sterile system on the removable tray 303. If a syringe-style fluid pump is used, a sterile syringe may be placed in the syringe actuator for use, such that the syringe actuator is not in contact with any fluids in the sterile system. Similarly, a peristaltic pump may use a sterile portion of tubing such that the stationary components associated with the base housing do not come in fluid contact with the sterile system.

Figure 4:
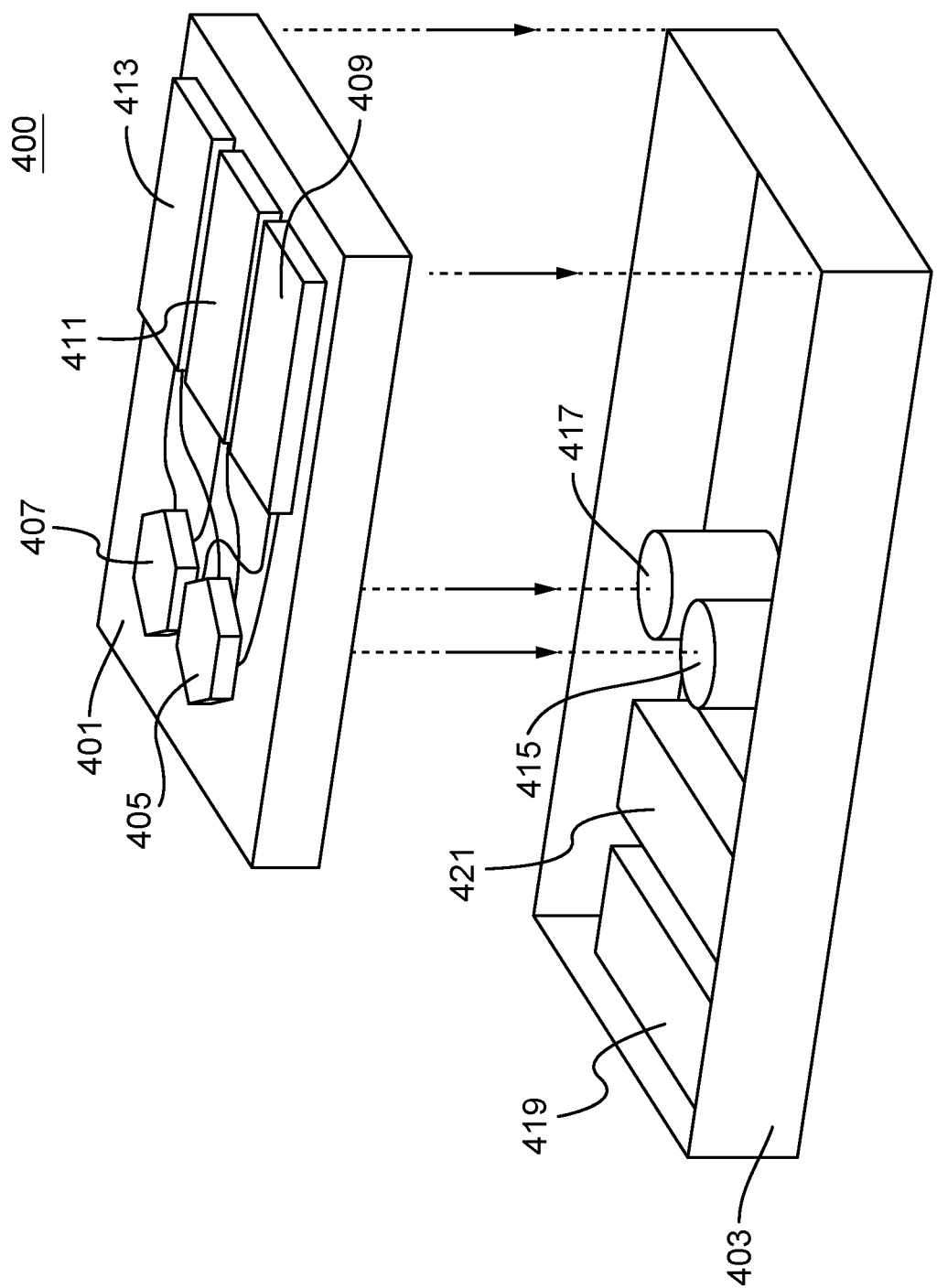
FIG. 4 illustrates an example removable tray of an automated cell culture system being mated to an example base housing according to an embodiment.

FIG. 4 illustrates an example removable tray of an automated cell culture system being mated to an example base housing according to an embodiment. As illustrated in this example, automated cell culture system 400 includes removable tray 401 and base housing 403. Removable tray 401 contains multiport valves 405 and 407 and cell culture vessels 409, 411, and 413. Removable tray 401 is lowered down onto base housing 403 where multiport valve actuators 415 and 417 align with multiport valves 405 and 407, respectively. Once removable tray 401 is lowered down onto base housing 403, multiport valve actuators 415 and 417 mechanically couple with multiport valves 405 and 407. After the two parts are joined, fluid pumps 419 and 421 are fluidly connected, such as by a manual connection step, to multiport valves 405 and 407 on-board the removable tray.

Figure 5:
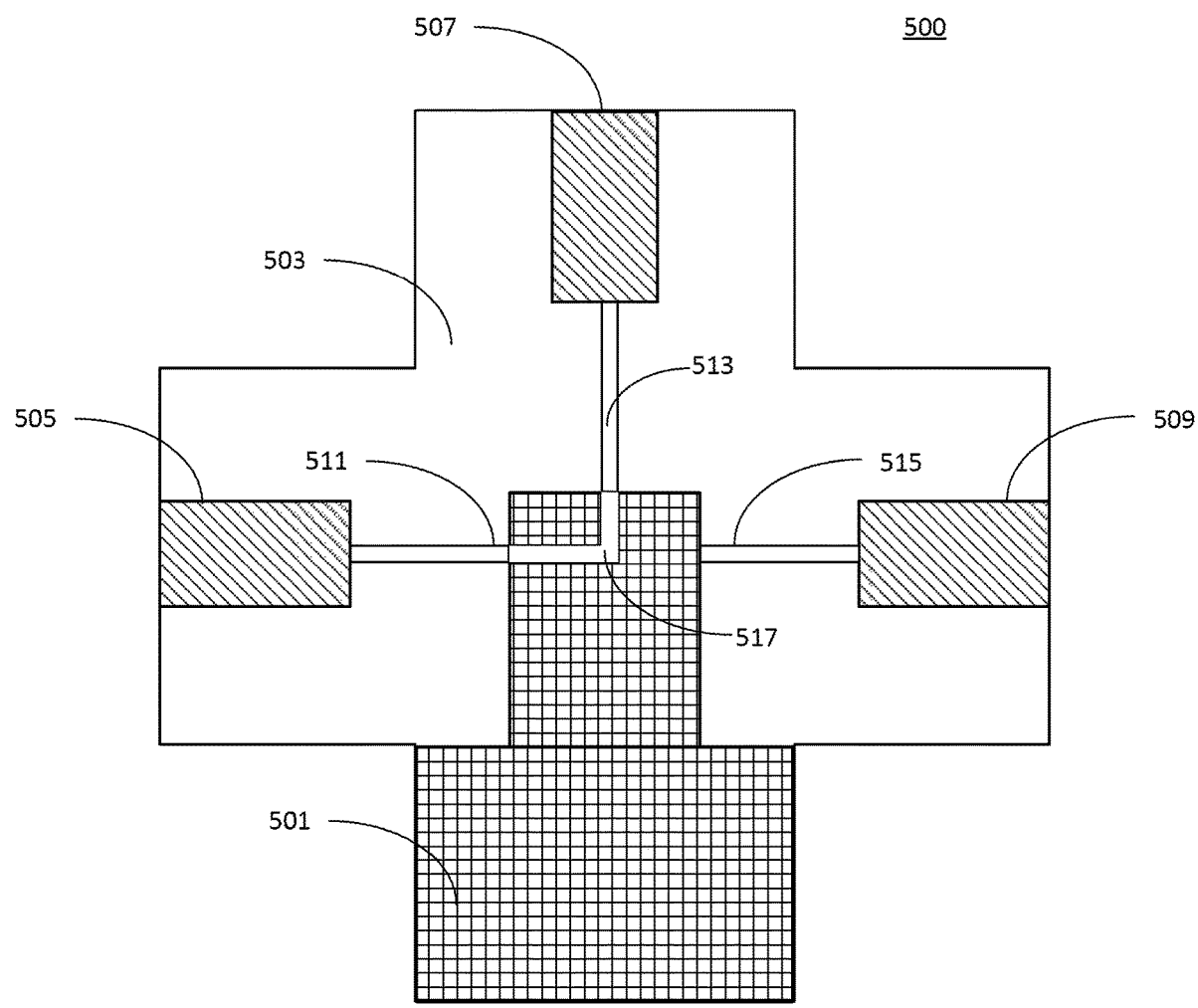
FIG. 5 illustrates a cross-sectional view of an example multiport valve according to an embodiment.

FIG. 5 illustrates a cross-sectional view of an example multiport valve according to an embodiment. In this embodiment, a multiport valve 500 comprises a valve body 503 having master port 507 on a top side and a plurality of selectable ports 505 and 509 dispersed around its circumference. Two selectable ports are illustrated in this cross-sectional view: however, it is to be understood that various embodiments of multiport valves may include any number of selectable ports.

Valve body 503 has a cylindrical cavity on its underside to which rotatable cylindrical valve rotor 501 is inserted. Within rotatable cylindrical valve rotor 501 is a fluid channel 517 which fluidly connected an axial master port of rotatable cylindrical valve rotor 501 to a radial master port of rotatable cylindrical valve rotor 501. Within valve body 503 is a fluid channel 513 which fluidly connects master port 507 to fluid channel 517 of rotatable cylindrical valve rotor 501. The connection between fluid channel 513 and fluid channel 517 remains constant as rotatable cylindrical valve rotor 501 rotates because both fluid channels are centered on the axis of rotation of rotatable cylindrical valve rotor 501 within the cylindrical cavity of valve body 503.

In the state illustrated in FIG. 5, rotatable cylindrical valve rotor 501 is rotated such that fluid channel 511 is aligned with fluid channel 517. Thus, a fluid circuit is established from master port 507 to selectable port 505 through fluid channel 513, fluid channel 517, and fluid channel 511. In this illustrated state, fluid channel 515 and, in turn, selectable port 509, is sealed off by the presence of a solid portion of rotatable cylindrical valve rotor 501. In operation, rotatable cylindrical valve rotor 501 may rotate to establish a fluid pathway from master port 507 to selectable port 509 while sealing off selectable port 505 and fluid channel 511.

Multiport valve 500 may be made of any appropriate material, and valve body 503 and valve rotor 501 may be made of the same or different materials. Examples of materials that may be used include plastics, TFE-based materials such as polytetrafluoroethylene PTFE, metals, rubbers, or similar materials. In some embodiments, the valve body 503 and valve rotor 501 may be machined to fit with very close tolerances so that a fluid-tight seal is created between the two components. In some embodiments, additional gaskets, bearings, seals, and/or flanges may be incorporated into multiport valve 500 to provide for a fluid-tight connection between valve body 503 and valve rotor 501.

Figure 6A:
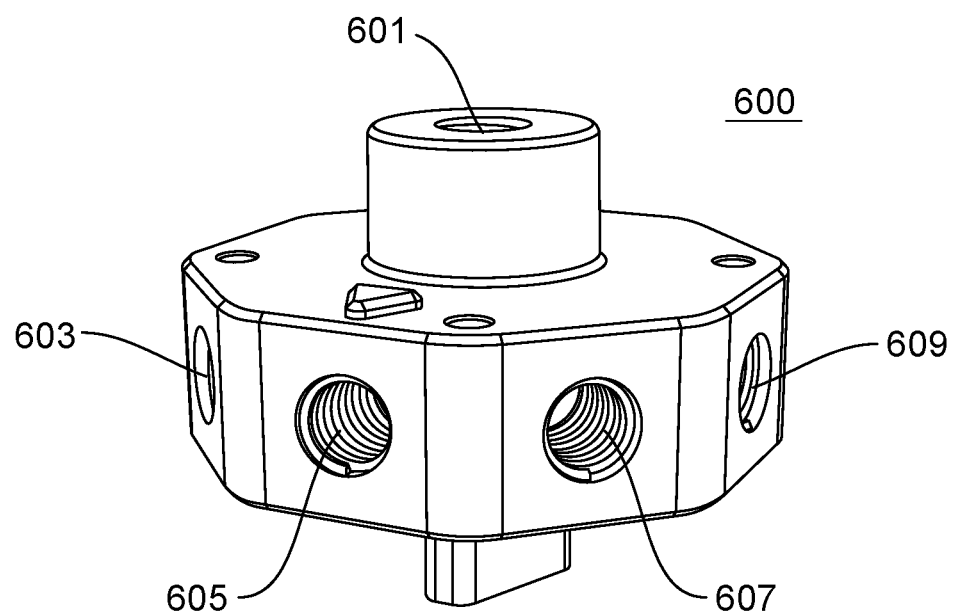
FIG. 6A illustrates an example multiport valve according to an embodiment.
Figure 6B:
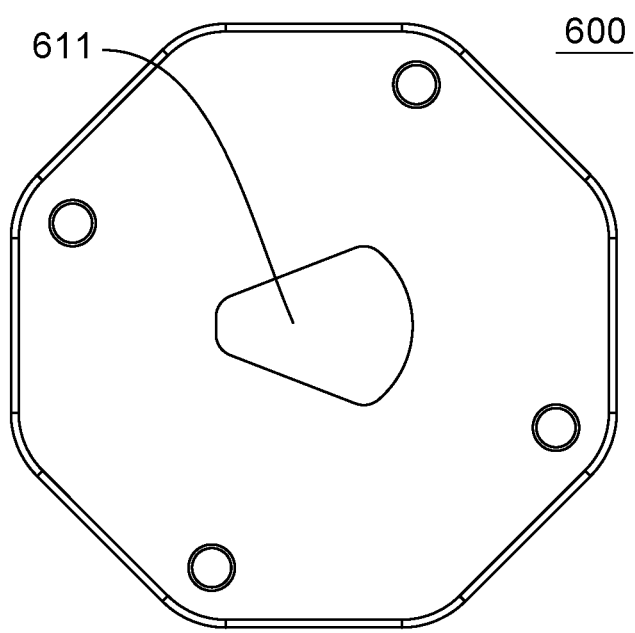
FIG. 6B illustrates a bottom view of an example multiport valve.

FIG. 6A illustrates an example an example multiport valve according to an embodiment. In this example, multiport valve 600 has an axial port 601 and eight selectable ports, of which four (ports 603, 605, 607, and 609) are viewable in the perspective view of FIG. 6A. FIG. 6B illustrates a bottom view of multiport valve 600 showing a mechanical coupler 611 which is configured to mechanically couple to a multiport valve actuator. A corresponding multiport valve actuator has a cavity shaped to accept mechanical coupler 611 and transfer rotational mechanical energy to the multiport valve 600.

Figure 7:
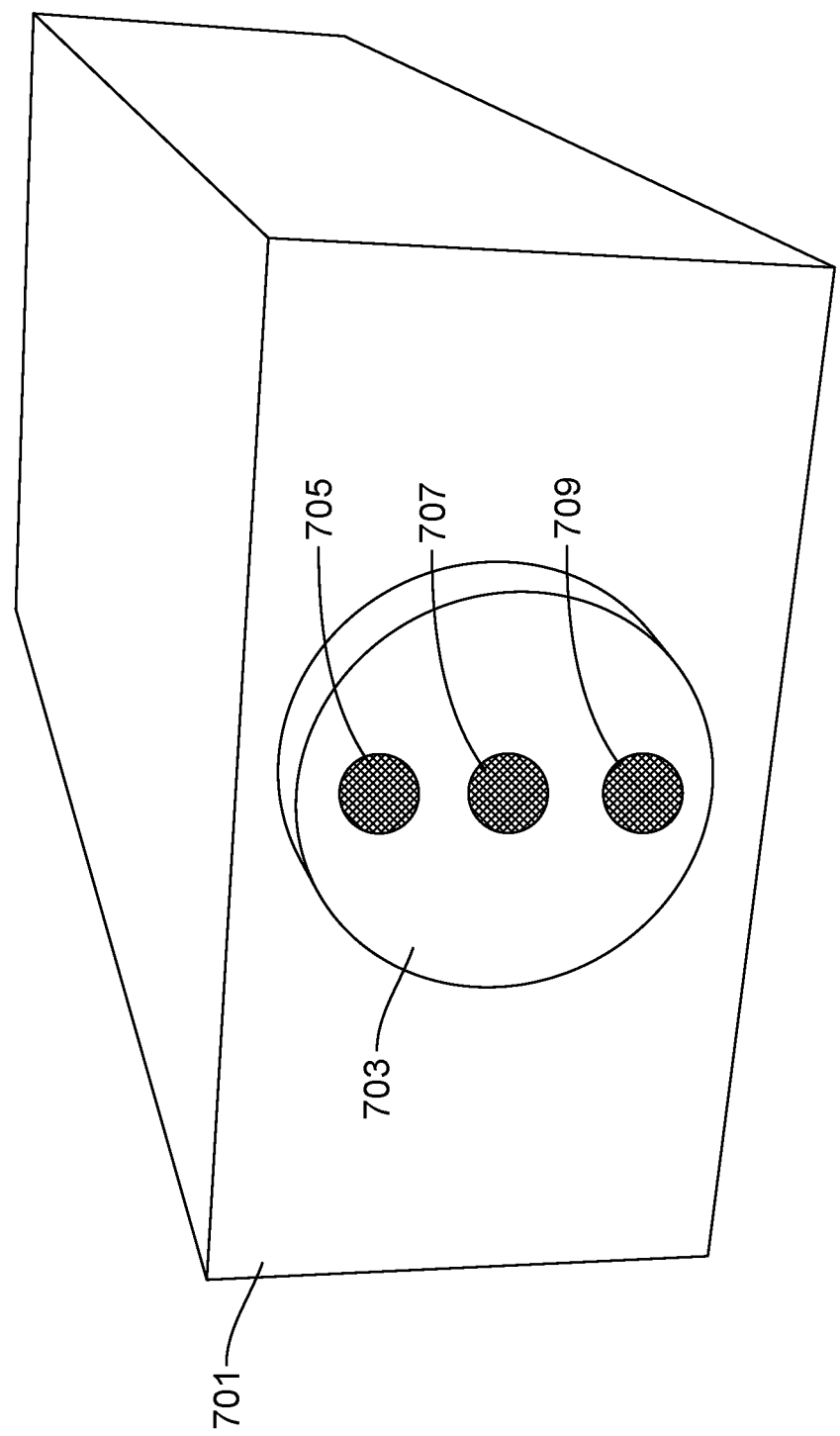
FIG. 7 illustrates a cell culture vessel lid according to an embodiment.

FIG. 7 illustrates an aseptic cell culture vessel lid according to an embodiment. In this example embodiment, cell culture vessel lid 703 is affixed to cell culture vessel 701. In this example embodiment, cell culture vessel lid 703 has three ports 705, 707, and 709. In this example, the three ports are vertically aligned. If the cell culture vessel 701 is filled with liquid such as cell growth media, tubing entered via the lowest port 709 may be submerged in the liquid such that the liquid may be siphoned out via port 709 using the tubing. Tubing entering via the middle port, port 707, may be placed so that the tubing is not in liquid contact with the contents of the cell culture vessel, so that additional liquid may be added to the cell growth vessel without contaminating the fluid path to port 707. Port 705 may be configured to allow gas exchange in and out of the cell growth vessel 701. In some embodiments, port 705 includes a filter for filtering gas on the way into the flask to sterilize the gas. In some applications, the automated cell culture system may be placed in an incubation chamber to regulate the environment in proximity to the cell culture vessel. The incubation chamber may be integrated with the automated cell culture system base housing in some embodiments. In one embodiment, characteristics of the environment to be regulated include gas mix, temperature, and humidity levels. In one embodiment, the incubation chamber modulates gas mix, temperature and humidity levels depending on the cell line to be grown. In some embodiments, port 705 may be attached to an environmental regulation device that manages the temperature, humidity, oxygenation, gas mix, and other such parameters of the gaseous environment within the cell culture vessel. Aseptic lids may be created to fit any cell culture vessel, such that any culture vessel used for manual cell culture can be integrated with the system.

Figure 8:
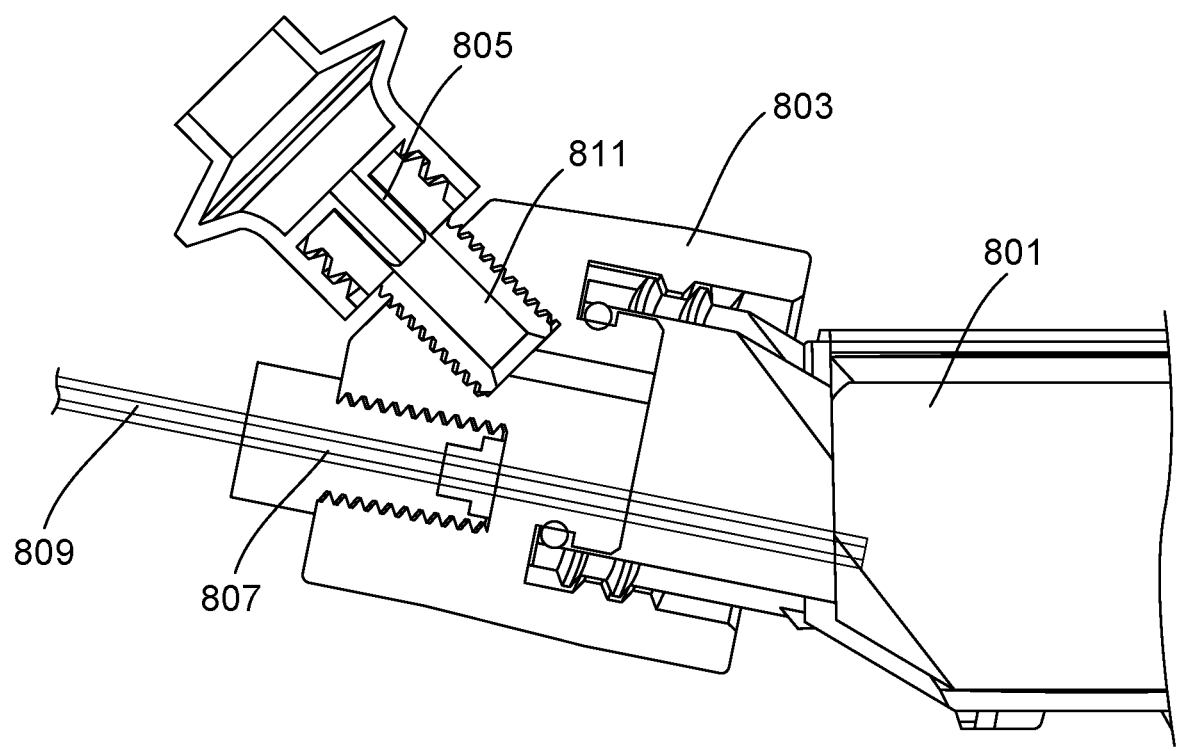
FIG. 8 illustrates a cross-sectional view of a cell culture vessel lid according to an embodiment.

FIG. 8 illustrates a cross-sectional view of a cell culture vessel lid according to an embodiment. Cell culture vessel lid 803 is screwed onto the mouth of cell culture vessel 801 such that the threads of cell culture vessel lid 803 engage with the threads of the mouth of cell culture vessel 801. In this example embodiment, cell culture lid 803 has a liquid port 807 and a gas port 811. A liquid channel 809 is threadedly engaged with liquid port 807. A gas filter 805 is threadedly engaged with gas port 811. Gas filter 805 may allow gas exchange in and out of the cell culture vessel while blocking any microbes or pathogens from entering the cell culture vessel from the outside. In an embodiment, gas filter 805 is a 0.22 micron filter.

Figure 9:
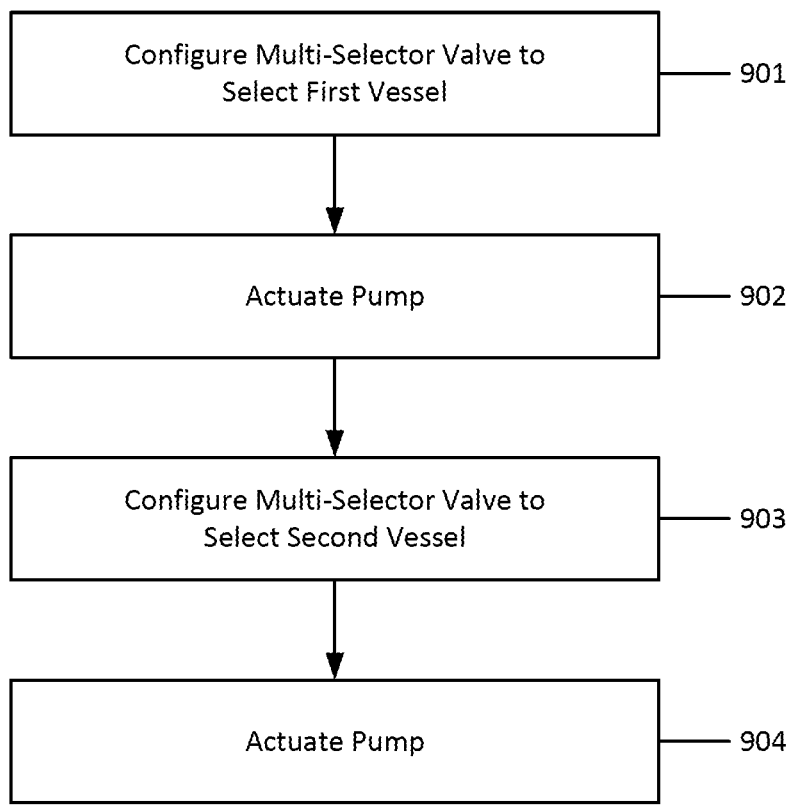
FIG. 9 illustrates the steps of a method for transferring liquid from a first vessel to a second vessel using an automated cell culture system with a single-port pump according to an embodiment.

FIG. 9 illustrates the steps of a method for transferring liquid from a first vessel to a second vessel using an automated cell culture system with a single-port pump according to an embodiment. In this example, an automated cell culture system has a single-port pump such as a syringe-type pump as discussed above, or a two-port pump with a holding vessel attached to one port. This method may be used to transfer liquid from any vessel to another vessel. For example, the first vessel may be a cell culture vessel, and the second vessel may be a waste container. In another example, the first vessel may be a container of fresh cell growth media and the second container may be a cell culture vessel.

In FIG. 9, at step 901, a multiport valve with a master port either connected to a single-port pump or connected to a two-port pump with a holding vessel, is configured to select a selectable port in fluid communication with a first vessel. At step 902, the single-port pump is actuated so that fluid is drawn out of the first vessel and into the reservoir of the single-port pump, or similarly the two-port pump is actuated so that fluid is drawn into the holding vessel. Next, at step 903, the multiport valve is configured to select a selectable port in fluid communication with a second vessel. Then, at step 904, the fluid is pumped out of the reservoir of the single-port pump, or similarly pumped out of the holding vessel by the two-port pump, through the configured multiport valve, and into the second vessel.

Figure 10:
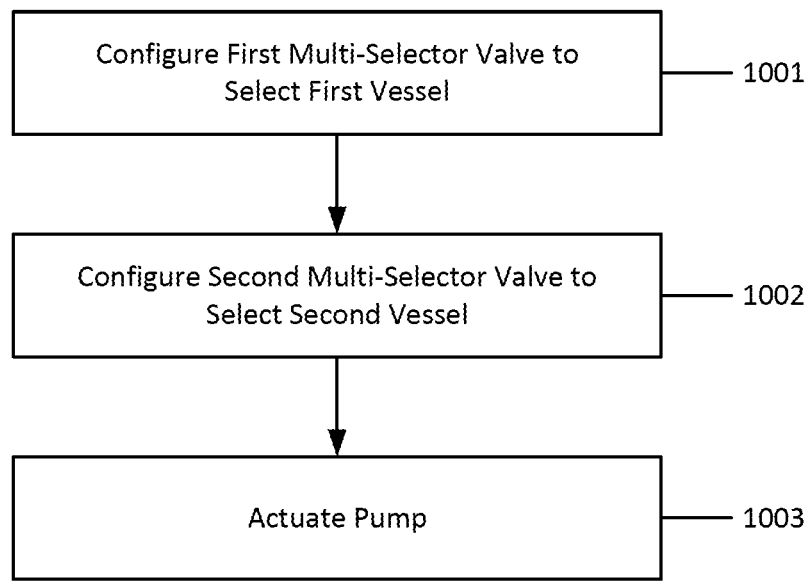
FIG. 10 illustrates the steps of a method for transferring liquid from a first vessel to a second vessel using an automated cell culture system with a two-port pump according to an embodiment.

Some embodiments of an automated cell culture system may use two-port pumps with a multiport valve fluidly connected to each port. A two-port pump may be unidirectional or bidirectional. The two-port pump does not need to transfer liquid into a holding reservoir like a single-port pump but may pump directly from one vessel to another. FIG. 10 illustrates the steps of a method for transferring liquid from a first vessel to a second vessel using an automated cell culture system with a two-port pump according to an embodiment. In this example, a first port of the two-port pump is fluidly connected to the master port of a first multiport valve, and the second port of the two-port pump is fluidly connected to the master port of a second multiport valve. At step 1001, the first multiport valve is configured to select a selectable port in fluid communication with a first vessel. At step 1002, the second multiport valve is configured to select a selectable port in fluid communication with a second vessel. Finally, at step 1003, the two-port pump as actuated to pump in the direction of the first port to the second port, such that liquid from the first vessel is pumped into the second vessel.

For any embodiments disclosed herein, a simple reference to pumping from a first vessel to a second vessel may refer in the alternative to the appropriate method depending on whether an automated cell culturing system is configured with a one-port pump or a two-port pump. Some embodiments of an automated cell culture system may also combine two-port and single port pumps in one system, such that one step of pumping may use one type of pump and another step of pumping may use a different type of pump.

In some embodiments, media from different sources may be fed to the cells, depending on an observed condition of the cells, for example if signs of differentiation are observed for stem cells. In an embodiment, a first step of a method is observing a condition of the cells, such as signs of differentiation in stem cells. The first step may be performed by a microscope, camera, or other measurement device. A second step of the method is selecting an appropriate source of media based on the condition of the cells. A third step of the method is actuating the one-port pump or two-port pump system to transfer media from the selected source of media to a vessel containing the cells.

In some embodiments, an automated cell culture system includes a microscope that may be moved to image the contents of any cell culture vessel of the automated cell culture system. In some examples, the microscope may be mounted on a mechanical system that is capable of moving the microscope to the cell culture vessels such as a 2-dimensional or 3-dimensional gantry mechanism or a hinged robotic arm mechanism. In some embodiments, the microscope may remain stationary while the automated cell culture system is moved to position individual cell culture vessels in view of the stationary microscope. In some embodiments, the microscope and moving assembly may be contained within the base housing of an automated cell culture system, such that the cell culture vessels may be imaged from their bottom side. In such embodiments, the removable tray holding the cell culture vessels may have transparent windows or cutouts underneath the cell culture vessels to allow a microscope to image the cells contained therein. In some embodiments, an adjustable and controllable light source is placed on the opposite side of the cell culture vessel as the microscope to provide a light source for the microscope. For example, a light source may be mounted on mechanical system that is capable of moving the light source to any cell culture vessel as necessary, similar to the microscope. In some embodiments, a stationary light source may be placed on one side of the automated cell culture system such that each cell culture vessel is sufficiently illuminated.

The automated cell culture system may include other imaging devices as well. For example, the automated cell culture system may include one or more cameras or pairs of LEDs and light sensors to image the contents of cell culture vessels. This type of imager may be useful to measure and monitor macro-level visual properties of the cell culture vessels. For example, a color camera, or pairs of LEDs and light sensors, may be useful for monitoring the color of the contents of a cell culture vessel containing a color-based pH indicator such as phenol red from which the pH of the contents of the cell culture vessel may be determined. In an embodiment, each cell culture vessel bracket may include a camera to image the contents of a cell culture vessel. In another embodiment, a single camera may be mechanically movable to each cell culture vessel, in the same or a similar way as a microscope may be moved, to image each cell culture vessel. In an embodiment, an LED and light sensor may be mechanically movable to each cell culture vessel, in the same or a similar way as a microscope may be moved, to monitor the color of a cell culture vessel.

In some example implementations, one or more off-tray devices may be interfaced with the automated cell culture system. For example, an automated cell counter machine may be fluidly connected to a selectable port of a multiport valve such that samples of the contents of cell culture vessels may be transported to the automated cell counter machine. In some embodiments, the automated cell counter machine may be controlled by the controller such that the entire process of counting cells with the automated cell counter machine is automated by the automated cell culture system. By way of further example, a cell counting chamber may be fluidly connected to a selectable port of a multiport valve such that samples of the contents of cell culture vessels may be transported to the cell counting chamber. A microscope may image the cell counting chamber to count the cells in the cell counting chamber. By way of further example, an external chamber may be fluidly connected to a selectable port of a multiport valve such that samples of the contents of cell culture vessels may be transported to the external chamber. An LED and light sensor may be used to measure the cloudiness of solution in the external chamber. By way of further example, in order to take a sample of cells, a sampling vessel may be aseptically connected to a port on a multiport valve such that samples of the contents of cell culture vessels may be transported to the vessel, and then the vessel can be aseptically disconnected and the cells taken away.

Various support methods or procedures may be necessary for some operations of an automated cell culture system. For example, a fluid line or pump may need to be primed prior to pumping a liquid through the line. As an example, the fluid line from a bottle of new growth media to a multiport valve may need to be primed prior to pumping new growth media to cell culture vessels. To do this, a small amount of new growth media may be pumped from the new growth media bottle to a waste bottle to ensure that the line is free of air pockets.

Similarly, a line, pump, or valve may need to be cleaned or flushed periodically to remove contaminants. This may be accomplished by pumping a wash fluid through the line, pump, or valve for a period of time or until the line, pump, or valve is sufficiently flushed.

Figure 11:
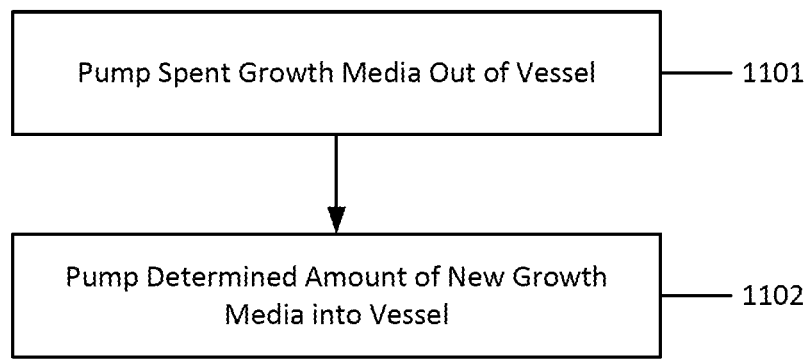
FIG. 11 illustrates the steps of a method for replacing cell culture media during adherent cell line maintenance.

FIG. 11 illustrates the steps of a method for adherent cell line maintenance. At step 1101, the spent cell culture growth media in a vessel is pumped out of the vessel and into a waste container. At step 1102, a determined amount of new cell culture growth media is pumped into the vessel.

Figure 12:
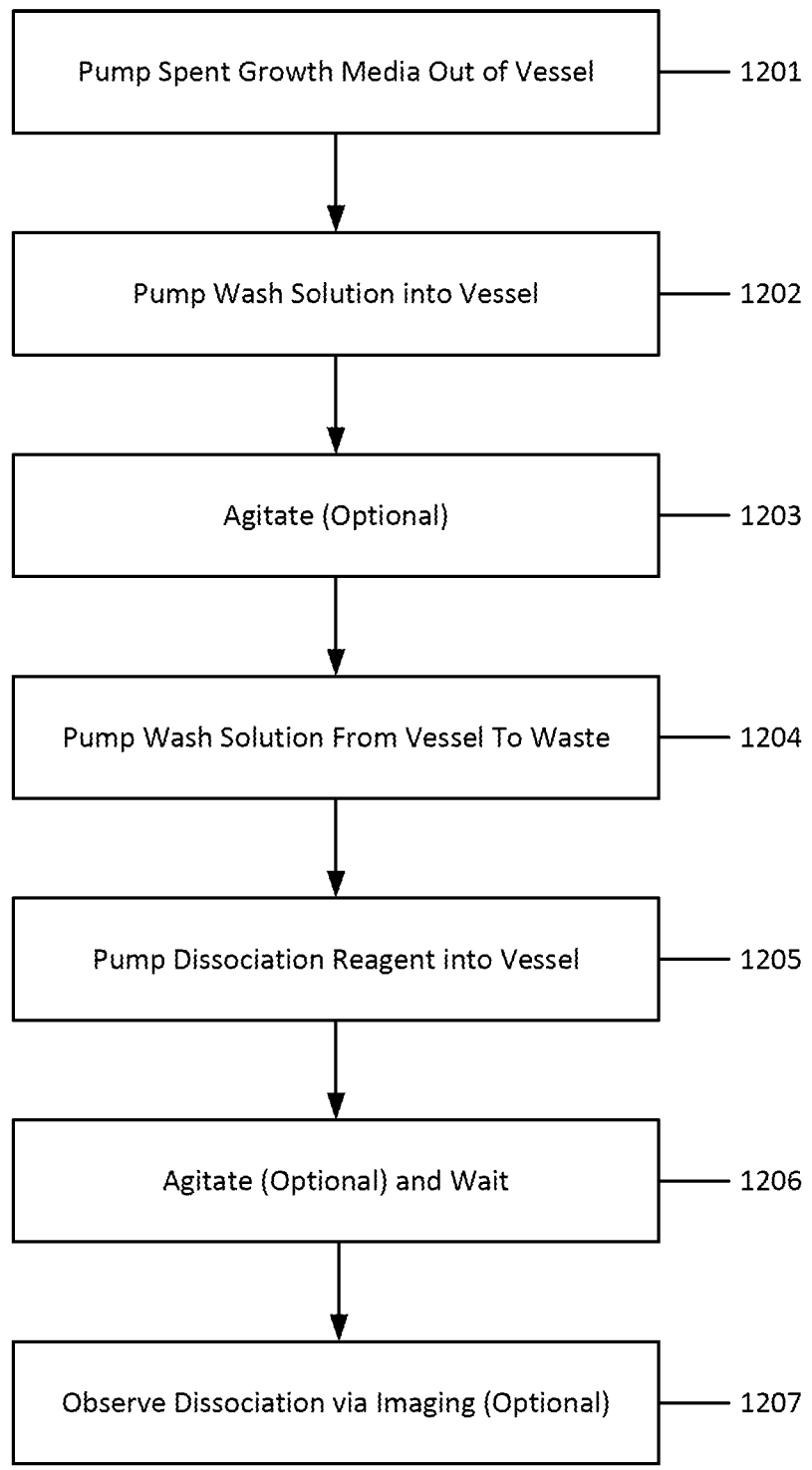
FIG. 12 illustrates the steps of a method for adherent cell line maintenance or expansion with passaging to a new cell culture vessel.
Figure 12:
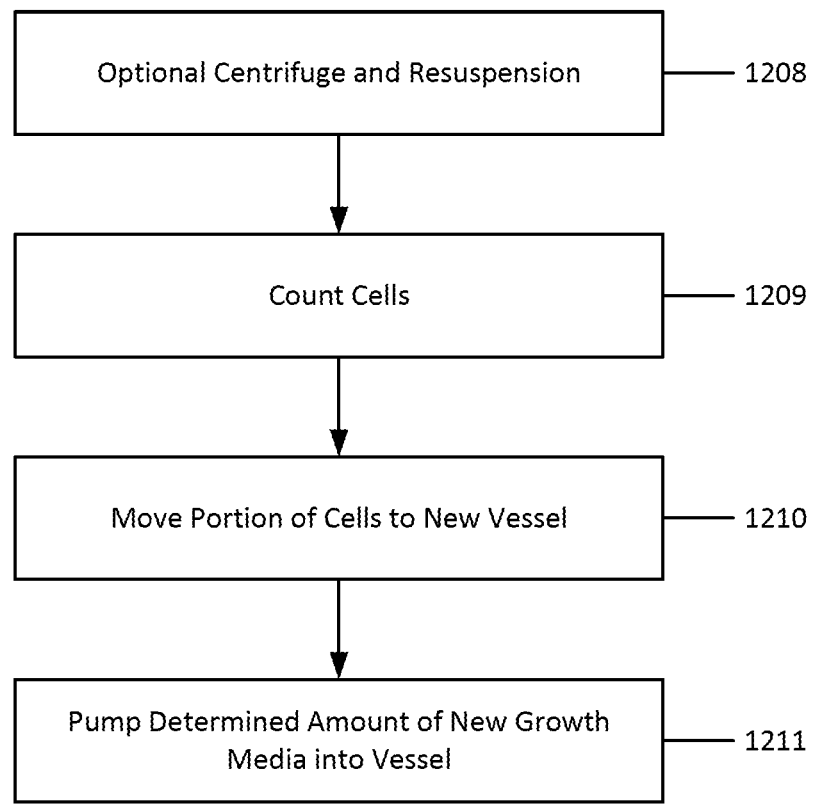

FIG. 12 illustrates the steps of a method for adherent cell line maintenance or expansion with passaging to a new cell culture vessel. In contrast to the method discussed in connection with FIG. 11, here the adherent cells of a cell culture vessel are transferred to a new vessel. At step 1201, the cell culture growth media in a vessel is pumped out of the vessel and into a waste container. Then, at step 1202, a wash solution is pumped into the vessel and at step 1203 the vessel may optionally be agitated. Next, the wash solution is pumped out of the vessel and into a waste container in step 1204.

At step 1205, a dissociation reagent is pumped into the vessel. An example of a dissociation reagent is trypsin. The dissociation reagent is used to resuspend cells adherent to the cell culture vessel walls. Depending on the cells being cultured and the dissociation reagent used, the cell culture vessel may be gently agitated to assist in separating the adherent cells from the cell culture vessel walls. The automated cell culture system then waits a configurable amount of time at step 1206 depending on the cells being cultured and the dissociation reagent used. In an alternative embodiment, the automated cell culture system dynamically monitors the dissociation of the cells from the vessel with a microscope to determine when the amount of dissociation reaches a threshold value. The vessel may optionally be agitated during the waiting in step 1206. At step 1207, optionally, the cells are imaged to observe the detachment of the adherent cells. If the cells are not sufficiently detached, the automated cell culture system may wait an additional amount of time. Once the adherent cells are sufficiently detached from the walls of the cell culture vessel, a dissociation reagent inhibitor or neutralizer may be pumped into the cell culture vessel to stop the dissociation reagent action. At step 1208, the contents of the cell culture vessel may optionally be removed from the automated cell culture system and spun inside a centrifuge to separate the cells from the liquid contents of the cell culture vessel, and then resuspended. The cells may be counted at step 1209 to determine the total number of cells or cell density and the percent viability: At step 1210, a portion of the cells are transferred to a new cell culture vessel. Then, at step 1211, a determined amount of new growth media is pumped into the new vessel. If the automated cell culture system is configured to only maintain the cell line, the original cell culture vessel may be detached from the system and discarded, such that only the new vessel remains in the system growing cells. If the automated cell culture system is configured for expansion of the cell line, the original vessel may be retained, and a proportional amount of new growth media added to it such that both the original and the new cell culture vessel remain in the system growing cells. While described in the context of using a single new vessel, it is to be understood that this process may be expanded to any number of vessels such that a single original vessel may be split between any number of new vessels.

Figure 13:
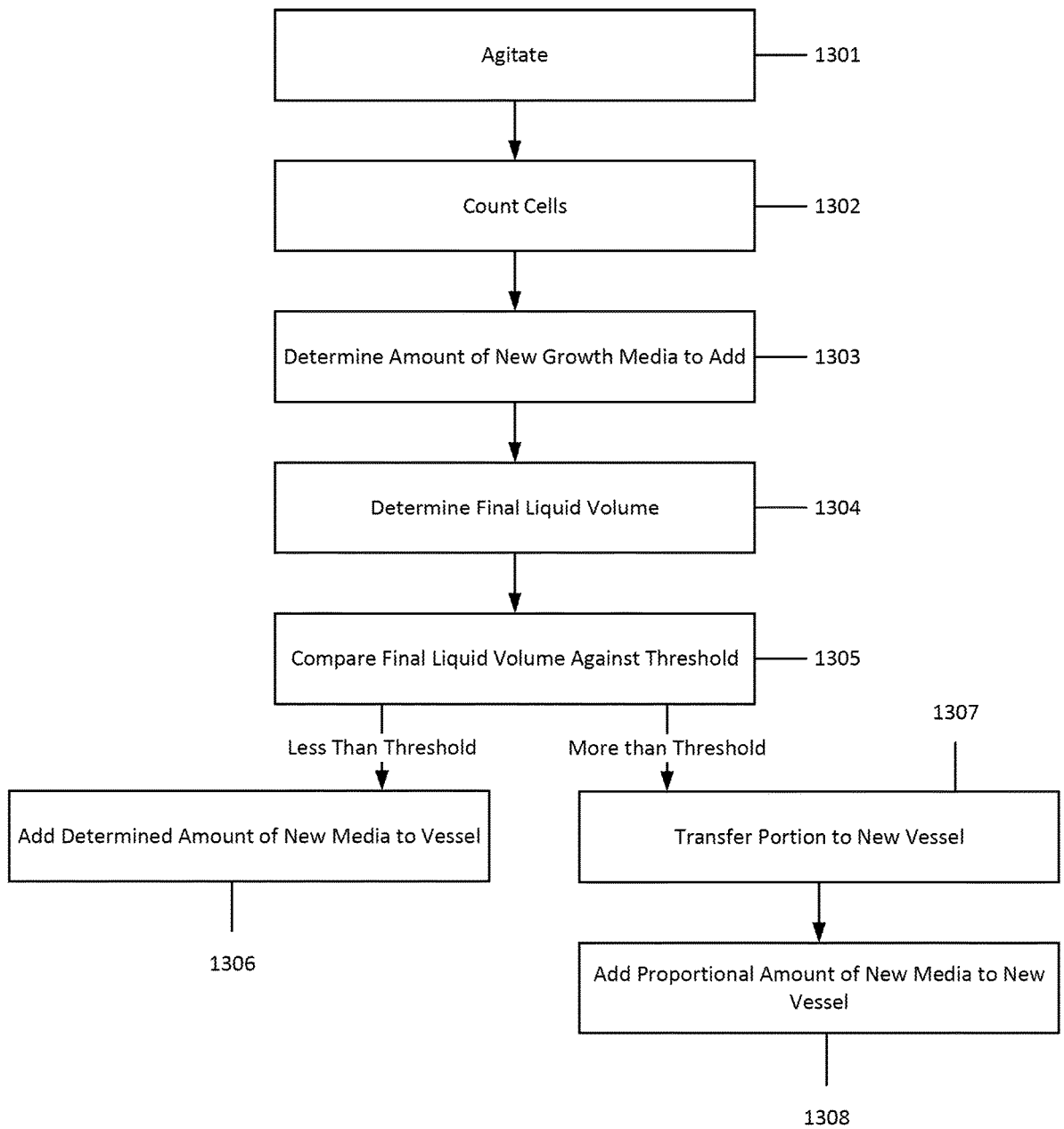
FIG. 13 illustrates the steps of a method for suspension cell line maintenance with optional passaging.

FIG. 13 illustrates the steps of a method for suspension cell line maintenance with optional passaging. At step 1301, a cell culture vessel may be agitated gently to evenly distribute the cells within the growth media in the vessel. Next, at step 1302, the cells within the vessel are counted and at step 1303 an optimal amount of new growth media is determined based on the cell count or the cell density. At step 1304, a final liquid volume of the cell culture vessel after adding the determined amount of new growth media is determined. Every time a procedure adds liquid to a cell culture vessel, the amount of liquid added is recorded and tallied by a controller. In this way, the controller maintains a current value for the amount of liquid in each cell culture vessel. At step 1305, the estimated final fluid volume of the cell culture vessel is compared against a configured maximum volume for the particular cell culture vessel being used. For example, the total volume of a vessel cannot exceed the total capacity of the vessel. In some embodiments, the threshold maximum volume may be significantly lower than the total volume of the vessel. If the estimated final fluid volume is lower than the configured threshold, at step 1306 the determined amount of new media is added to the vessel. If the estimated final fluid volume is greater than the configured threshold, the automated cell culture system may divide the contents of the cell culture vessel into two or more cell culture vessels to accommodate the estimated final fluid volume. In this example method, the contents of the cell culture vessel, referred to now as the first cell culture vessel, will be split between the first cell culture vessel and an additional second cell culture vessel. At step 1307, a portion of the contents of the first cell culture vessel may be transferred to the second cell culture vessel. The proportion of the contents of the first and second cell culture vessels is recorded by a controller. Then, at step 1308, a proportional amount of new cell culture growth media is added to each of the first and second cell culture vessels in proportion to the amount of the final liquid volume each contains. For example, if the fluid contents of the first cell culture vessel are evenly divided between the first cell culture vessel and the second cell culture vessel, new media will be similarly equally divided between the first and second cell culture vessels.

Figure 14:
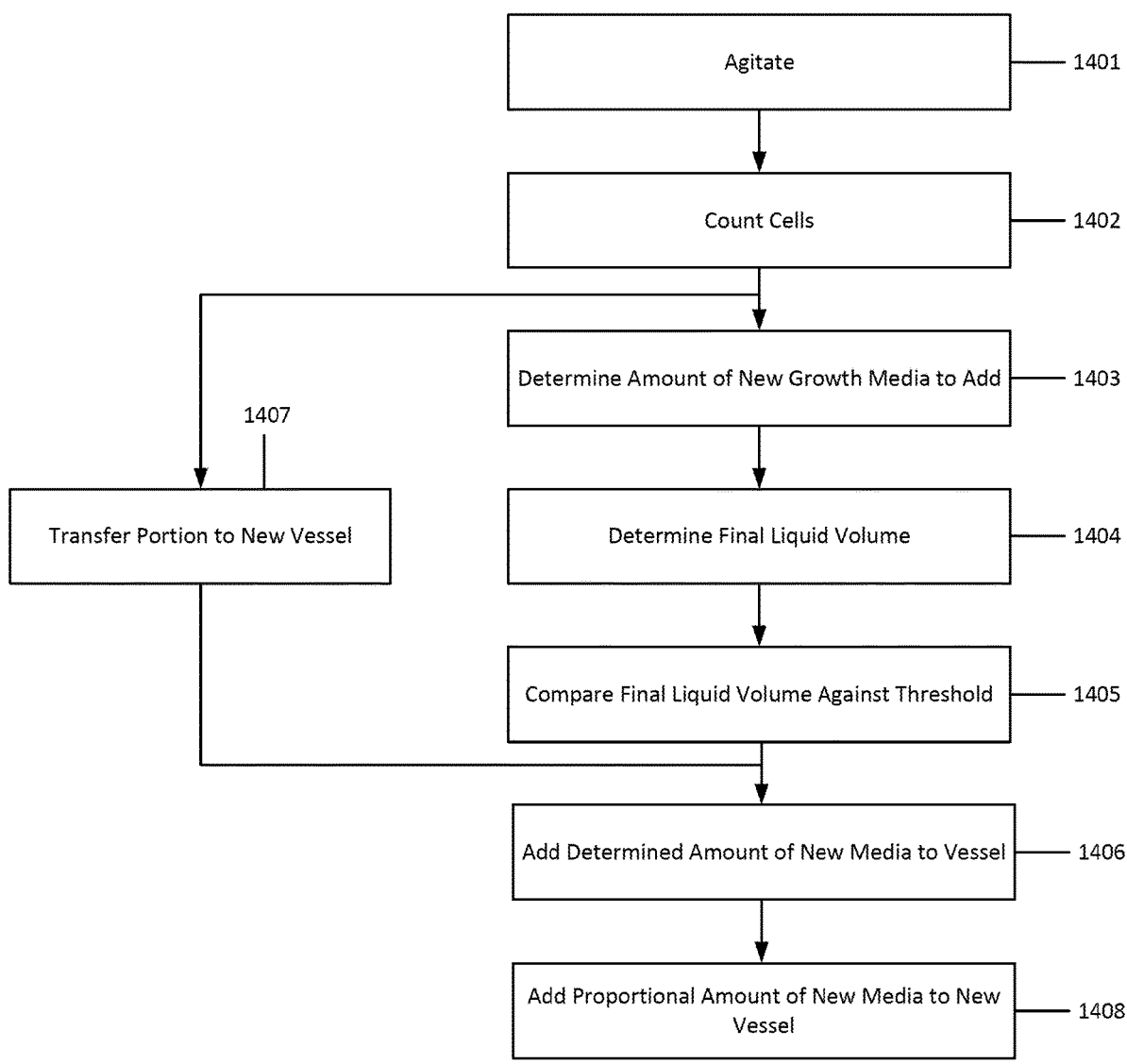
FIG. 14 illustrates the steps of a method for suspension cell line expansion.

FIG. 14 illustrates the steps of a method for suspension cell line expansion. The method for suspension cell line expansion mirrors that of suspension cell line maintenance, however at step 1407, the contents of the vessel may be transferred to new cell culture vessels even if the total volume remains below the total volume threshold for the cell culture vessel. That is, cells may be transferred to new cell culture vessels when appropriate for encouraging growth of cells rather than only in response to running out of volume in the cell culture vessels.

Figure 15:
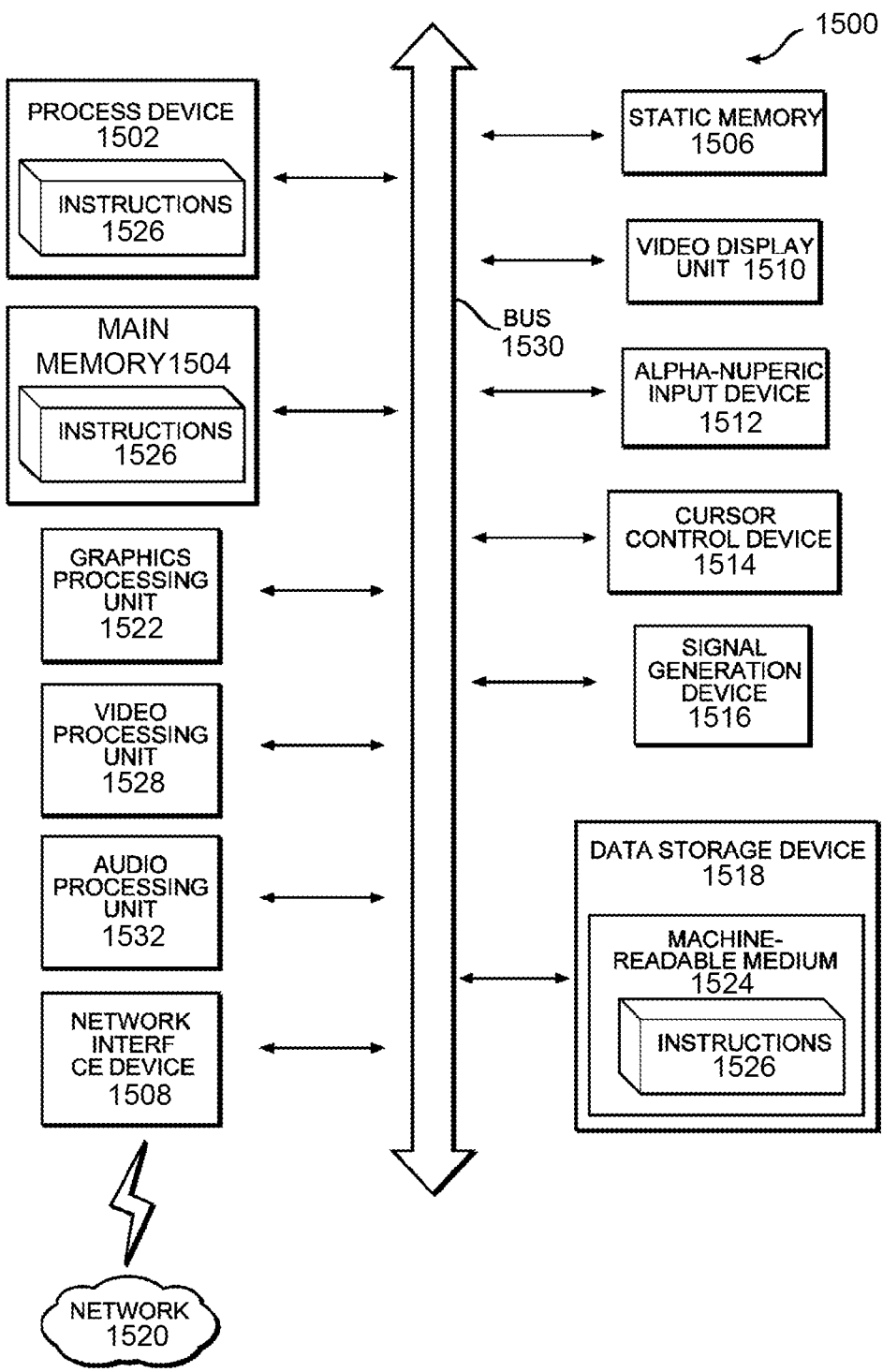
FIG. 15 illustrates an example machine of a computer system within which a set of instructions, for causing the machine to perform any one or more of the methodologies discussed herein, may be executed.

FIG. 15 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 1500 includes a processing device 1502, a main memory 1504 (e.g., read-only memory (ROM), flash memory; dynamic random access memory (DRAM) such as synchronous DRAM (SDRAM) or Rambus DRAM (RDRAM), etc.), a static memory 1506 (e.g., flash memory, static random access memory (SRAM), etc.), and a data storage device 1518, which communicate with each other via a bus 1530.

Processing device 1502 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 1502 may also be one or more special-purpose processing devices such as an application specific integrated circuit (ASIC), a field programmable gate array (FPGA), a digital signal processor (DSP), network processor, or the like. The processing device 1502 is configured to execute instructions 1526 for performing the operations and steps discussed herein.

The computer system 1500 may further include a network interface device 1508 to communicate over the network 1520. The computer system 1500 also may include a video display unit 1510 (e.g., a liquid crystal display (LCD) or a cathode ray tube (CRT)), an alphanumeric input device 1512 (e.g., a keyboard), a cursor control device 1515 (e.g., a mouse), a graphics processing unit 1522, a signal generation device 1516 (e.g., a speaker), graphics processing unit 1522, video processing unit 1528, and audio processing unit 1532.

The data storage device 1518 may include a machine-readable storage medium 1524 (also known as a computer-readable medium) on which is stored one or more sets of instructions or software 1526 embodying any one or more of the methodologies or functions described herein. The instructions 1526 may also reside, completely or at least partially, within the main memory 1504 and/or within the processing device 1502 during execution thereof by the computer system 1500, the main memory 1504 and the processing device 1502 also constituting machine-readable storage media.

In one implementation, the instructions 1526 include instructions to implement functionality corresponding to the components of a device to perform the disclosure herein. While the machine-readable storage medium 1524 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Figure 16A:
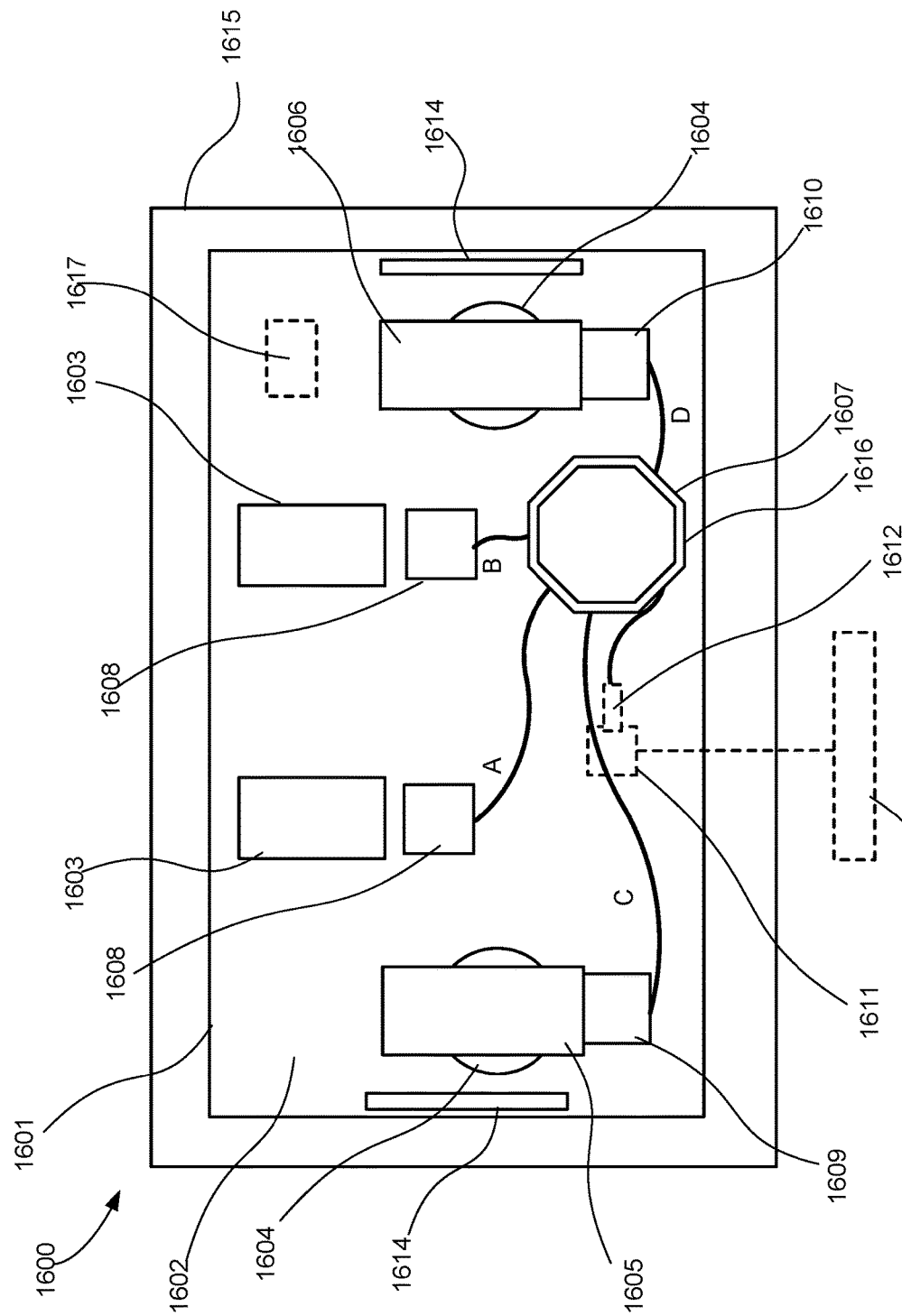
FIG. 16A is a schematic illustration of a tray assembly of a cell culturing system, according to an embodiment.
Figure 16B:
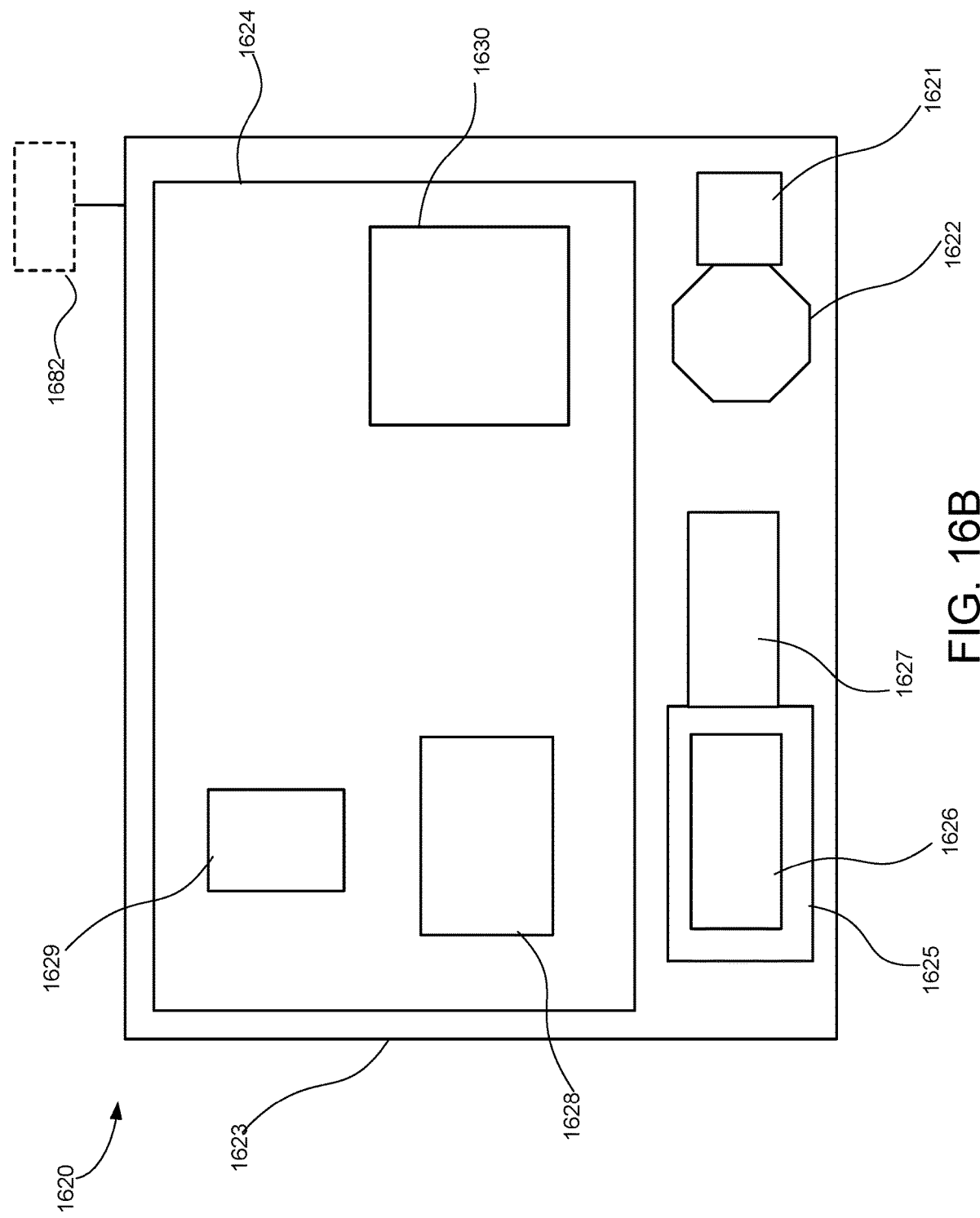
FIG. 16B is a schematic illustration of a base unit of a cell culturing system, according to an embodiment.
Figure 16C:
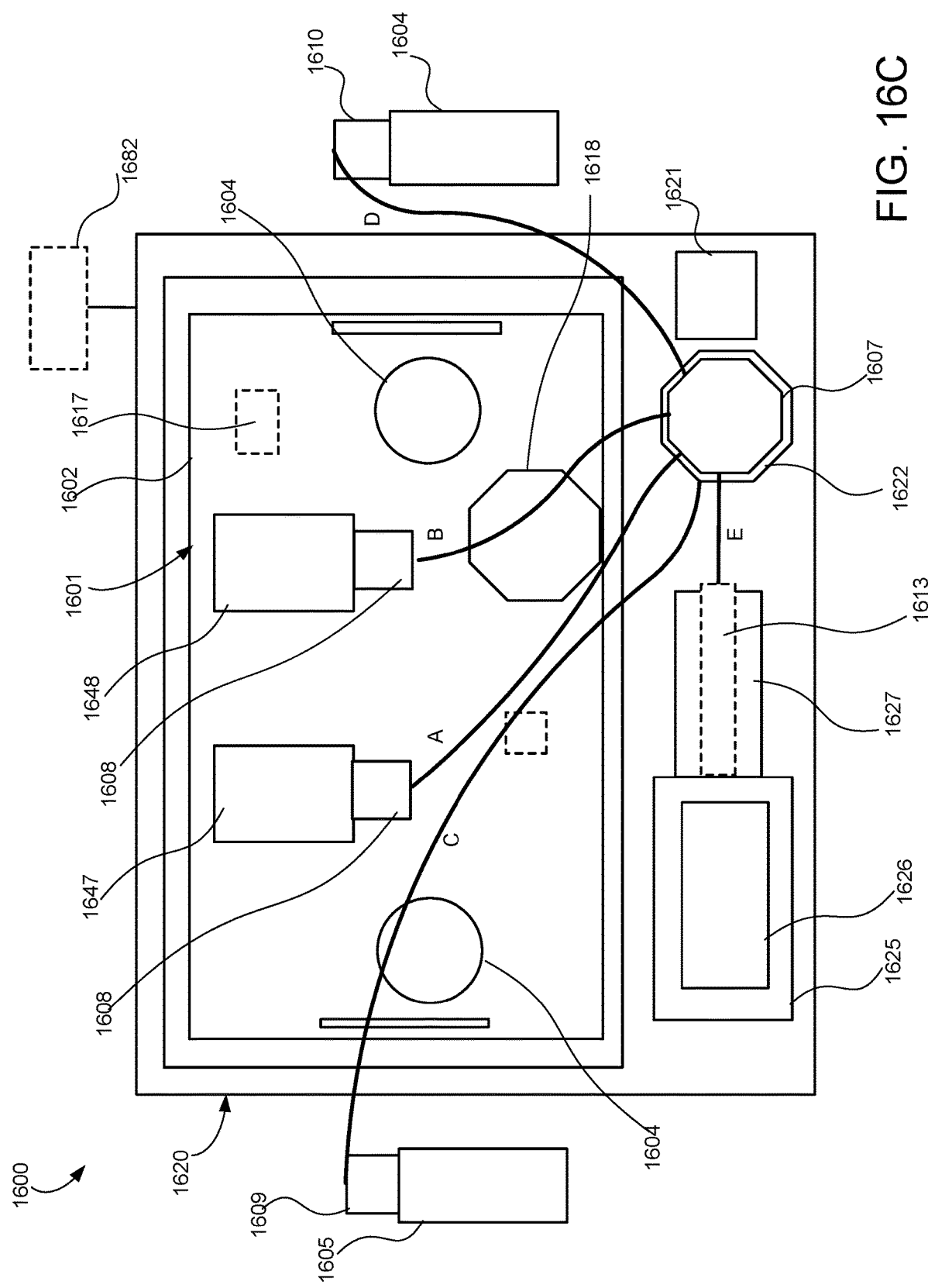
FIG. 16C is a schematic illustration of a cell culturing system, according to an embodiment, including the tray assembly shown in FIG. 16A and the base unit shown in FIG. 16B.

FIGS. 16A-16C illustrate a schematic view of an automated cell culture system according to another embodiment. This example automated cell culture system 1600 includes a consumable or disposable cell culture tray assembly 1601 (also referred to herein as "tray assembly," see FIG. 16A) and a reusable base unit 1620 (see FIG. 16B). The disposable tray assembly 1601 includes various components described below; some of which are preassembled on (or with) the tray assembly 1601 and enclosed within a protective overwrap to maintain the components in a sterile state. Some of the components of the tray assembly 1601 can be added to the tray assembly 1601 within an aseptic environment (e.g., a laminar flow hood) prior to using the tray assembly 1601 in a cell culturing procedure. When the tray assembly 1601 has been assembled and is ready for use, the tray assembly 1601 can be coupled to the base unit 1620 as described in more detail herein.

As shown in FIG. 16A, the tray assembly 1601, includes a tray 1602 that can be removably coupled to the base unit 1620 as described herein. In some embodiments, the tray 1602 can include one or more transparent or cut-out portions such that objects disposed on a top surface of the tray 1602 can be viewed from below the tray 1602. For example, as described in more detail below; the cell culture system 1600 can optionally include an imaging device and/or other sensors that are disposed in the base unit 1620 and below the tray 1602 when the tray assembly 1601 is coupled to the base unit 1620. The transparent portion(s) or cut-out(s) can allow for images and/or other data to be obtained through the transparent portion or cut-out, such as the contents of a cell culture container coupled to the tray 1602, as described in more detail below: In some embodiments, the tray assembly 1601 can include a cell counting chip 1617 shown in FIG. 16A. The cell counting chip 1617 can also include a bottom transparent portion and can be used to obtain information about the contents of a cell culture container as described below: In some embodiments, the cell counting chip 1617 may be coupled to or mounted within the base unit 1620 instead of being preassembled on the tray assembly 1601.

The tray assembly 1601 also includes one or more couplers 1603 that can be used to hold cell culture vessels or containers. The tray 1602 can optionally include holders 1604 that can be used to removably couple a reagent container 1605 and a waste container 1606 to the tray 1602 (e.g., to secure the containers during shipping, initial setup, or the like). Although two couplers 1603 are shown, in other embodiments, there could be only one or more than two couplers 1603. For example, in some embodiments a tray assembly can be configured to support only one cell culture container and thus includes only a single coupler 1603 that maintains the cell culture container in a fixed position on the tray. Similarly, although only one waste container 1606 and one reagent container 1605 are shown, in alternative embodiments, there can be multiple waste and reagent containers. Moreover, although FIG. 16A shows the waste container 1606 and the reagent container 1605 as being part of the tray assembly 1601, in other embodiments, the waste container 1606 and/or the reagent container 1605 can be separate components within the automated cell culture system 1600 that are not coupled to the tray 1602 during use. For example, in some embodiments, the reagent container 1605 can be used to contain cell culture media and can be placed in a refrigerated portion (not shown) of the automated cell culture system 1600 or another refrigeration location. The couplers 1603 and holders 1604 can be separate components attached to the tray 1602 or can be a component integrally or monolithically formed with the tray 1602. For example, in some embodiments, the couplers 1603 and/or the holders can include a deformable bracket, a movable pin, or any other suitable structure to couple the containers to the tray 1602. In some embodiments, the tray assembly 1602 can optionally include handles 1614 that can be used by a user to move and carry the tray assembly 1602. The handles 1614 can be separate components from the tray 1602 or formed integrally or monolithically with the tray 1602. In some embodiments, the tray assembly 1601 may not include holders 1604. In some embodiments, although not shown, the tray assembly 1601 can be preassembled with one or more cell culture containers.

The tray assembly 1601 also includes a multiport valve 1607 and one or more container lids 1608 (FIG. 16A shows two container lids 1608). The container lids 1608 can be coupled to the tray 1602 with disposable packaging mounts (not shown in FIGS. 16A-16C). The lids 1608 are each configured to be coupled to different cell culture container as described below: In this example embodiment, there are two lids 1608, but it should be understood that a different number of lids 1608 can be provided to accommodate a different number of cell culture containers. Each of the lids 1608 can include a liquid exchange port (also referred to herein as "fluid port") and a gas exchange port (each not shown in FIGS. 16A-16C). As shown, each of the fluid ports is coupled to a select port of the multiport valve 1607 with tubing (See tubing A, B, C and D in FIG. 16A). The gas exchange ports can allow gas transfer out of the cell culture container to which it is coupled. For example, in some embodiments, the lids 1608 can be similar to the cell culture vessel lid 803 or the lid 2408 shown and described herein. For example, the lids 1608 can include a gas filter that prevents microbes and/or contaminants from entering the cell culture container, thereby allow cell culturing and fluid transfer via lids 1608 while maintaining a closed (and/or sterile) system with other containers within the system (e.g., the reagent container 1605, the waste container 1606 or other containers). In some embodiments, the tray assembly can optionally include lids 1609 and 1610 that are coupled to the reagent container 1603 and the waste container 1606, respectively. The lid 1609 and/or the lid 1610 can be similar in structure and function as the lid 1608 and/or the cell culture vessel lid 803.

The multiport valve 1607 can include the same or similar components and functions in the same or similar manner as the multiport valves described above for previous embodiments (e.g., the multiport valve 600 or the multiport valve 2407 described herein). The multiport valve 1607 can include a master port configured to be coupled to a fluid pump 1613 of the base unit (described below and shown in FIGS. 16B and 16C), and multiple selectable ports that can be fluidically coupled to liquid exchange ports of the lids 1608, 1609, 1610 and/or other components of the cell culture assembly 1600 as described herein. For example, one port of the selectable ports can be aseptically and/or fluidically coupled to a first liquid exchange port of a first lid 1608, and a second selectable port can be aseptically and/or fluidically coupled to a second liquid exchange port of a second lid 1608. In some embodiments, a third port of the multiport valve 1607 can be coupled to the liquid exchange port of the reagent container 1605, a fourth port can be coupled to the liquid exchange port of the waste container 1606 and a fifth port can be coupled to a liquid exchange port of a cell harvest container (not shown in FIGS. 16A-16C). The multiport valve 1607 can be coupled to various other components, such as, for example, a cell counting chip, cell harvest container(s), various reagent and enzyme containers, etc. An example system schematic illustrating some example couplings of a multiport valve is provided in FIG. 59. In this manner, when actuated the multiport valve 1607 can facilitate fluid exchange between various containers within the automated cell culture system 1600. For example, as described herein, the multiport valve 1607 can be actuated to facilitate the addition of cell culturing media or reagents to the cell culture containers, the removal of cells from the cell culture containers (e.g., cell passaging or cell harvesting), or any other fluid movement associated with cell culturing.

The multiport valve 1607 can be preassembled and coupled to the lids 1608, 1609, 1610 on the tray assembly 1601 and enclosed within the protective overwrap 1615. This arrangement allows the end user to receive the prepackaged tray assembly 1601 within the protective overwrap. In some embodiments, tray assembly 1601 can be sterilized prior to being placed in the protective overwrap. As described herein, the user can then load the desired cells, reagents, cell culture media, or the like into the containers and can couple the pre-connected lids to the containers within an aseptic environment. The tray assembly 1601 can then be coupled to the base unit and moved into an incubation environment where fluid exchange can be performed to ensure the desired cell culturing, as described herein.

The multiport valve 1607 is configured to engage a valve actuator 1621 of the base unit 1620. The multiport valve 1607 can include a mounting portion 1616 configured to matingly couple to a valve connector 1622 of the base unit 1620 in some embodiments. For example, the mounting portion 1616 can have a shape such that it can be coupled to the valve connector 1622 in a puzzle-like manner. Examples of such a mounting portion and valve connector are described below with reference to particular embodiments. As shown in FIGS. 16B and 16C, when the multiport valve 1607 is engaged to the valve actuator 1621 of the base unit 1620, the valve actuator 1621 can actuate the multiport valve 1607 to move to a selected port to allow for selective fluid transfer to and from the various containers of the tray assembly 1601 and cell culture containers (described below). In some embodiments, the multiport valve 1607 can be coupled to the valve actuator 1621 while remaining coupled to the tray 1602. For example, a valve connector (not shown) coupled to the valve actuator 1621 can be disposed on the base unit 1620 below where the tray assembly 1602 is removably coupled to the base unit 1620 (e.g., similar to the base unit 301 or the base unit 2120 described herein). In some embodiments, the multiport valve 1607 can be removed from the tray 1602 (while remaining coupled to the lids, thereby preserving the closed system) and attached to the mating valve connector 1622 of the base unit 1620 as shown, for example, in FIGS. 16B and 16C. FIG. 16B shows the connector 1622 without the multiport valve 1607 coupled thereto, and FIG. 16C shows the multiport valve 1607 coupled thereto. In other words, the multiport valve 1607 can be detached from a mating mounting pocket 1618 (see FIG. 16C) of the tray 1602 and attached to the valve connector 1622 of the base unit 1620. As described above, the mounting portion 1616 of the valve 1607 is shaped to matingly engage the mounting pocket 1618 and to matingly engage the valve connector 1622 of the base unit 1620 to ensure proper positioning and alignment within both the tray assembly 1601 and the base unit 1620. This relocation of the multiport valve 1607 can be done with the lids 1608, 1609, 1610 remaining aseptically coupled to the multiport valve 1607. Removing the valve 1607 from the tray 1602 allows the interface between the valve 1607 and the valve actuator 1621 to be stationary, which is well-suited for those embodiments that include an agitator to move the tray 1602 relative to the base unit 1620. Similarly stated, by coupling the valve 1607 directly to the base unit 1620, the interface between the valve 1607 and the valve actuator 1621 is not disrupted by the relative movement between the tray 1601 and the base unit 1620.

Also shown in FIG. 16A is an optional pump holder 1611, that can be used to hold a port connector 1612 that is fluidically coupled to the master port of the multiport valve 1607. This port is used to connect the fluid pump 1613 to the tray fluidics 1602 during preparation of the tray assembly 1601 for a cell culturing procedure. The fluid pump 1613 can be used produce fluid movement in the cell culture system 1600 as described herein. The fluid pump 1613 can be any suitable pump that produces pressure and/or flow within the cell culture system 1600. For example, the fluid pump 1613 can be a syringe that includes a piston rod and a syringe body. The syringe is only one example of a type of fluid pump that can be used in the cell culture system 1600. Various other positive displacement fluid pumps can be used, such as, for example, a peristaltic pump. In some embodiments, the pump can be a single-port pump, whereas in other embodiments, the pump can be a two-port pump, as described herein. When a syringe is used as the pump 1613, it can be attached to the multiport valve 1607 and to the optional syringe holder 1611 in an aseptic environment prior to a cell culturing procedure.

The base unit 1620 (see FIGS. 16B and 16C) includes a housing 1623 that supports various components of the base unit 1620 and can define (or include) a receiving portion 1624 to receive and removably couple the tray assembly 1601 thereto. In some embodiments, the receiving portion 1624 can include an opening in which the tray assembly 1601 can be placed and supported by a tray support (not shown). In some embodiments, the tray assembly 1601 is supported by a support portion of the base unit 1620 such that the tray assembly 1601 is elevated above a top surface of the base unit 1620. In some embodiments, the tray assembly 1601 is supported at least in part by engagement with an agitator (described below) of the base unit 1620. In some embodiments, the tray assembly 1601 can be removably coupled to a separate support member that is couplable to the housing 1623 of the base unit 1620. The base unit 1620 can also include one or more transparent portions or open portions corresponding to transparent portions of the tray 1602 such that images and/or other sensor data associated with the contents of the cell culture containers can be obtained.

The base unit 1620 includes the valve connector 1622 and valve actuator 1621 described above and also includes a fluid pump portion 1627 and a pump actuator 1626. The pump actuator 1626 can be disposed, for example, at least partially within an opening 1625 defined by the housing 1623. As described above, in some embodiments, the fluid pump 1613 can be a syringe or other type of positive displacement fluid pump that is fluidically coupled to the multiport valve 1607 and then coupled to the fluid pump portion 1627 of the base unit 1620. In some embodiments, in which a syringe is the fluid pump 1613, the fluid pump portion 1627 can include a holder (not shown in FIGS. 16A-16C) that can be used to hold and support the syringe 1613 on the housing 1623. The holder can be a separate component or a component formed integrally or monolithically with the housing 1623. The fluid pump 1613 can be fluidically coupled to the master port of the multiport valve 1607. In this example embodiment, as shown in FIG. 16C (showing the tray assembly 1601 coupled to the base unit 1620), the multiport valve 1607 is shown detached from the tray assembly 1601 and coupled to the valve connector 1622 and the fluid pump 1613 is coupled to the master port with tubing E. The fluid pump 1613 can include a movable member within a pump body (not shown in FIGS. 16B and 16C). During operation of the system 1600, the movable member of the fluid pump 1613 (e.g., plunger, rotor) can be actuated to cause a suction force to bring fluid into the pump body and can actuate the movable member to push fluid out of the pump body as described above for previous embodiments.

In some embodiments, the base unit 1620 can also include an agitator 1628. The agitator 1628 can include, for example, an orbital shaker that moves the tray 1602 in a circular or half-circular motion. The agitator 1628 can be configured to agitate the removable tray assembly 1601 in relation to the housing 1623 as described above for previous embodiments. The agitator 1628 may agitate the tray 1602 in a rocking motion, vibrating motion, circular swirling motion, or other motions useful in cell culturing. In some embodiments, individual cell culture vessels/containers may be independently agitated by independent agitators displaced between the cell culture vessel and the removable tray assembly 1601 as previously described. In some embodiments, an agitator may not be included.

In some embodiments, the base unit 1620 can also optionally include one or sensors 1629 (only one shown in FIGS. 16B and 16C) and an electronic control system 1630 to control the operation of any of the components of the cell culture system 1600 (e.g., the valve actuator 1621, the pump actuator 1626). The electronic control system 1630 can optionally be incorporated within, coupled to, or provided by a remote computing system, such as, for example, within a cloud computing environment. In some embodiments, the sensor(s) 1629 can be mounted to a device to allow for the sensor(s) to be movable relative to the housing 1623 of the base unit 1620. An example of such an embodiment is described below with reference to FIGS. 32-34. The sensors 1629 can include, for example, one or more imaging devices, a microscope, a color monitor or any other type of sensor as described herein. The sensor(s) can be used to capture images or other types of output that can be used to determine obtain information about the contents within a cell culture container (e.g., 1647, 1648), such as, for example, the density of the contents to determine a quantity of cells within the container (for example, for suspension cells) during a cell culturing procedure, or a percentage confluence (i.e., percentage of coverage of the container area with cells) in the case of, for example, adherent cells. In some embodiments, the sensor(s) 1629 can be used to capture images and/or other types of output of a sample portion of the contents of a cell culture container via the cell counting chip 1617. For example, a sample of the fluid mixture within a cell culture container can be extracted into the cell counting chip 1617, and a sensor 1629 can be moved to a position in alignment with the cell counting chip 1617 and used to image or otherwise collect information associated with the sample fluid mixture on the cell counting chip 1617. In some embodiments, the sensor(s) 1629 can be operatively coupled to or incorporated within the electronic control system 1630.

As described above, in some embodiments, a light or light source 1682 (see FIGS. 16B and 16C) can also be provided that can be used in combination with, for example, an imaging device. In some embodiments the light can be movable with respect to the housing of the base unit 1620. For example, a light source can be mounted above the tray assembly 1601 of the system on a movable multi-axis gantry, which allows it to be controlled to move to the same position as the microscope within the base unit. In some embodiments, the light source can be operatively coupled to the same gantry as the imaging device such that the imaging device and light source can be moved together. In some embodiments, the system 1600 may include one or more cameras or pairs of LEDs and light sensors to image the contents of cell culture containers.

In some embodiments, the sensor(s) 1629 can include a valve position sensor configured to produce a valve position signal associated with a rotation position of the valve actuator. In this manner the valve position sensor can detect which of the selectable ports is fluidically coupled to the master port (e.g., the fluid pump 1613). In some embodiments, the sensor(s) 1629 can include a pump position sensor configured to produce a pump position signal associated with the movement of the pump. In this manner, the pump position sensor can indicate the travel of the pump and/or the volume of the fluid moved by the pump. As described herein, the electronic control system 1630 can determine, based on the pump position signal, an estimated amount of fluid within (or being added to) one of the cell culture containers.

Figure 17:
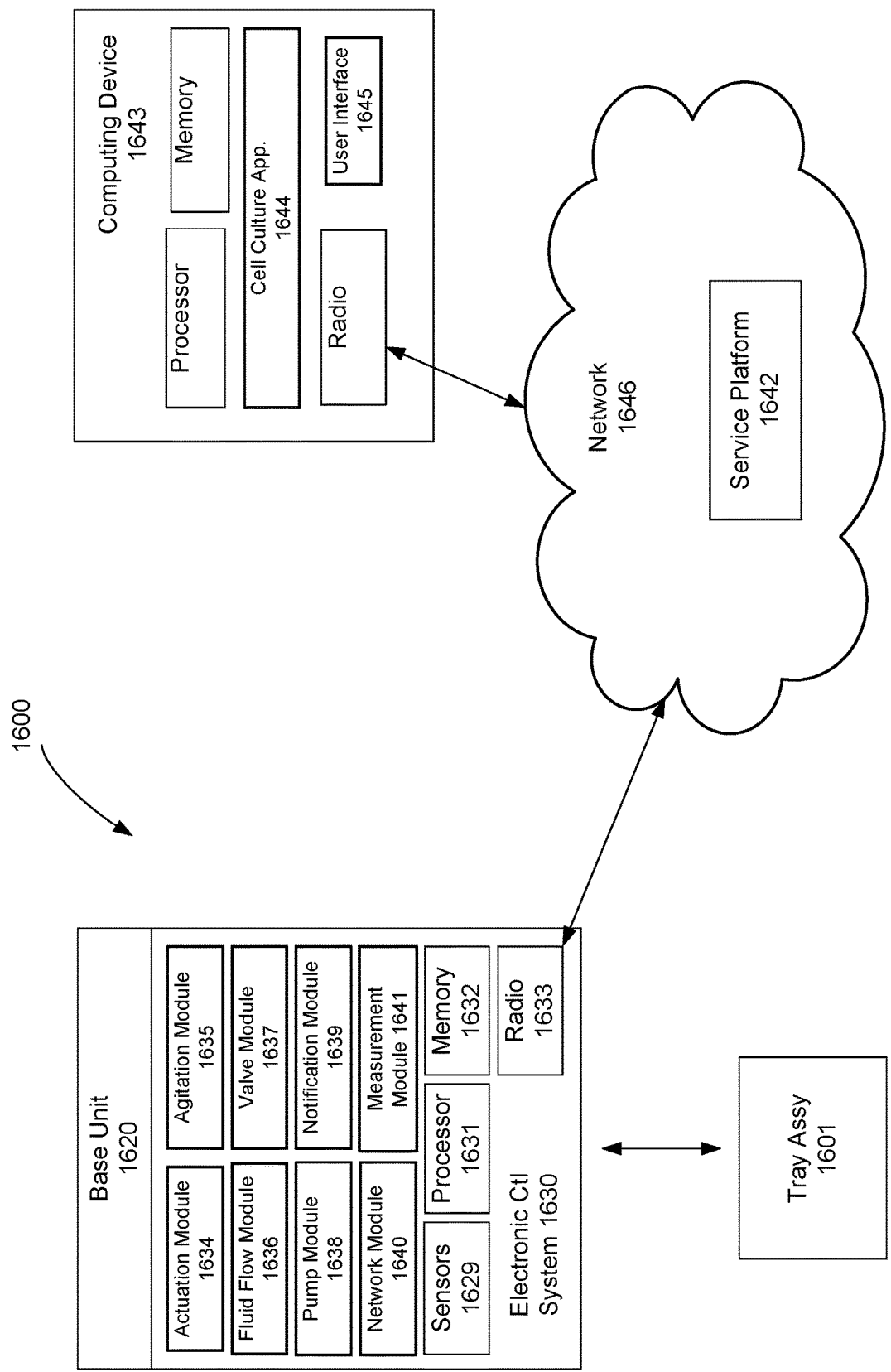
FIG. 17 is a schematic illustration of an electronic control system of a cell culturing system, according to an embodiment.

FIG. 17 is a schematic illustration of the electronic control system 1630 that can be used to control operation of the cell culture system. The components and architecture of the electronic control system 1630 are provided as an example, and in some embodiments, the electronic control system 1630 (or any of the electronic control systems described herein) can include different components than those shown in FIG. 17. Moreover, in some embodiments, a base unit and/or a cell culturing assembly need not include the electronic control system as described in FIG. 17. For example, in some embodiments, the base unit 1620 (or any of the base units described herein can include the computer system 1500 described herein). In other embodiments, the base unit 1620 need not include an electronic control system.

As shown in FIG. 17, the electronic control system 1630 includes one or more processor 1631, one or more memory component 1632, a radio 1633 and various modules, such as an actuation module 1634, an agitation module 1635, a fluid flow module 1636, a valve module 1637, a pump module 1638, a measurement module 1641 (also referred to as a cell sensor module) and/or a network module 1640. Although FIG. 17 illustrates the electronic control system 1630 being within the base unit 1620, as described above, the electronic control system 1630 or portions thereof can be provided outside of the base unit 1620 (e.g., within a cloud computing environment). The electronic control system 1630 can automatically control the fluid flow into and out of the various containers through actuation of, for example, the pump actuator 1626 and the valve actuator 1621. The electronic control system 1630 can also automatically control the actuation of the agitator 1628, the sensor(s) 1629, and the valve actuator 1621. Operation and actuation of the fluid pump 1613, valve actuator 1621, selection of ports on the multiport valve 1607, etc. can be the same as or similar to operation of these components as described above for previous embodiments. As described above for previous embodiments, in operation, the combination of fluid pumps, valves of the multiport valve, containers, and cell culture vessels may be used to transfer liquids to and from the cell culture vessels and the containers.

During preparation for a cell culturing procedure, the tray assembly 1601 can be placed in an aseptic environment (e.g., a laminar flow hood) and the overwrap 1615 can be removed. While in the aseptic environment (e.g., the flow hood), cell culture vessels or containers 1617, 1618 can be prepared (e.g., cells and reagent added to the containers), secured to the lids 1608 and placed within the couplers 1603 on the tray 1602. The cell culture containers 1617, 1618 can be any known type cell culture vessel, such as, for example, a flask or dish as described above for previous embodiments. The waste container 1606 and the reagent container 1605 can be placed in an upright position within the holders 1604. In other embodiments, the waste container 1606 and/or the reagent container 1605 can be placed in any suitable location for transportation within other locations of the cell culturing system 1600.

The tray assembly 1601 can then be coupled to the base unit 1620 as shown in FIG. 16C. In this embodiment, the multiport valve 1607 is decoupled from the tray assembly 1601 and matingly coupled to the valve actuator 1621, while remaining fluidically coupled to the various lids 1608, 1609, 1610. The fluid pump 1613 can be fluidically coupled to the multiport valve 1607 via a length of tubing E. In the case of a syringe being used as the fluid pump 1613, as described above, the syringe can be coupled to the multiport valve 1607 within the aseptic environment and coupled to the tray 1602 prior to the tray assembly 1601 being coupled to the base unit 1620. The syringe 1613 can then be moved to the holder (not shown) of the base unit 1620 and coupled to the pump actuator 1626, while remaining fluidically coupled to the multiport valve 1607 via tubing. The waste container 1606 and the reagent container 1605 can be removed from the tray 1602 and placed, for example, at a location alongside or near the tray 1602, and/or within the incubator, or a refrigerator. A more detailed description of the method of preparing the cell culture system 1600 for use is described below with reference to FIGS. 21-30. The tray assembly 1601 can be coupled to the base unit 1620, within the aseptic environment or outside of the aseptic environment. The cell culture system (with tray assembly 1601 coupled to the base unit 1620) can be placed in an incubator ready for a cell culturing procedure. In some embodiments, the tray assembly 1601 can be coupled to the base unit 1620 within the incubator.

Any of the base units and/or tray assemblies described herein can be used to perform any of the computer-implemented methods described herein. Said another way, any of the base units and/or tray assemblies described herein can include (or interface with) an electronic control system to facilitate automated (or semi-automated) method of culturing cells. As shown in FIG. 17, the electronic computer system 1630 can communicate with other remote computing devices (e.g., computing device 1643), via a network 1646 (e.g., the Internet), through, for example, a service platform 1642 and a cell culture Application (i.e., App) 1644. The electronic control system 1630 can in addition to, or alternatively, communicate with a remote computing device through a direct connection such as, a cable connected to a USB port of the base unit 1620. The components, modules, and/or functions described in connection with the cell culturing system 1600 can be included within any of the cell culturing systems described herein. For example, although not shown, the cell culturing systems 200, 300 and 400 can include an electronic control system similar to or the same as the electronic control system 1630. Moreover, although the cell culturing system 1600 is shown and described as including only one connected computing device 1643, in other embodiments, the cell culturing system 1600 (and any of the cell culturing systems described herein) can include any number of any of connected remote computing devices.

The service platform 1642 can be any suitable computer-implemented interface and/or computing entity, such as a server or personal computer, that is configured to communicate via the network 1646 with the remote computing device 1643 and/or any other portions of the cell culturing system 1600 (e.g., a call center interface, other remote computing devices, or the like, not shown). More specifically, the service platform 1642 can receive information from the devices within the cell culturing system 1600 (e.g., base units or remote computing devices) manipulate the information and produce information to any other devices within the cell culturing system 1600. For example, in some embodiments, cell density or cell confluence information associated with the tray assembly 1601 can be transmitted from the base unit 1620 to the remote computing device 1643. The remote computing device 1643 can produce notifications for the user via the cell culture application 1644 and can receive input from a user in response to such notifications. The remote computing device 1643 can then transmit the input (or instructions) to the service platform 1642. Based on the user input, the service platform 1642 can transmit instructions to the base unit 1620, which can then execute the instructions to perform the desired task (e.g., cell passaging). In this manner, the service platform 1642 can control and/or manage certain instructions, notifications and/or features. Similarly stated, in this manner the service platform 1642 can function as the "back end" for the cell culturing system 1600.

The network 1646 can be a piconet, the Internet, an intranet, a local area network (LAN), a wide area network (WAN), a virtual network, a telecommunications network, any other suitable communication system and/or combination of such networks. The network 1646 can be implemented as a wired and/or wireless network. The base unit 1620 and the remote computing device 1643 can be coupled to (or connected with) the network via any suitable mechanism and/or by any protocol. For example, in some embodiments, the base unit 1620 can be in direct communication with the network 1646, the remote computing devices 1643 and/or the service platform 1642 via the LTE Direct protocol or any other suitable protocol (e.g., the 5G mobile wireless standard based on the IEEE 802.11ac standard for broadband technology).

Although FIG. 17 identifies the base unit 1620, the electronic control system 1630 can be incorporated into (or used with) any of the base units described herein. As described above, the base unit 1620 includes or is attached to an electronic control system 1630. For example, in some embodiments, the electronic control system 1630 can be coupled to and/or within a housing 1623 and/or any other portion of the base unit 1620. Similarly stated, the electronic control system 1630 can be integrated within the base unit 1620. In other embodiments, however, the electronic control system 1630 can be separate from but operably coupled to the base unit 1620 (e.g., connected wirelessly or via a wired connection). Although the electronic control system 1630 is shown as including one or more processors 1631, one or more memory components 1632, a radio 1633 and various modules, such as an actuation module 1634, an agitation module 1635, a fluid flow module 1636, a valve module 1637, a pump module 1638, a measurement module and/or a network module 1640, in other embodiments, an electronic circuit system need not include all (or any) of these modules, and can include any other modules described herein. For example, in some embodiments, an electronic control system may only include a flow module and is configured to perform the cell passaging and flow methods associated therewith, and need not include, for example, the agitation module.

The processor 1631, and any of the processors described herein can be any suitable processor for performing the methods described herein. In some embodiments, processor 1631 can be configured to run and/or execute application modules, processes and/or functions associated with the cell culturing system 1600. For example, the processor 1631 can be configured to run and/or execute the actuation module 1634, the agitation module 1635 and/or the network module 1640 and/or any of the other modules described herein, and perform the methods associated therewith. The processor 1631 can be, for example, a Field Programmable Gate Array (FPGA), an Application Specific Integrated Circuit (ASIC), a Digital Signal Processor (DSP), and/or the like. The processor 1631 can be configured to retrieve data from and/or write data to memory, e.g., the memory 1632. As described herein, in some embodiments, the processor 1631 can cooperatively function with the radio 1633 and/or execute instructions from code to provide signals to communicatively couple the electronic control system 1630 to the computing device 1643 (e.g., via wireless communication) and/or any other computing entity via a network such as network 1646. In some embodiments, the processor 1631 is a Bluetooth® low energy (BLE) processor.

The memory 1632 can be, for example, random access memory (RAM), memory buffers, hard drives, databases, erasable programmable read only memory (EPROMs), electrically erasable programmable read only memory (EE-PROMs), read only memory (ROM), flash memory, hard disks, floppy disks, cloud storage, and/or so forth. In some embodiments, the memory 1632 stores instructions to cause the processor 1631 to execute modules, processes and/or functions associated with such cell culturing system 1600 and/or the base unit 1620. For example, the memory 1632 can store instructions to cause the processor 1631 to execute any of the application modules described herein, and perform the methods associated therewith.

As described above, one or more of the sensor(s) 1629 can be separate and/or included within the electronic control system 1630 can include, for example, imaging devices, optical sensors, accelerometers, temperature sensors, contact sensors, position sensors and/or any other suitable input device. In some embodiments, the sensor(s) 1629 can include a sensor operable to monitor and/or measure the position (or selection) of the ports of the multiport valve 1607, the fluid pump 1627 position, temperatures, agitation, etc. For example, in some embodiments, a sensor 1629 can include a position sensor operable to detect a position of a multiport valve of the system. As yet another example, the sensor 1629 can include an optical sensor operable to detect the density (or amount) of cells within a cell culture container coupled to the tray 1602. In such embodiments, the optical sensor could detect the attenuation of light (e.g., to detect the density of cells within a light path). The optical sensor could alternatively capture an image (e.g., via a photocell, microscope, charge coupled device or the like) to determine the amount of cells within the cell culture container. As yet another example, a sensor 1629 can include an accelerometer operable to detect a characteristic movement or vibration signature of the tray assembly 1601 when the device is being agitated.

The radio 1633 (also referred to as a receiver, transmitter and/or transceiver) can be operable to send signals to, and/or receive radio signals, such as Bluetooth®, ZigBee, Wi-Fi, 1631 is Bluetooth® processor, the radio 1633 can be integral with the processor 1631. In other embodiments, the radio 1633 can include a processor distinct from the processor 1631. The radio 1633 can be operable to communicatively couple the electronic control system 1630 to the computing device 1643 and/or any other computing entity via a network 1646. The radio 1633 can include or be coupled to a ceramic chip antenna, a stamped antenna, a sintered antenna, a PCB conductive trace antenna, and/or any other suitable antenna.

The measurement module 1641 (also referred to in some embodiments as the cell sensor module) can be a hardware and/or software module (stored in memory 1632 and/or executed in the processor 1631). As described in more detail herein, in some embodiments, the measurement module 1641 is configured to receive multiple different signals from the sensors 1629 of the electronic control system 1630 and produce information to various other modules within the electronic control system 1630.

The flow module 1636 can be a hardware and/or software module (stored in memory 1632 and/or executed in the processor 1631). As described in more detail herein, the flow module 1636 can be configured to receive an indication (e.g., from the sensor(s) 1629) and/or transition information associated with a change in status of a pump or a multiport valve of the base unit 1620 and determine, based on the indication or the transition information, what valves of the multiport valve 1607 to open and close to cause fluid to move into and/or out of a particular container of the system 1600.

The network module 1640 can be a hardware and/or software module (stored in memory 1632 and/or executed in the processor 1631). The network module 1640 is configured to exchange information associated with the base unit 1620 and the remote computing device 1643 to facilitate the communication process. For example, the network module 1640 of the base unit 1620 can cause the remote computing device 1643 and the base unit 1620 to exchange short term and/or long-term security keys to complete the pairing and bonding process.

A notification module 1639 can be a hardware and/or software module (stored in memory 1632 and/or executed in the processor 1631). The notification module 1639 is configured to produce notifications associated with any of the methods and/or application modules described herein. For example, in some embodiments, the notification module 1639 can produce a notification that is transmitted via the radio 1633 and is for receipt by a notification module of the remote computing device 1643. In this manner, the notification module 1639 executed in the cell culture application can produce outputs (e.g., wireless communication signals, GUI elements, audible outputs, visual outputs, or the like) to notify the user of events.

The agitation module 1635, the valve module 1637, and the pump module 1638 can each be a hardware and/or software module (stored in memory 1632 and/or executed in the processor 1631). These modules can be configured to receive an indication (e.g., from the sensor(s) 1629) and/or transition information associated with a change in status of, for example, a pump or a multiport valve of the base unit 1620, and determine, based on the indication or the transition information, what actions to perform at the particular device (e.g., pump, valve, agitator). In some embodiments, the valve module 1637 and/or the pump module 1638 can provide information associated with a position of the multiport valve 1607 and the pump 1627, respectively. In some embodiments, the modules 1637 and 1638 can include (or receive information from) an encoder. In some embodiments, an actuator module 1634 can perform some or all of the functions of the agitation module 1635, valve module 1637, and/or pump module 1638.

The computing device 1643 (or other "remote" computing devices, such as a mobile computing entity, such as a smart mobile phone (e.g., an iPhone®, an Android® device, a Windows® phone, a Blackberry® phone, etc.), a tablet computer (e.g., an Apple iPad®, a Samsung Nexus® device, a Microsoft Surface® device, etc.), or a computer (e.g., a laptop, desktop, smart TV, etc.), and/or any other suitable computing entity. The computing device 1643 can include a processor, a memory, a user interface 1645, and a radio.

The user interface 1645 of the remote computing device 1643 can be, for example, a monitor or screen that displays visual elements to a user. The user interface 1645 can be a touch screen (of a smart mobile phone) upon which a series of graphical user interface (GUI) elements (e.g., windows, icons, input prompts, graphical buttons, data displays, notification, or the like) can be displayed. In some embodiments, the graphical user interface elements (see e.g., the GUI elements 1645A, 1645B, and 1645C described with reference to FIGS. 18-20) are produced by the cell culture application 1644. Moreover, the user interface can also receive input from the user, such as, for example, input via a touch screen, input via a microphone, or the like.

Figures 18, 19:
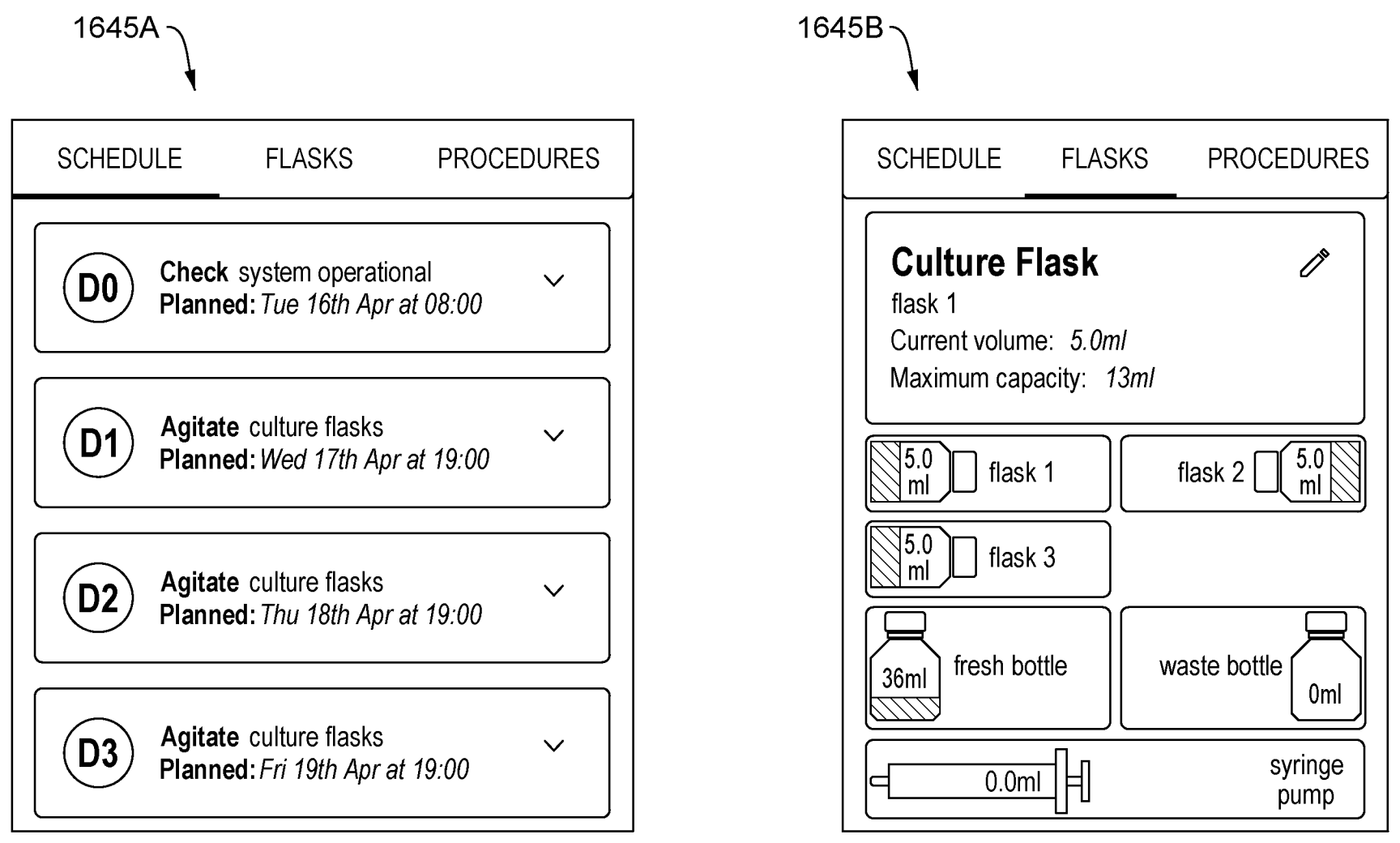
Figure 20:
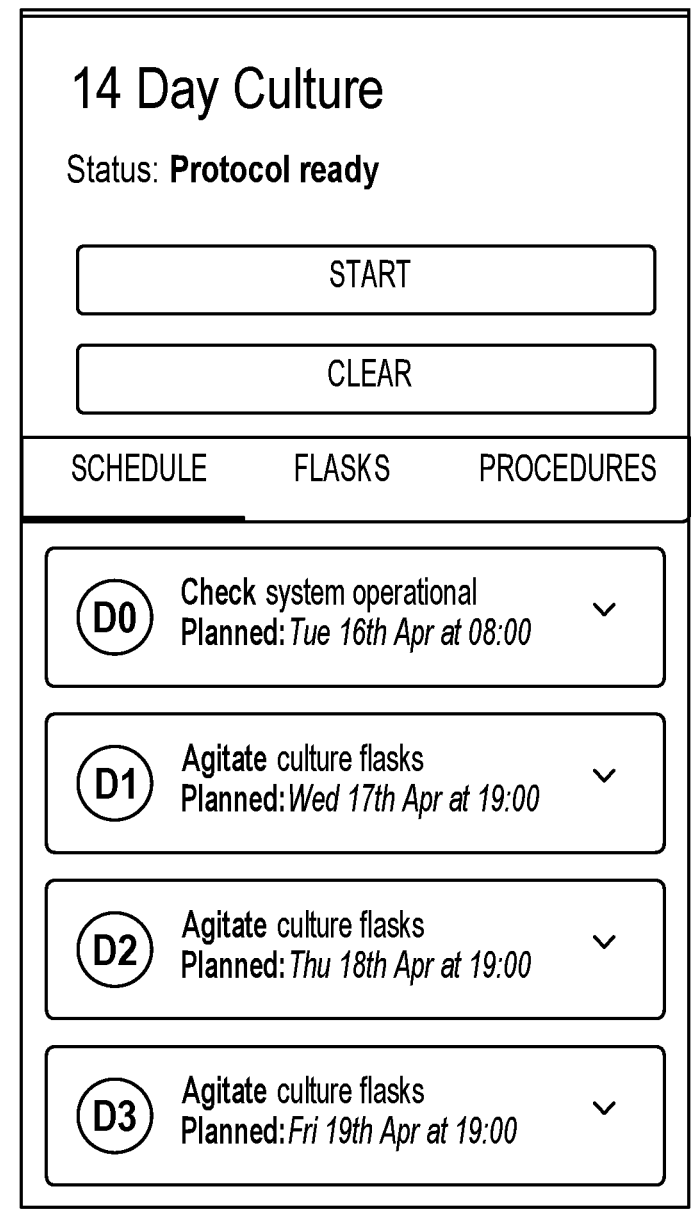
Figure 21:
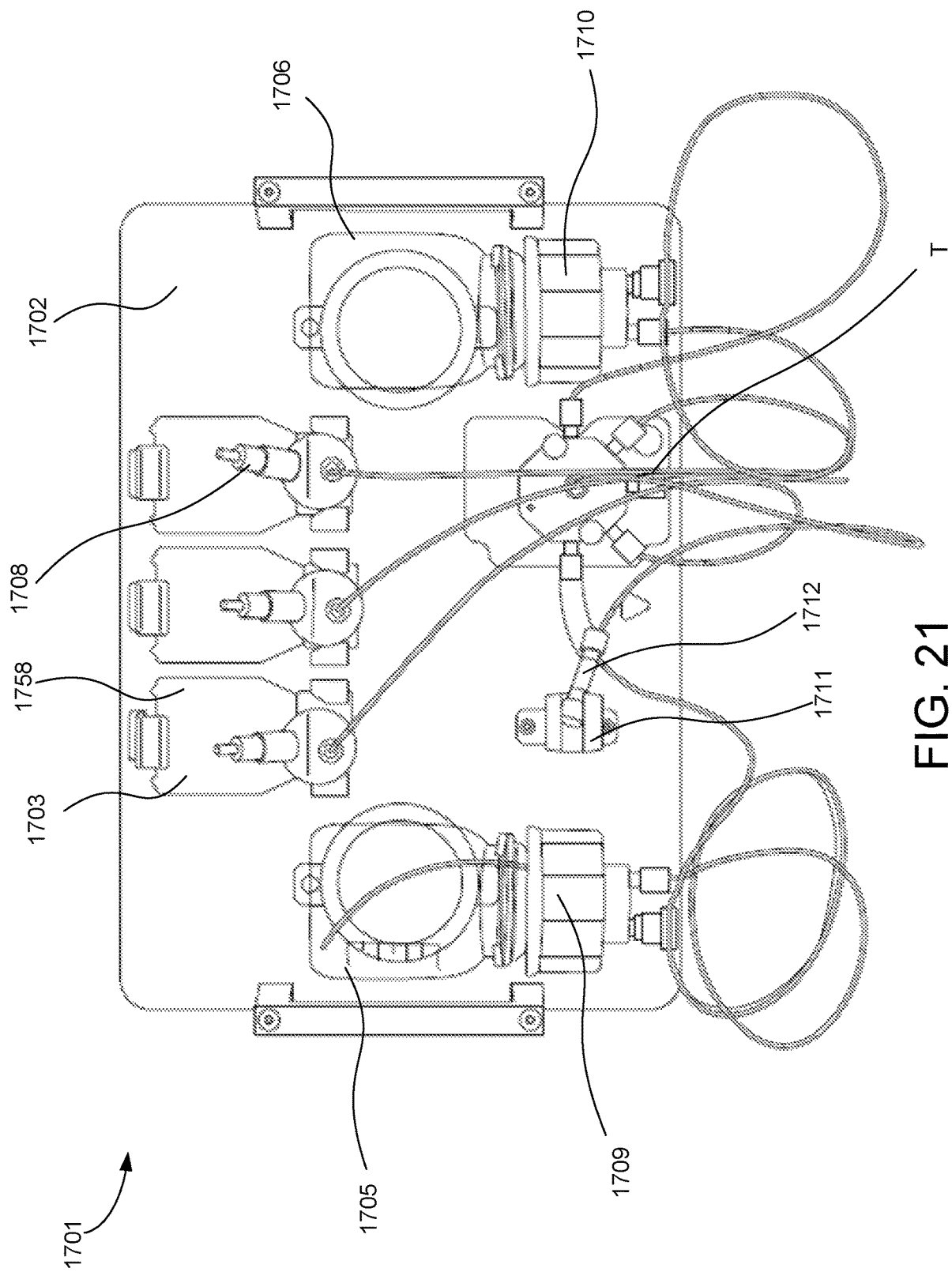
FIG. 21 is a top view of a tray assembly of a cell culturing system, according to an embodiment.

The cell culture application 1644 (also referred to as "application" or "cell culture app") is configured to communicate with the electronic control system. In some embodiments, the application 1644 can communicate directly with an electronic control system 1630 disposed on the base unit 1620. In some embodiments, the application 1644 can communicate with the electronic control system 1630 via a computing cloud environment. The application 1644 can be used to set-up, execute and monitor various steps of a cell culturing procedure using the cell culture system 1600. For example, the application 1644 can be used to cause the remote computing device 1643 to produce a series of prompts and information (e.g., via the user interface) to facilitate the cell culture methods described herein. Specifically, the cell culture application 1644 can cause the remote computing device 1643 to produce a graphical user interface (GUI) element that can include a prompt to enter various data for the cell culture procedure. FIGS. 18-20 are sample screenshots showing various GUI elements that can be produced by the remote computing device.

FIGS. 21-30 illustrate a method of preparing a cell culture system for use in a cell culturing procedure. The cell culture system 1700 illustrated in FIGS. 21-30 can include the same or similar components as other embodiments described herein (for example, the cell culturing system 1600 or the cell culturing system 2000), and therefore, some details of the cell culturing system 1700 are not described with respect to this embodiment.

Figure 22:
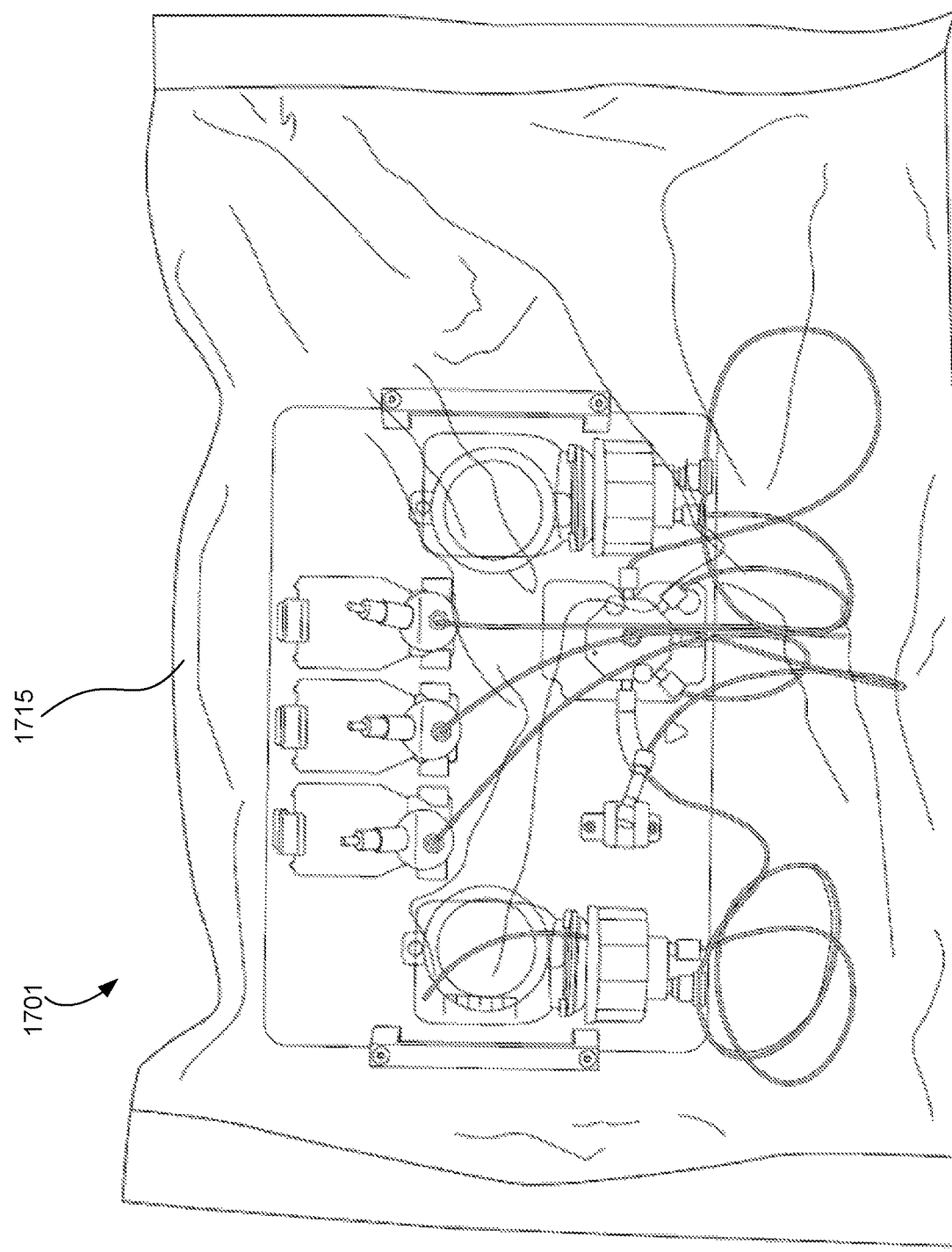
FIG. 22 is a top view of the tray assembly of FIG. 21 shown disposed within a protective overwrap.

The cell culturing system 1700 (also referred to herein as "system") includes a tray assembly 1701 and a base unit 1720 (see FIGS. 27-30). As shown, for example, in FIG. 21, the tray assembly 1701 includes a tray 1702 with the same or similar components disposed thereon as described above for other embodiments (e.g., the tray assembly 1601 or the tray assembly 2001). For example, the tray assembly 1701 includes, a waste container 1706 coupled to a lid 1710, a reagent container 1705 coupled to a lid 1709 and three lids 1708 each configured to be coupled to a cell culture container (shown in FIGS. 25-27). The lids 1708, 1709 and 1710 can include a liquid exchange port (also referred to as "fluid port") and a gas exchange port as described above for previous embodiments. The tray assembly 1701 also includes a multiport valve 1707 with a master port and multiple selectable ports to which the lids 1708, 1709, 1710 can be selectively coupled via a length of tubing. The waste container 1706 and the reagent container are shown coupled in a horizontal orientation on holders 1704. The tray assembly 1701 also includes couplers 1703 to which the cell culture container can be coupled as described below. Below where the cell culture containers will be disposed are transparent portions (or openings/cutout portions) 1758 of tray 1702. In this embodiment, a syringe holder 1711 is provided and holds a syringe port 1712 thereto. The syringe port 1712 is also coupled to the multiport valve 1707 with tubing T. FIG. 22 illustrates the tray assembly 1701 encased within an overwrap 1715 to maintain the sterility of the tray assembly 1701 during transport and storage. This arrangement allows for the tray assembly 1701 to be assembled at a centralized facility, placed in the protective overwrap 1715 and sterilized. The sterilization can be performed by any suitable method, including radiation sterilization, sterilization via ethylene oxide (EtO), or electron beam sterilization. The prepackaged, sterilized tray assembly 1701 can then be stored until needed for a cell culturing procedure.

Figure 23:
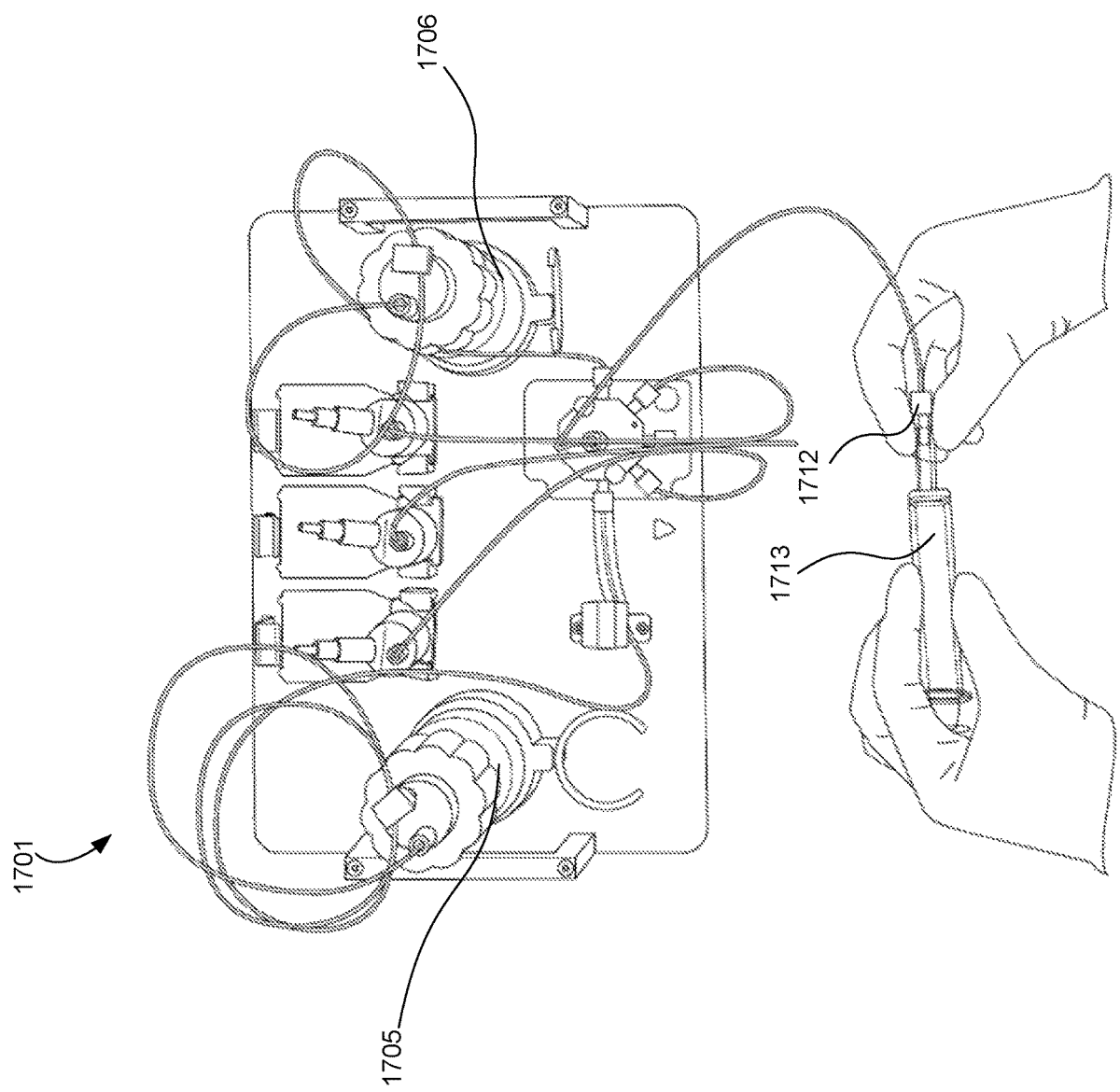
FIG. 23 is a top view of the tray assembly of FIG. 21 illustrating a fluid pump being coupled to the tray assembly.
Figure 24:
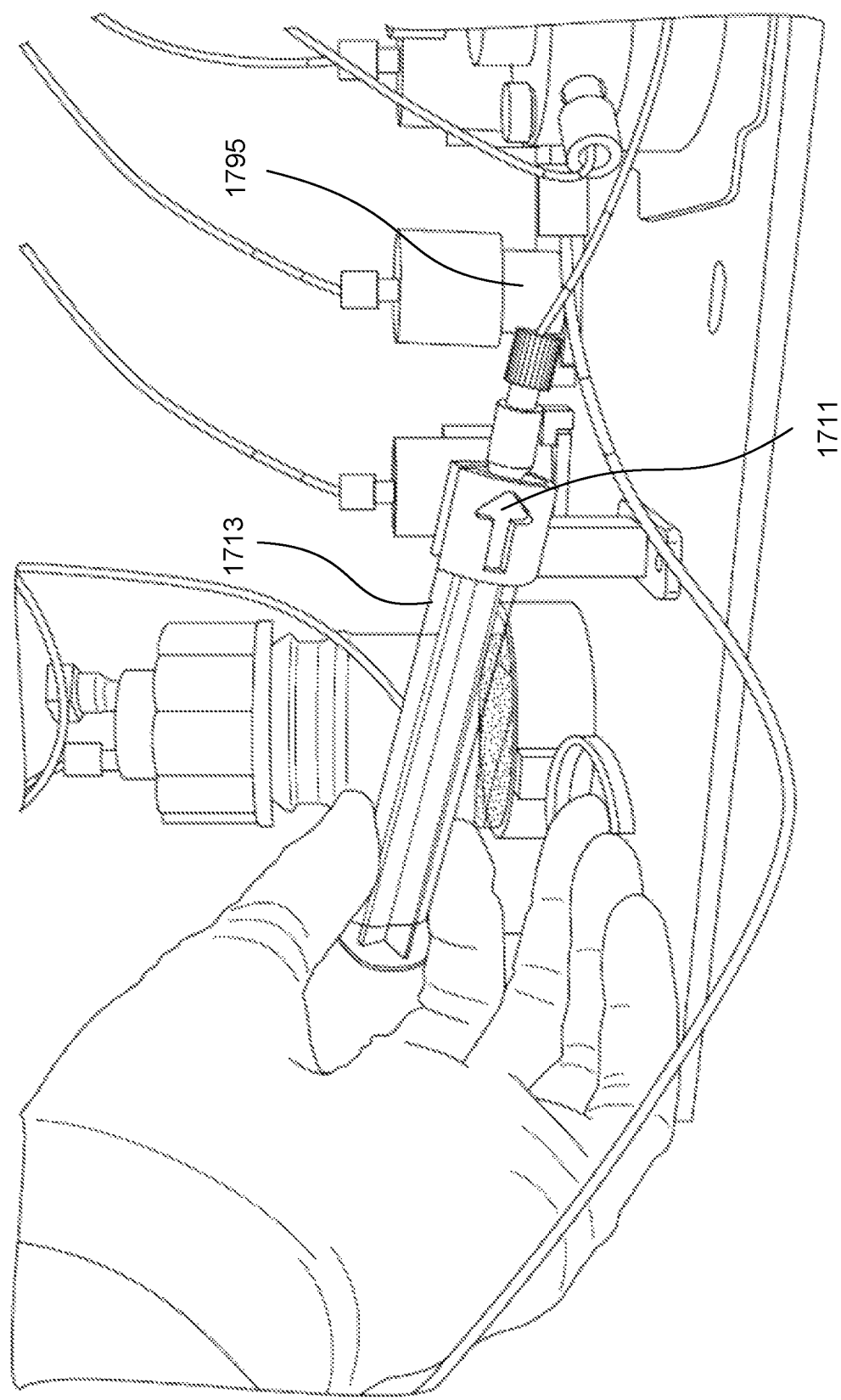
FIG. 24 is a perspective view of a portion of the tray assembly of FIG. 21 illustrating the fluid pump of FIG. 23 being coupled to the tray assembly.

The first steps in preparation for a cell culturing procedure is to prepare the cells and media (e.g., reagent) and to prepare the tray assembly 1701, which are done within an aseptic environment (e.g., laminar flow hood). The cells and media are placed within cell culture containers or vessels, which in this example, there are positions for three cell culture containers (1747, 1748, 1749 shown, for example, in FIGS. 26-27). The tray assembly 1701 is placed in the aseptic environment (e.g., a hood) and the overwrap 1715 is removed. The waste container 1706 and the reagent container 1705 can be moved to a vertical orientation within the holders 1704 as shown in FIG. 23, with the lids 1709 and 1710 in an upright position. In this example, the fluid pump 1713 is a syringe, which can be removed from an outer sterile wrap, and the port 1712 can then be coupled to the fluid pump 1713 as shown in FIG. 23. The fluid pump 1713 is then placed within the holder 1711 as shown in FIG. 24. In some embodiments, the fluid pump 1713 (e.g., syringe) is not included within the prepackaged tray assembly 1701, but rather is a separate component. In other embodiments, the fluid pump 1713 (e.g., syringe) is included within the prepackaged tray assembly 1701.

Figure 25:
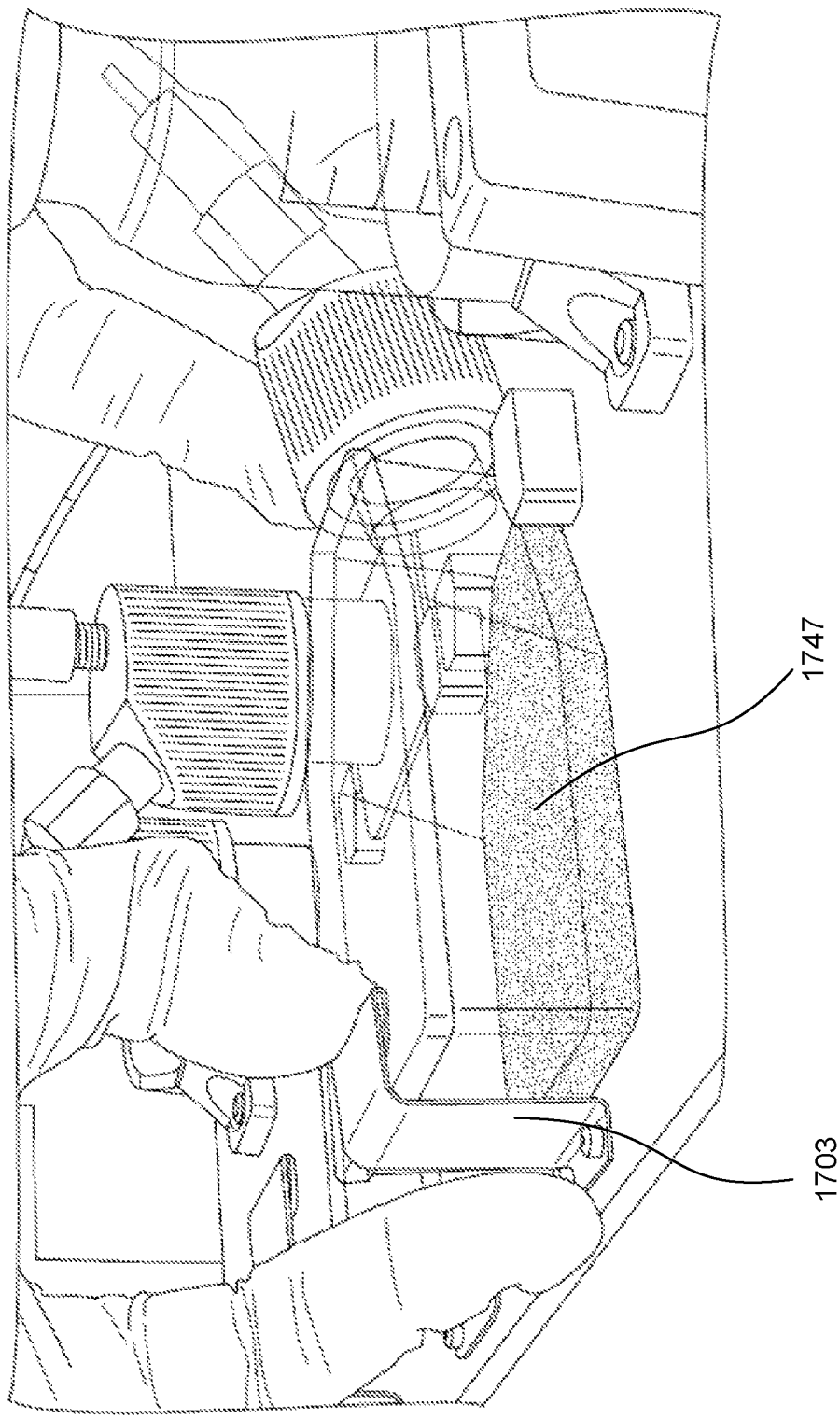
FIG. 25 is a perspective view of a portion of the tray assembly of FIG. 21 illustrating a cell culture container being coupled to the tray assembly.

After the cell culture container are loaded with the cells and initial amount of cell culture media, the lids 1708 are secured to the cell culture containers 1747, 1748, 1749 with the cells and medium therein. The lids 1708 are first removed from the shipping supports 1795 (see FIG. 24) to which they are coupled. The shipping supports 1795 are sized and configured to be received within the interior of the lids 1708 to secure the lids 1708 during shipment, storage and initial setup. This arrangement reduces the likelihood of undesired movement during the initial setup and possible contamination of the interior portion of the lids. The lids 1708 are then coupled to their respective containers while remaining fluidically coupled to the multiport valve 1707). The containers 1747, 1748, 1749 are coupled to the couplers 1703 such that the container vessels are disposed in a horizontal position as shown in FIG. 25. In this position, the bottom surface of the cell culture containers 1747, 1748, 1749 is aligned with the transparent portion 1758 of the tray.

Figure 26:
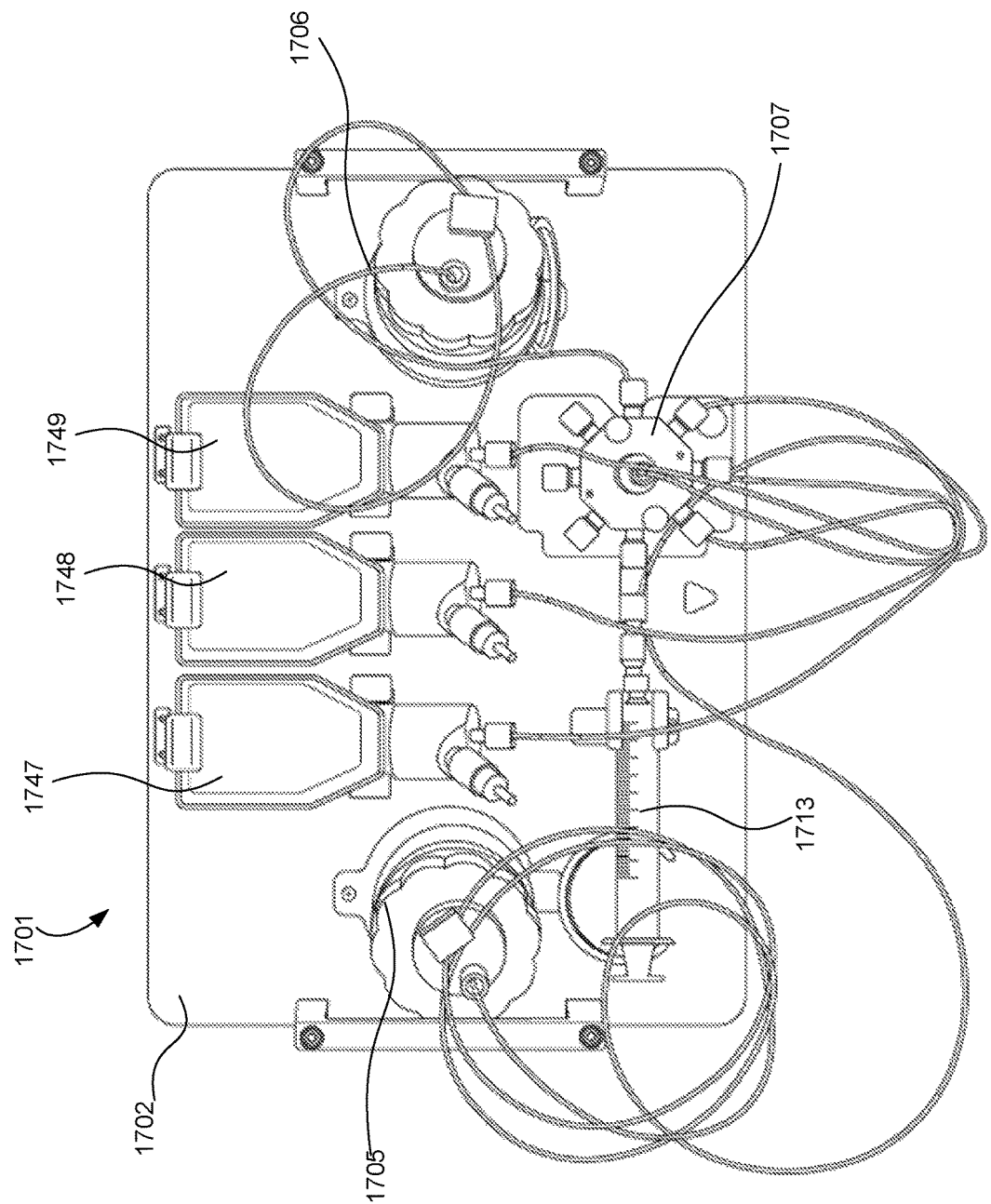
FIG. 26 is a top view of the tray assembly of FIG. 21 showing the fluid pump of FIG. 23 and three cell culture containers coupled to the tray assembly.
Figure 27:
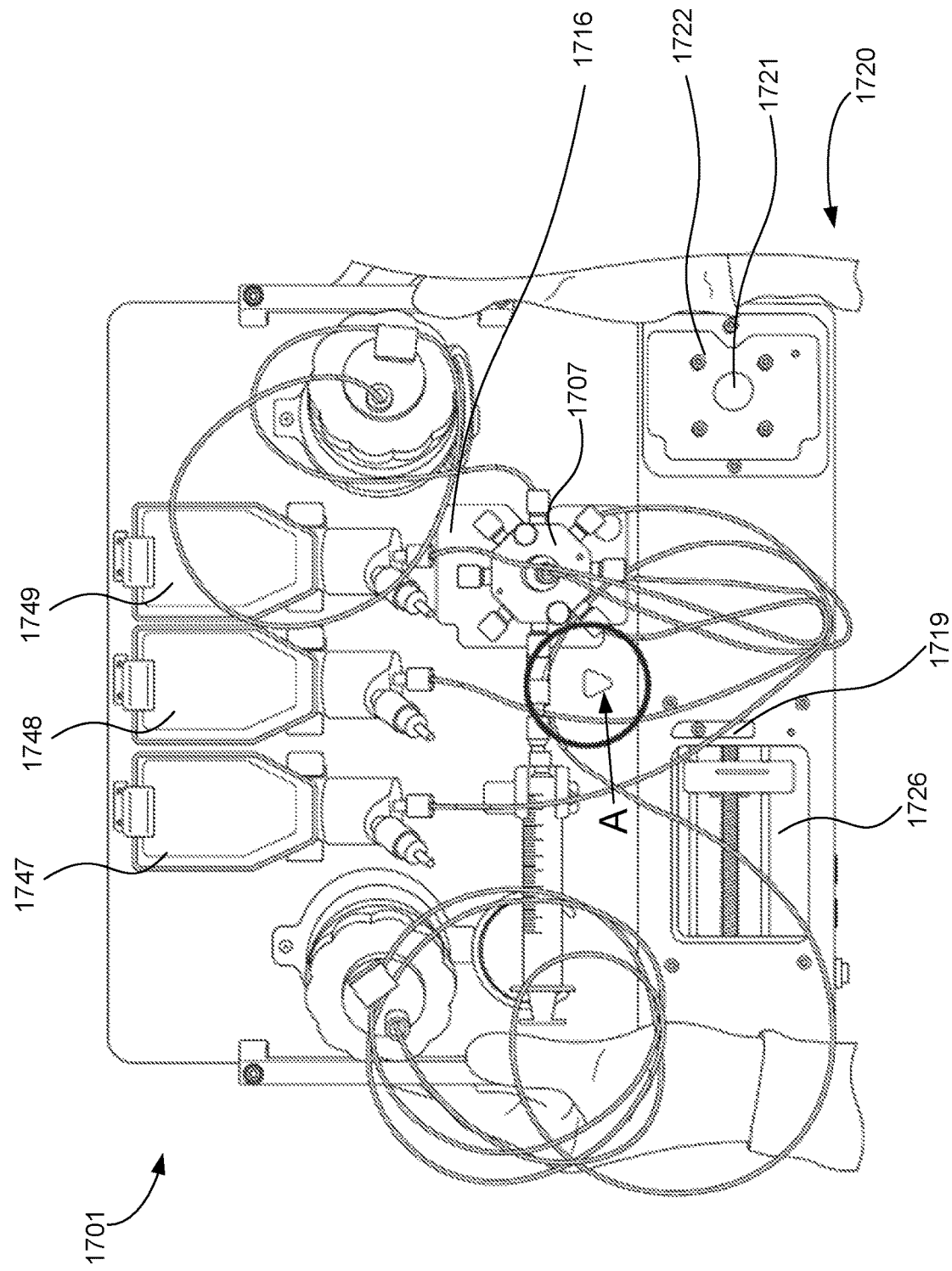
FIG. 27 is a top view of the tray assembly of FIG. 21 shown couple to a base unit, according to an embodiment.
Figure 28:
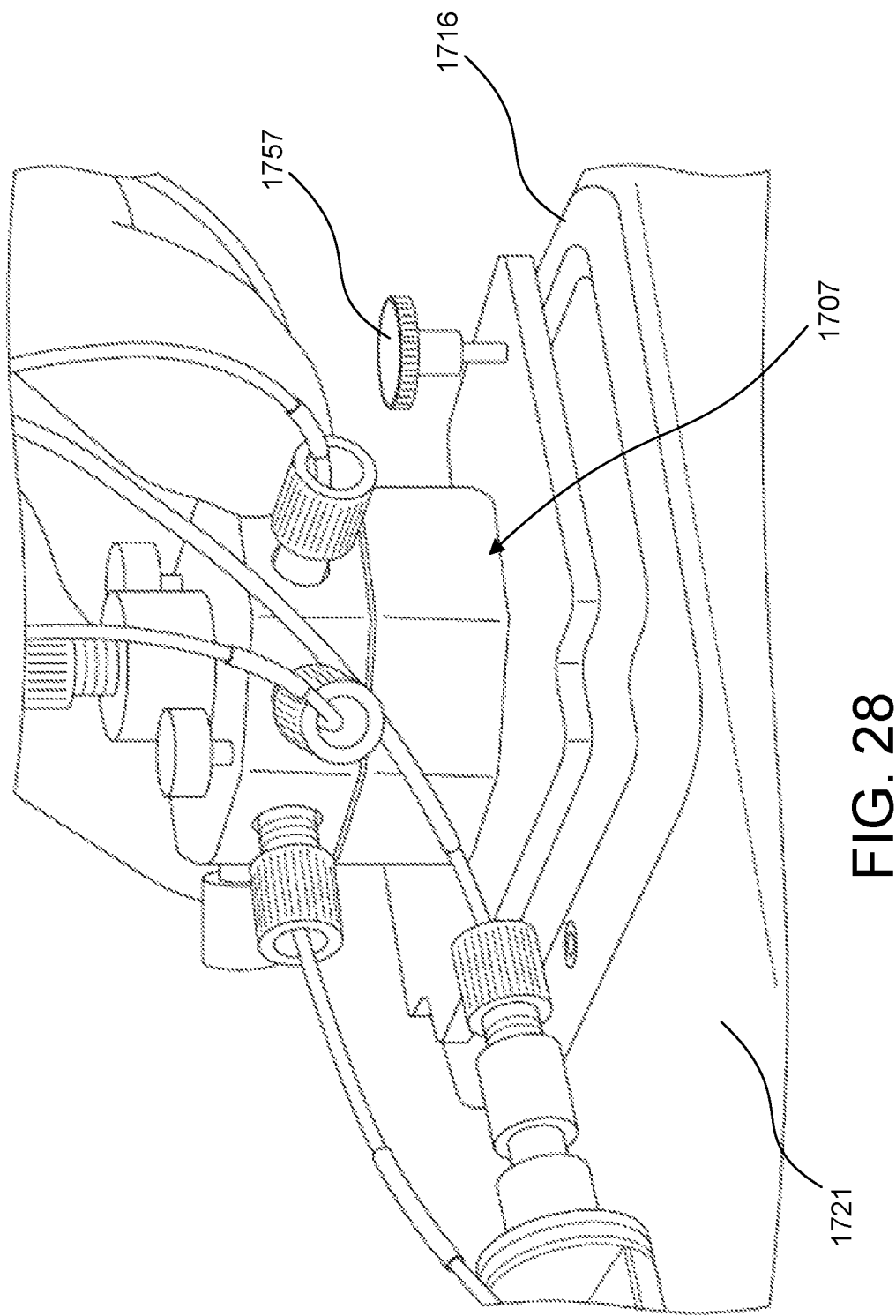
FIG. 28 is a perspective view of a multiport valve being couple to the base unit of FIG. 27.
Figure 29:
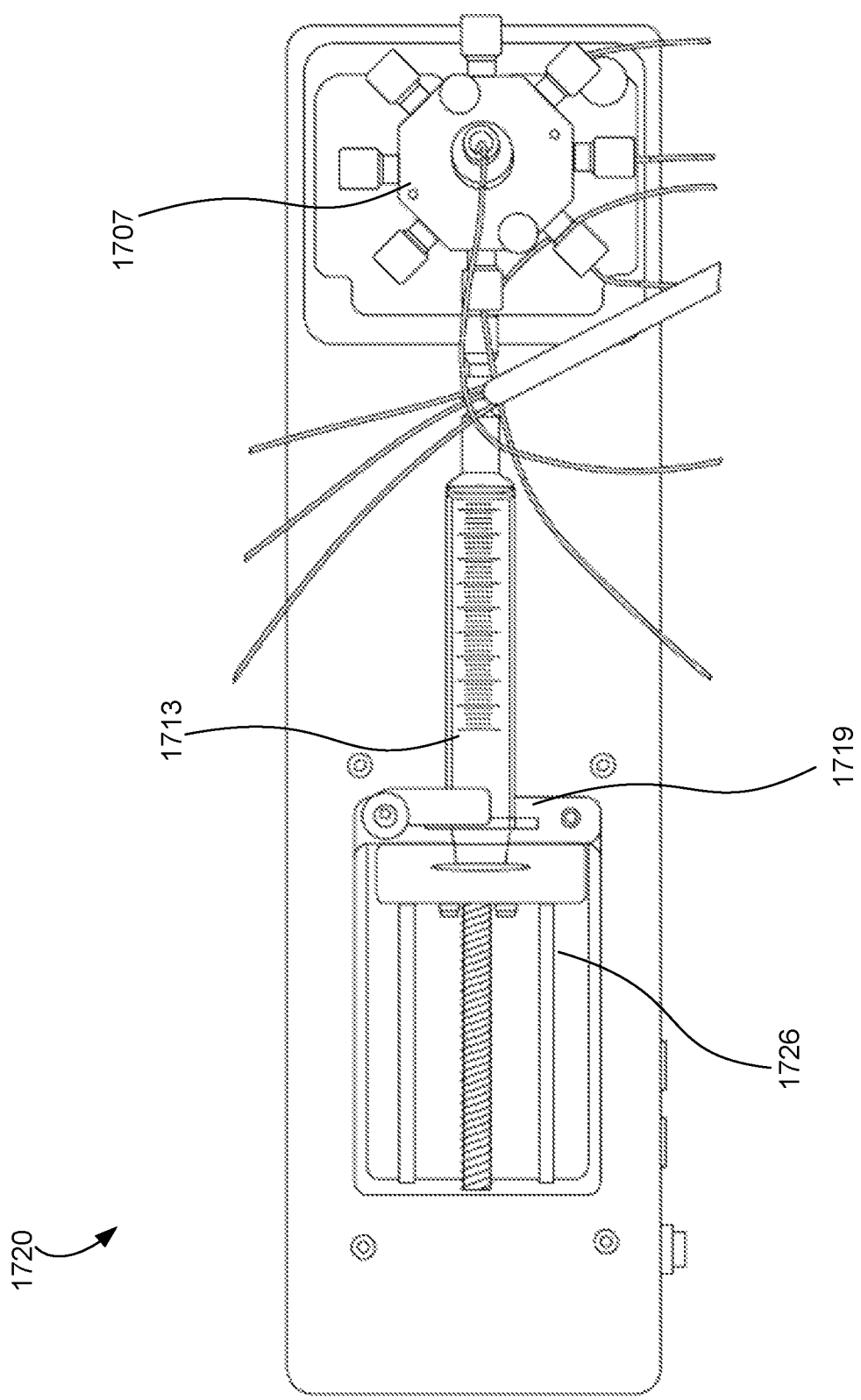
FIG. 29 is a top view of a portion of the base unit of FIG. 27.
Figure 30:
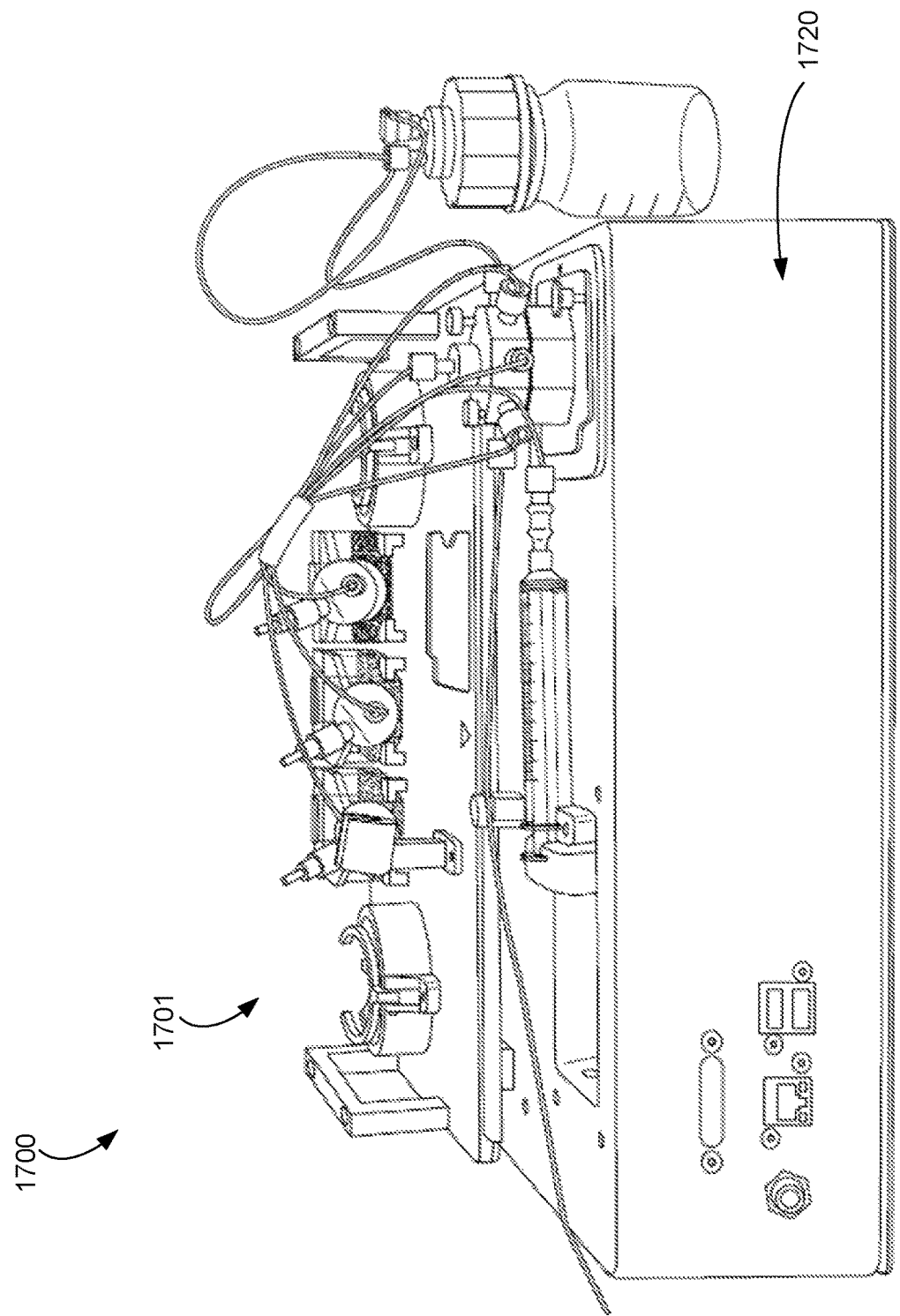
FIG. 30 is a perspective view of the tray assembly of FIG. 21 couple to the base unit of FIG. 27.

With the tray assembly 1701 fully assembled, as shown in FIG. 26, the tray assembly 1701 can be placed on the base unit 1720 as shown in FIG. 27. This can be done outside of the aseptic environment as components (e.g., containers, lids, valve, syringe) are fluidically coupled in a closed system. The tray assembly 1701 should be oriented with the arrow (labeled A and encircled) on the tray 1702 pointing towards the base unit 1720 as shown in FIG. 27. As also shown in FIG. 27, the base unit 1720 includes a pump actuator 1726, a valve connector 1721 and a valve actuator 1722. In this embodiment, the multiport valve 1707 is removable from the tray 1702 and can be coupled to the base unit 1720. More specifically, a mounting portion 1716 of the multiport valve 1707 can be detached from the tray 1702 by removing the fastener 1757 and attaching the mounting portion 1716 to a mating valve connector 1722 of the base unit 1720 with the same or a different fastener 1757, as shown in FIGS. 28 and 29. The fluid pump 1713 (e.g., syringe) is decoupled from the tray assembly 1701 and coupled to a holder 1719 of the base unit 1720 as shown in FIG. 29. This operation is performed while the fluid pump 1713 remains fluidically coupled to the multiport valve 1707, thereby maintain the closed system. The holder 1719 can be part of a fluid pump portion (e.g., 1627) of the base unit 1720 as described above for system 1600. The waste container 1706 and the reagent container 1705 can be removed from the tray 1702 and placed near the base unit 1720, as shown in FIG. 30 (or in any other suitable location).

Figure 58:
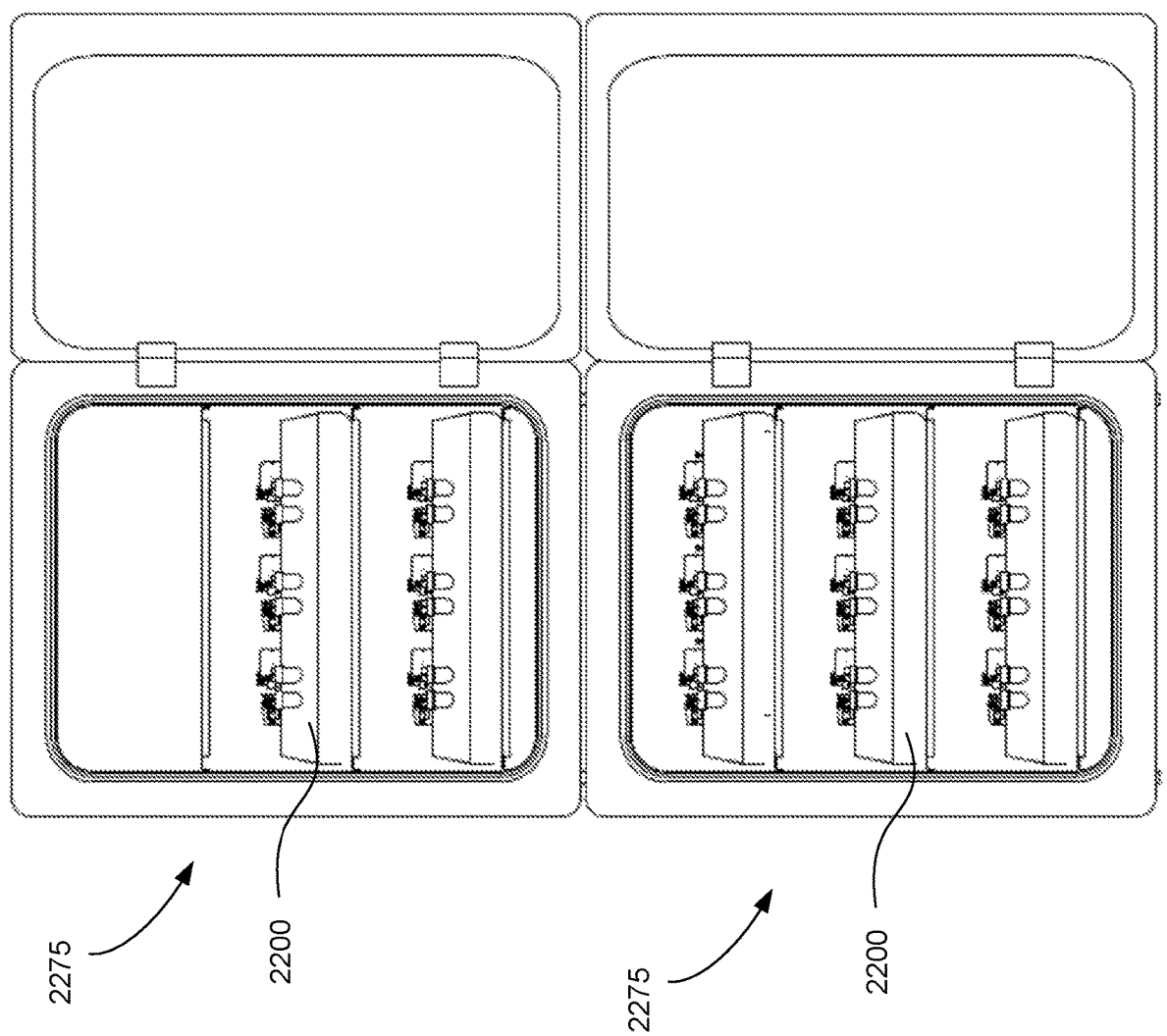
FIG. 58 is a front view of a pair of incubators with multiple cell culturing systems disposed on shelves therein.

The base unit 1720 and the tray assembly 1701 can then be moved into an incubation environment (e.g., an incubator 2275 as shown in FIG. 58) to facilitate the cell growth in a temperature-controlled environment if the tray assembly 1701 is coupled to the base unit 1720 outside of the incubator. In some embodiments, the base unit 1720 is disposed within the incubator when the tray assembly 1701 is coupled thereto.

Figure 31:
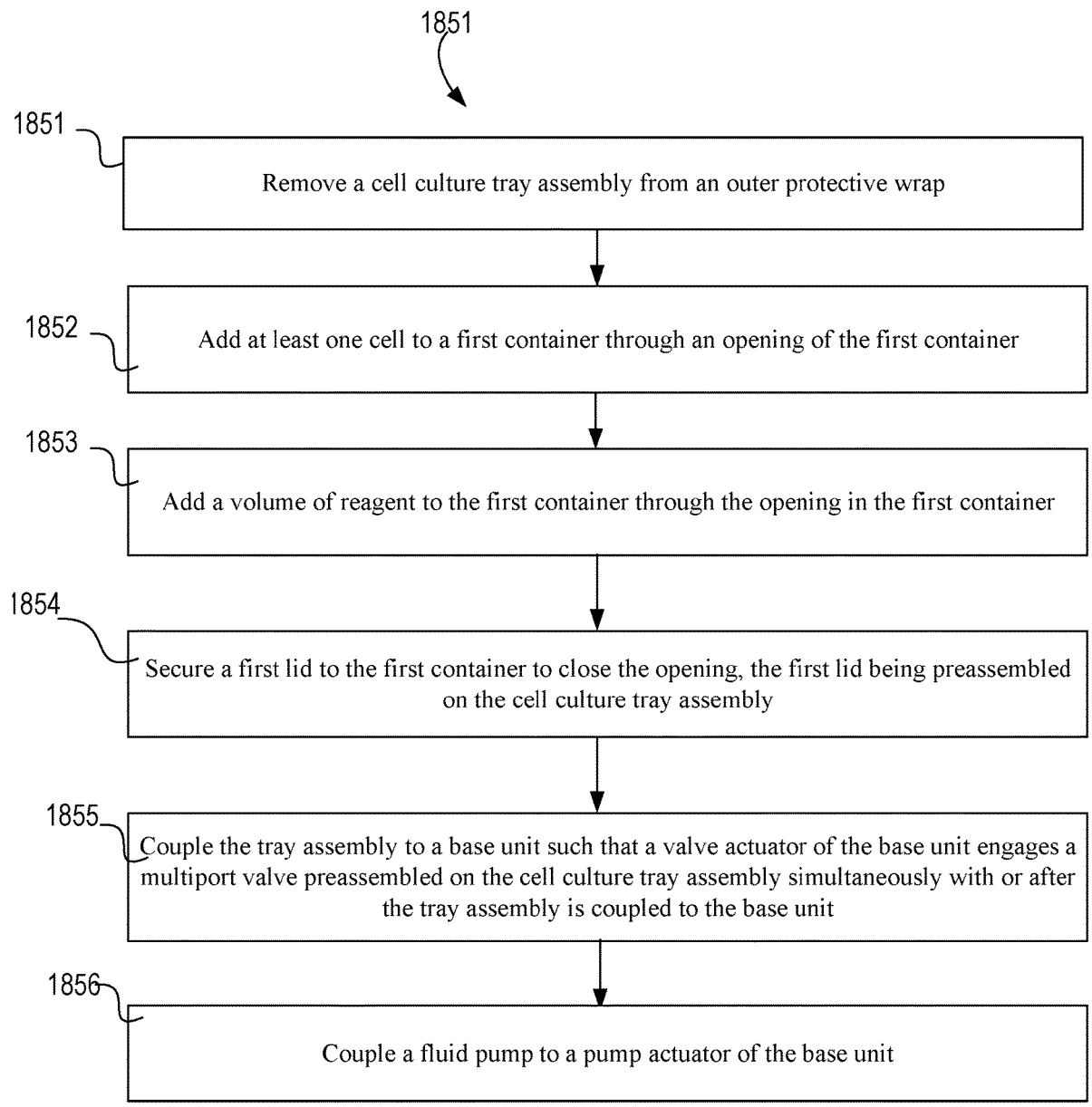
FIG. 31 is a flowchart illustrating a method of preparing a cell culturing system for use in a cell culturing procedure, according to an embodiment.

FIG. 31 is a flowchart illustrating a method 1850 of preparing a cell culture system for use in a cell culturing procedure. The method 1850 can be performed with any of the cell culture systems described herein, such as, for example, the cell culture system 1700 described above with reference to FIGS. 23-30. At 1851, a cell culture tray assembly is removed from an outer protective wrap. The tray assembly can be any of the tray assemblies described herein and includes a tray, a first lid, a second lid, and a multiport valve. The first lid is coupled to the tray and configured to be removably coupled to a first container, and the second lid is coupled to the tray and configured to be removably coupled to a second container. The multiport valve is coupled to the tray and includes a master port and multiple selectable ports. A first selectable port is aseptically coupled to the first liquid exchange port of the first lid, and a second selectable port is aseptically coupled to the second liquid exchange port of the second lid. As described herein, by having the lids precoupled to the appropriate ports, fewer operations are performed during the initial setup, thereby reducing the likelihood of contamination and error. At 1852, at least one cell sample is added to a first container through an opening of the first container and at 1853, a volume of reagent (e.g., a cell culture media) is added to the first container through the opening of the first container. At 1854, the first lid is coupled to the first container to close the opening. In some embodiments, the second lid can optionally be coupled to the second container. At 1855, the tray assembly is coupled to a base unit. In some embodiments, when the tray assembly is coupled to the base unit, a valve actuator of the base unit simultaneously engages the multiport valve of the tray assembly. In some embodiments, the valve actuator engages the multiport valve after the tray assembly is coupled to the base unit. At 1856, a fluid pump is coupled to a pump actuator of the base unit. For example, the fluid pump can be a syringe or a peristaltic pump that can be coupled the base unit. After preparation of the cell culturing assembly, any of the methods of cell culturing described herein can be performed.

Figure 32:
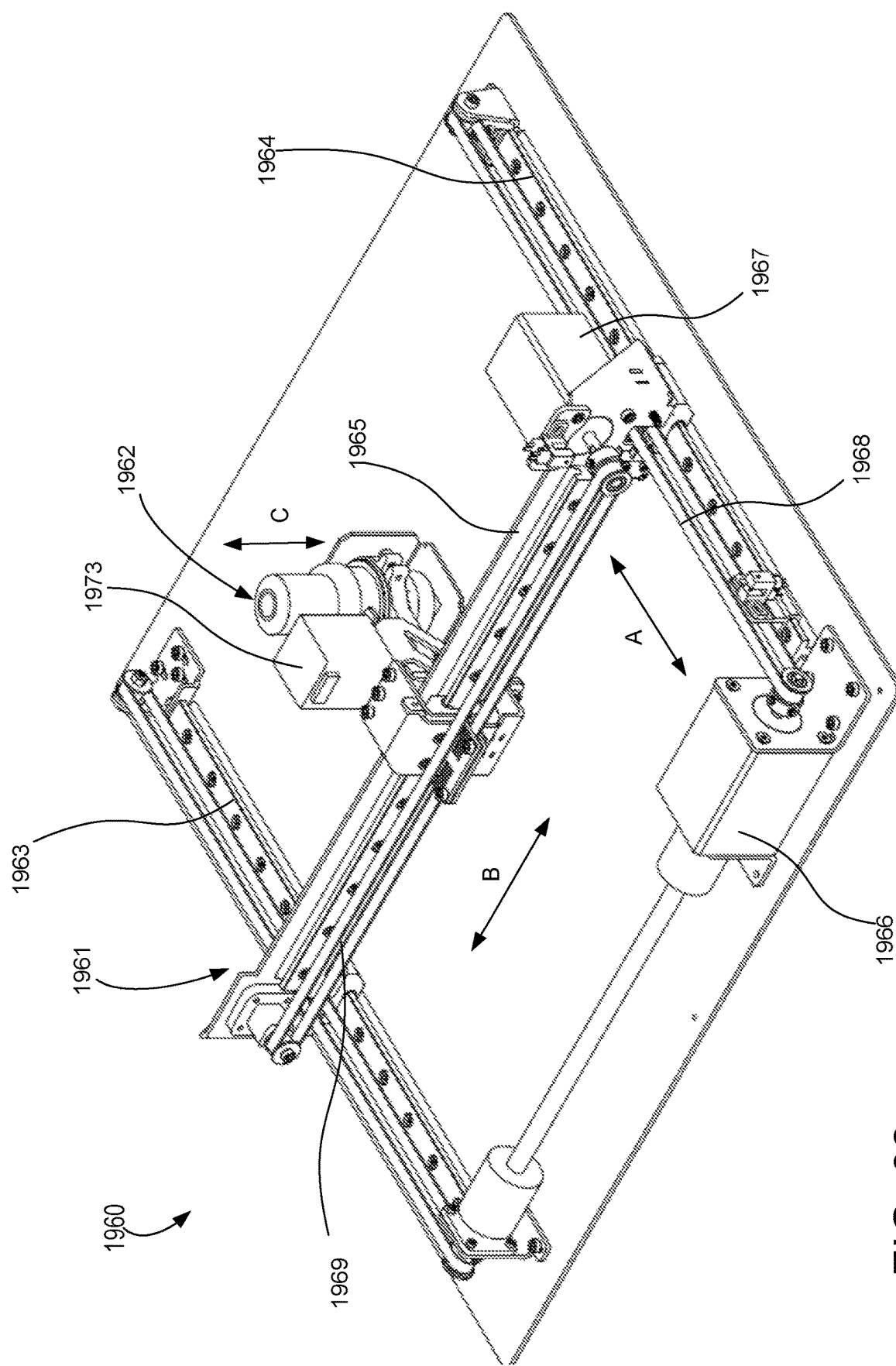
FIG. 32 is a perspective view of an imaging device of a base unit of a cell culturing system, according to an embodiment.
Figure 33:
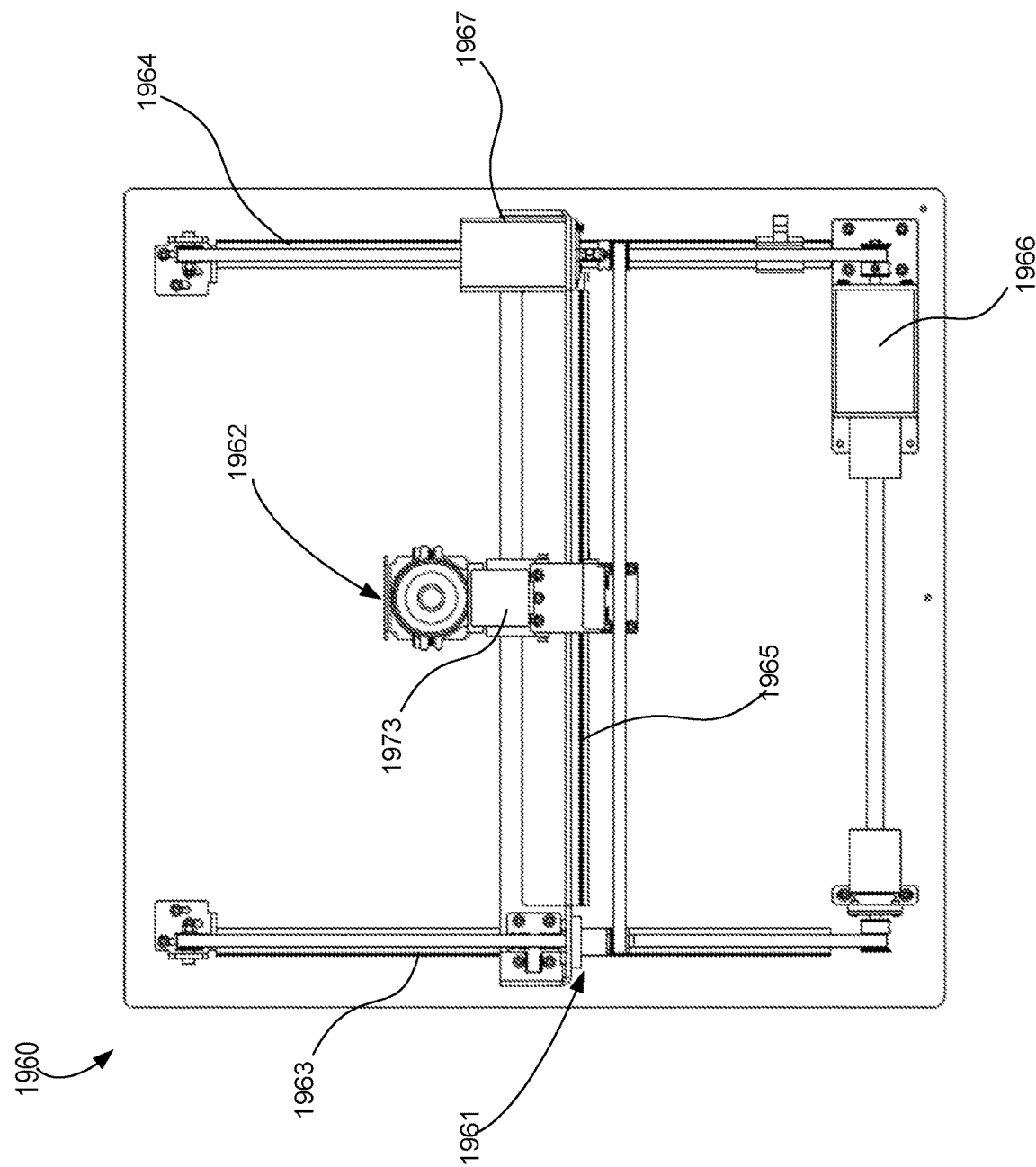
FIG. 33 is a top view of the imaging device of FIG. 32.
Figure 34:
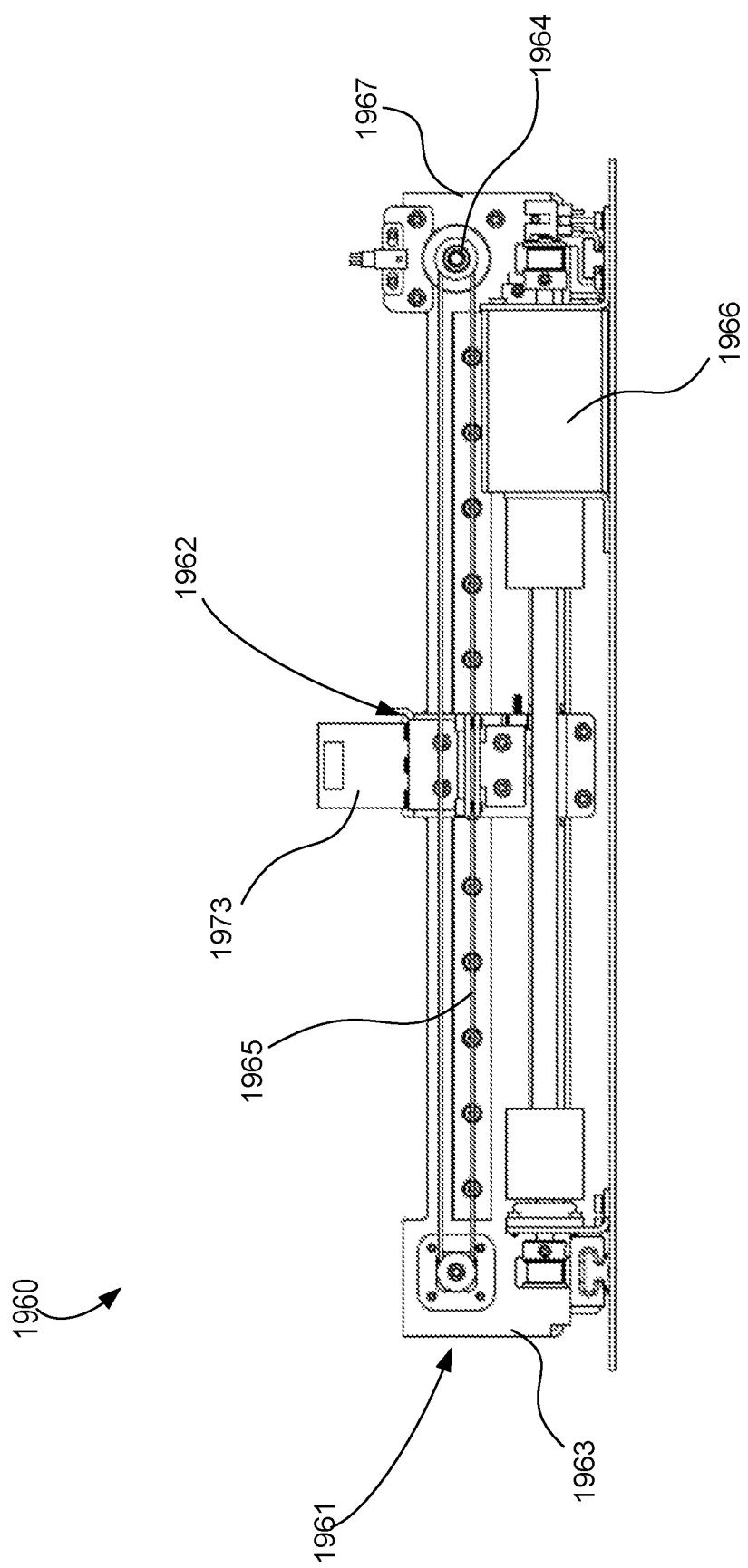
FIG. 34 is a side view of the imaging device of FIG. 32.
Figure 35:
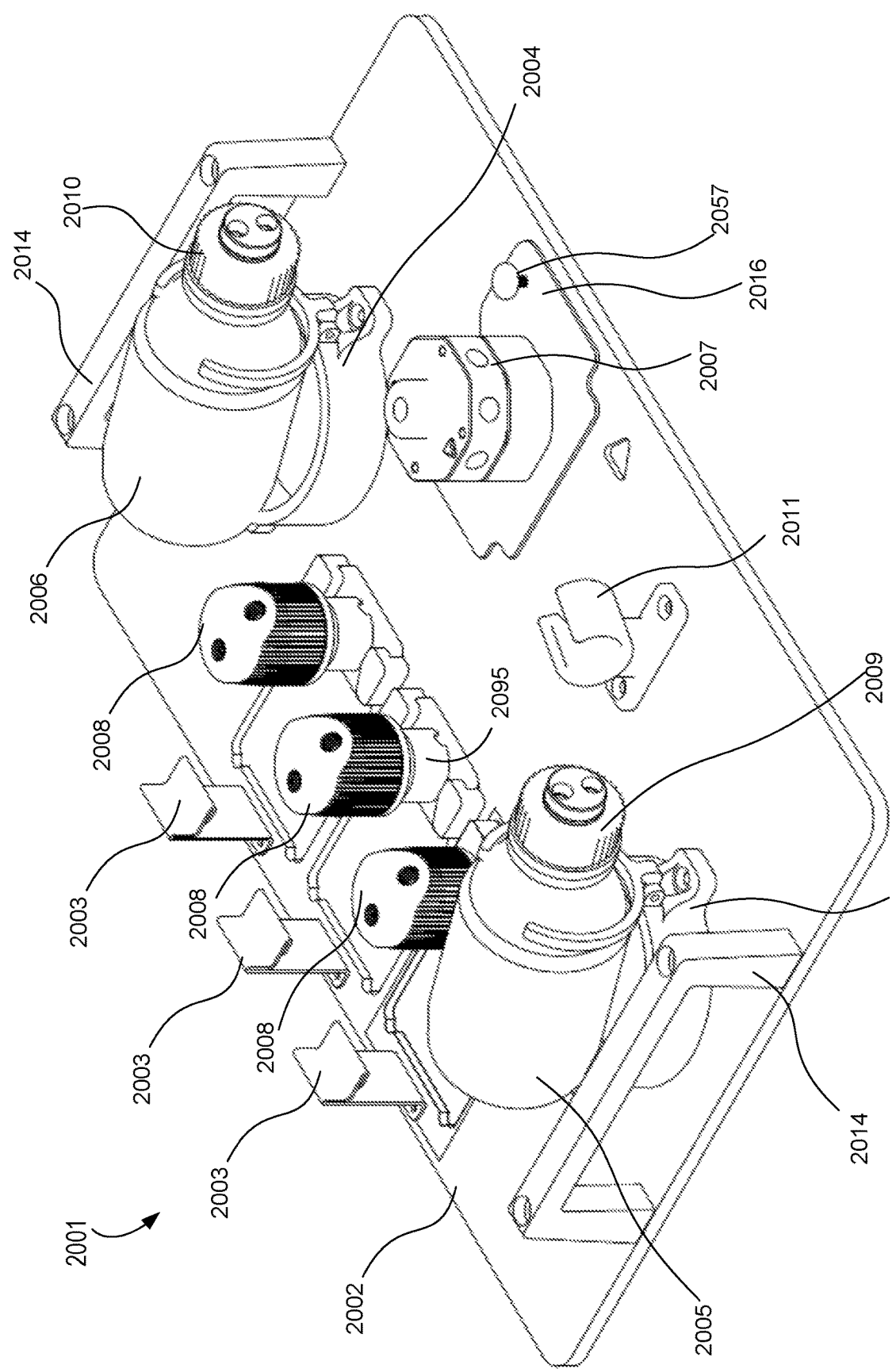
FIG. 35 is a perspective view of a tray assembly of a cell culturing system, according to another embodiment.
Figure 36:
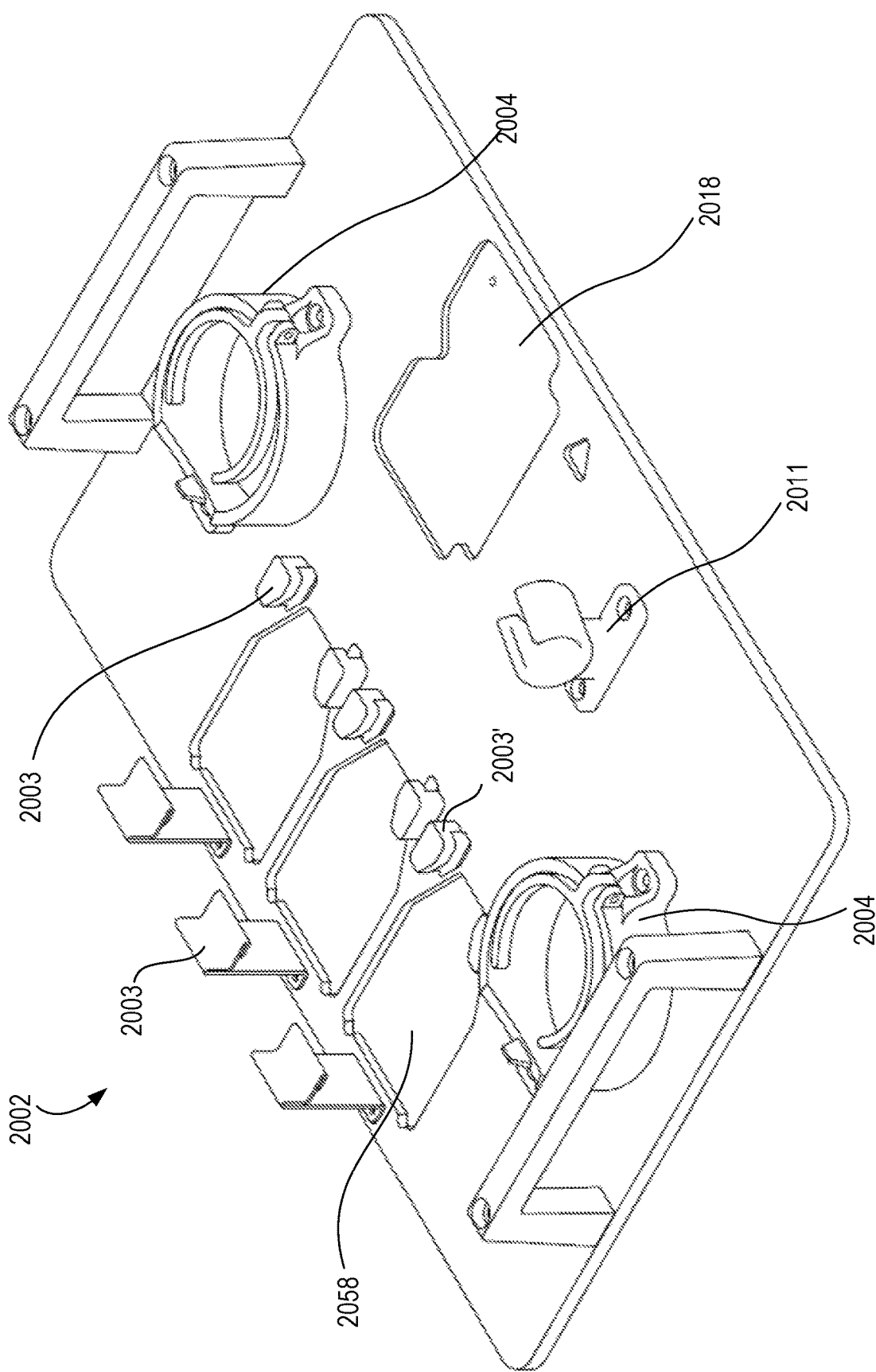
FIG. 36 is a perspective view of a portion of the tray assembly of FIG. 35 with removable components removed.

As described above, in some embodiments, an automated cell culture system can include an imaging device that includes a microscope that may be moved relative to the housing of a base unit to image the contents of any cell culture vessel of the automated cell culture system. In some embodiments, the microscope may be mounted on a mechanical system that is capable of moving the microscope into alignment with the cell culture vessels or a cell counting chip. The mechanical system can be any suitable assembly for moving the imaging device, such as a 2-dimensional or 3-dimensional gantry mechanism or a hinged robotic arm mechanism. FIGS. 32-34 illustrate an example embodiment of such an optical imaging system (also referred to as a microscope imaging device). The microscope imaging device 1960 can be mounted within the housing of any of the base units of the cell culture systems described herein. For example, the microscope imaging device 1960 can be included within the base unit 1720, the base unit 2020, or any other base units described herein. The microscope imaging device 1960 includes an imaging device 1962 that can view through a window or transparent portion in the top of the base unit and through cut outs (or transparent portions) in both the tray (see, e.g., the transparent portion 1758 described herein) and any shaking platform (e.g., support for a tray in contact with an agitator). Thus, the microscope imaging device 1960 can be used to collect information related to the contents of a cell culture container and/or within a cell counting chip as described herein. For example, in some embodiments, the microscope imaging device 1960 can obtain images of a cell culture container and/or a cell counting chip during a cell culturing procedure, and the images can be used to determine, for example, the density of the contents to determine a quantity of cells within the container (for example, for suspension cells), or a percentage confluence (i.e., percentage of coverage of the container area with cells) in the case of, for example, adherent cells.

The microscope imaging device 1960 includes a gantry system 1961 that provides for movement of the imaging device 1962 in multiple directions relative to the housing of the base unit (not shown in FIGS. 32-34). The gantry 1961 includes a set of rails 1963, 1964 and a cross-rail 1965. The cross-rail 1965 is mounted to and can move back and forth relative to the rails 1963 and 1964 in the direction of arrow B. More specifically, a first motor 1966 can drive a belt 1968 to which the cross-rail 1965 is operatively coupled. The image device 1962 is movably mounted to the cross-rail 1965 and is operatively coupled to a belt 1969 that is driven by a second motor 1967 to move the imaging device 1962 in a direction of arrow B. The imaging device 1962 is further moveable in a direction of arrow C via a motor 1973 for focusing the imaging device 1960. Thus, during operation, the imaging device 1962 can be moved in the direction of arrow A via the movement of the rail 1965 relative to the rails 1963 and 1964, in the direction of arrow B via its movement relative to the rail 1966, and in the direction of arrow C relative to the base of the imaging device 1960 to be positioned at a desired location relative to a cell culture container and/or a cell counting chip.

A light(s) or light source (not shown) can be mounted above the tray assembly of the system on another multi-axis gantry which allows it to be controlled to move to the same position as the microscope within the base unit. In some embodiments, the light source can be operatively coupled to the same gantry (e.g., gantry 1961) as the microscope such that the microscope 1962 and light source can be moved together. In some embodiments, the microscope imaging device 1960 can be controlled by any of the electronic control systems and according to any of the methods described herein. For example, in some embodiments, the microscope imaging device 1960 (and any associated light source) can be controlled to automatically image a cell culture container (e.g., to produce a sensor output associated with the cells within the container). A cell sensor module of an electronic control system (e.g., the electronic control system 1730) or any other electronic control system described herein can receive the sensor output and produce a signal associated with a quantity of cells within the container (e.g., cell density or a percentage confluence). Based on this information the electronic control system can then produce one or more signals (e.g., valve control signals, pump control signals, agitator signals, or the like) to cause the transfer of the cells from within the cell culture container to another container within the system. Similarly stated, in some embodiments, the microscope imaging device 1960 can provide input for automated cell passaging or cell harvesting operations.

FIGS. 35-44 illustrate another embodiment of a cell culturing system 2000, for use in a cell culturing procedure. The cell culture system 2000 can include the same or similar components as other embodiments described herein (including the cell culture system 1700) and can have the same or similar functions as the previous embodiments described herein, and therefore, some details of the cell culturing system 2000 are not described with respect to this embodiment.

The cell culturing system 2000 (also referred to herein as "system") includes a tray assembly 2001 (see, e.g., FIGS. 35-37) and a base unit 2020 (see, e.g., FIGS. 38-44). As shown, for example, in FIG. 35, the tray assembly 2001 includes a tray 2002 with handles 2014 and with the same or similar components disposed thereon as described above for previous embodiments (e.g., tray assemblies 1601 and 1701). For example, the tray assembly 2001 includes, a waste container 2006 coupled to a lid 2010, a reagent container 2005 coupled to a lid 2009 and three lids 2008 configured to be coupled to a cell culture container (not shown in FIGS. 35-44). The lids 2008, 2009 and 2010 can include a liquid exchange port (also referred to as "fluid port") and a gas exchange port as described above for previous embodiments. The tray assembly 2001 also includes a multiport valve 2007 with a master port and multiple selectable ports to which the lids 2008, 2009, 2010 can be selectively coupled via a length of tubing (not shown). For example, as described herein, the lids 2008, 2009, 2010 can be coupled to the multiport valve 2007 preassembled and within the overwrap. FIGS. 35-44 do not show the tubing and connections between the various components and the multiport valve 2007 for illustration purposes. The multiport valve 2007 is coupled to the tray 2002 via a mounting portion 2016 that matingly couples to and fits within a mounting pocket 2018 of the tray 2002 in a puzzle-like manner.

Figure 37:
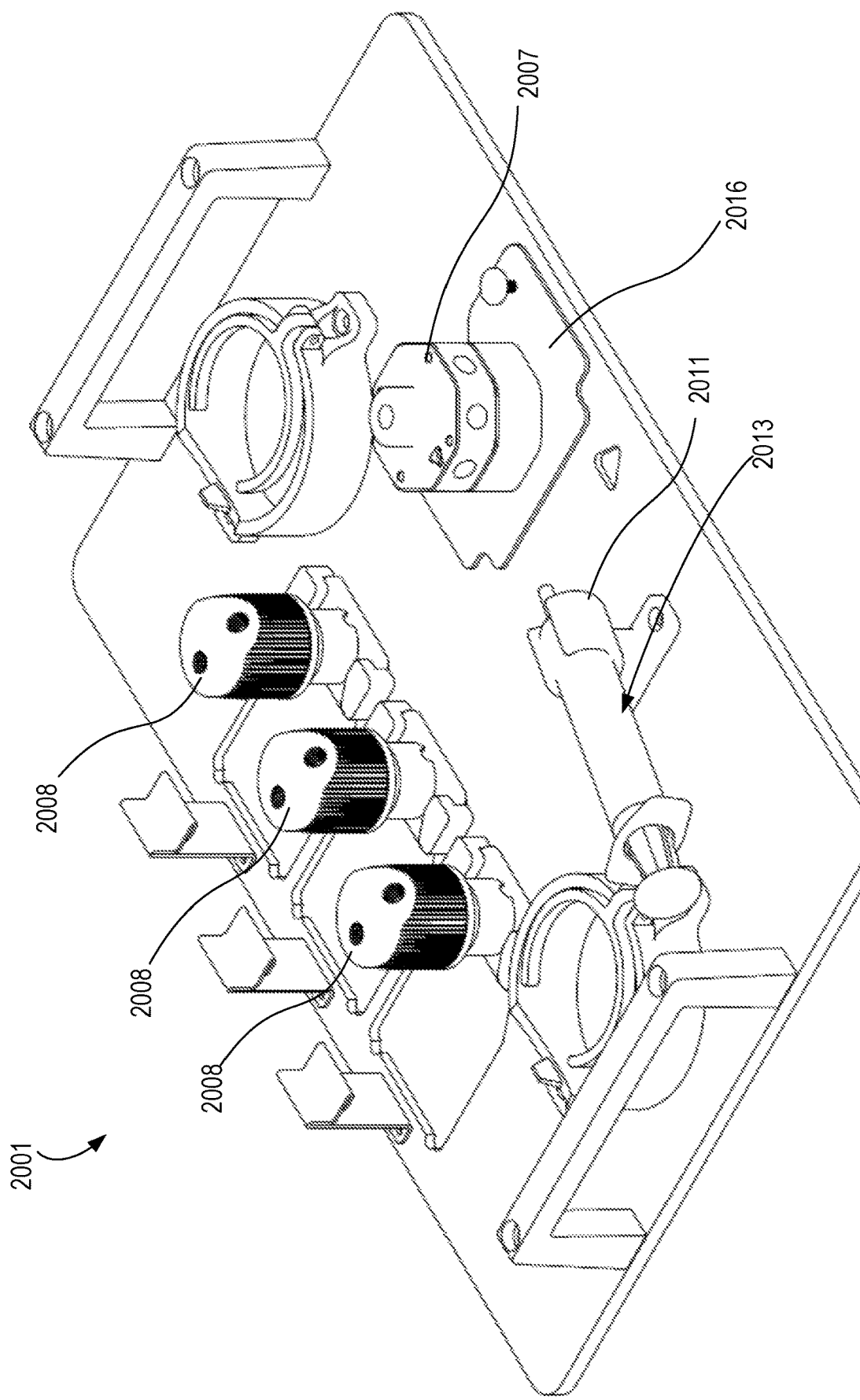
FIG. 37 is a perspective view of a portion of the tray assembly of FIG. 35. Showing a multiport valve, lids and a fluid pump coupled to the tray.
Figure 38:
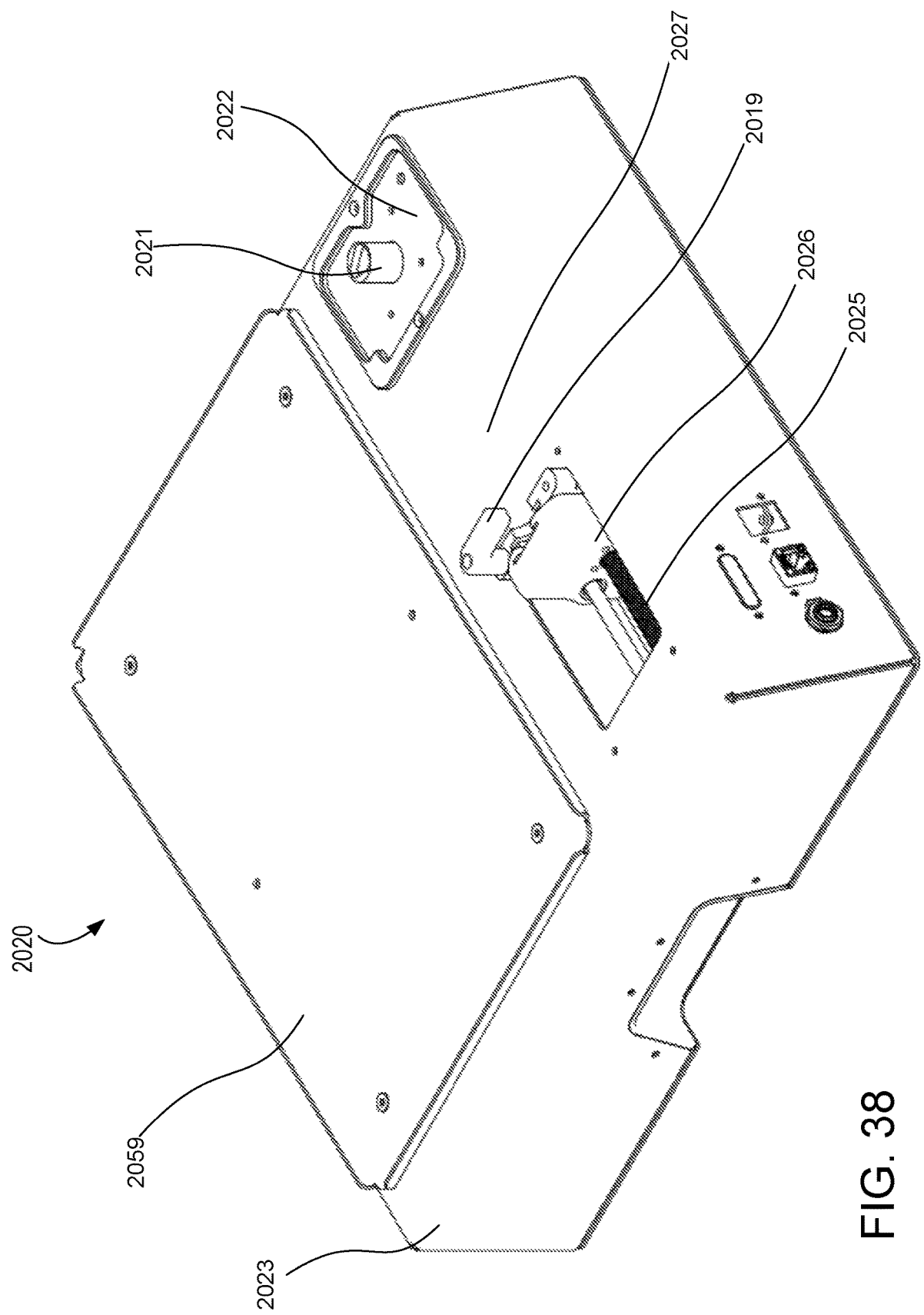
FIG. 38 is a perspective view of a base unit of the cell culturing system that can be used with the tray assembly of FIG. 35.
Figure 39:
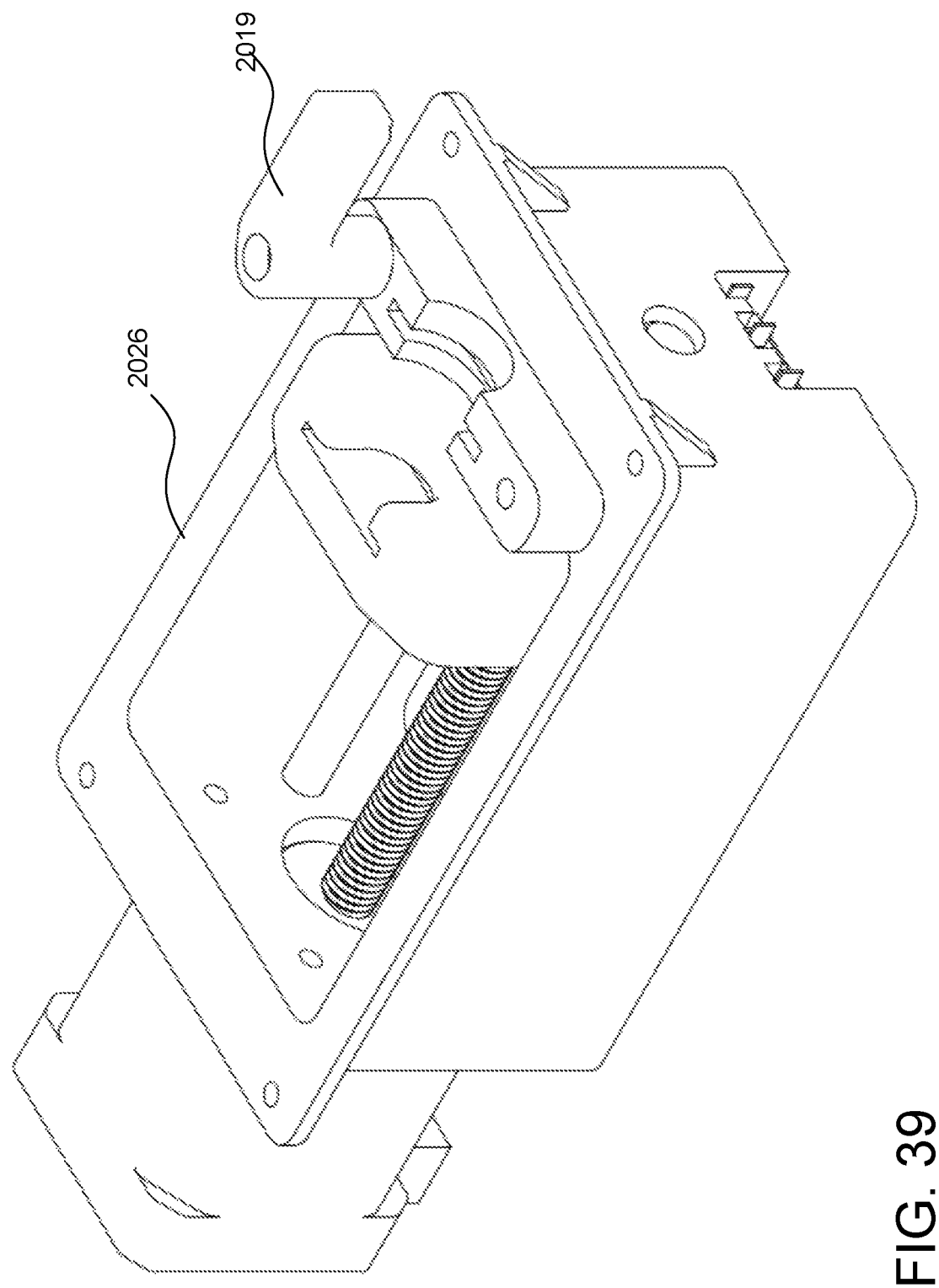
FIG. 39 is a perspective view of a pump actuator of the base unit of FIG. 38.

The waste container 2006 and the reagent container 2005 are shown coupled in a horizontal orientation on holders 2004. The tray assembly 2001 also includes couplers 2003, 2003' to which the cell culture containers can be coupled as described herein. Specifically, the coupler 2003 is a bracket that extends around a first end portion of the cell culture container (not shown) and the coupler 2003 is a pair of tabs that receive a flange portion of a second end portion of the cell culture container. The couplers 2003 also function to retain the temporary shipping supports 2095 to which the lids 2008 are coupled during storage, shipment, and initial setup. The couplers 2003, 2003' retain the cell culture containers in a predetermined, fixed location on the tray 2002. Below where the cell culture containers will be disposed are transparent portions 2058 (see, e.g., FIG. 36) of tray 2002. In this embodiment, a pump holder 2011 is provided that can hold a pump port (not shown) as described above for previous embodiments. As described above, the tray assembly 2001 is preassembled and placed within an overwrap (not shown) to maintain the sterility of the tray assembly 2001 during transport and storage. FIG. 37 illustrates the tray assembly 2001 when the overwrap is removed (i.e., within an aseptic environment), with the waste container 2006 and the reagent container 2005 removed and a fluid pump 2013 coupled to the holder 2011. As shown in FIG. 37, in this embodiment, the fluid pump 2013 is a syringe.

Figure 40:
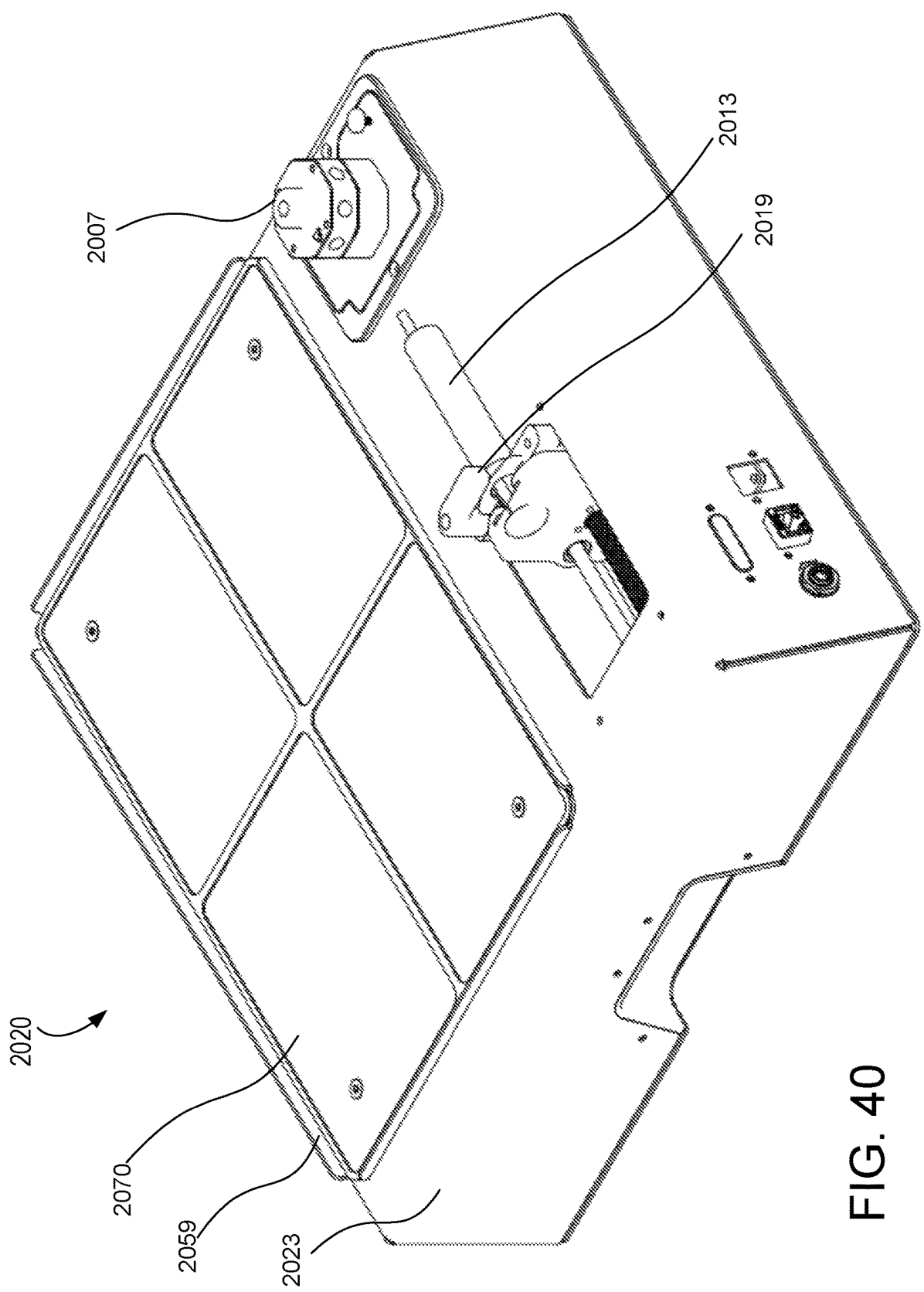
FIG. 40 is a perspective view of the base unit of FIG. 38 with a fluid pump and multiport valve coupled thereto.
Figure 41:
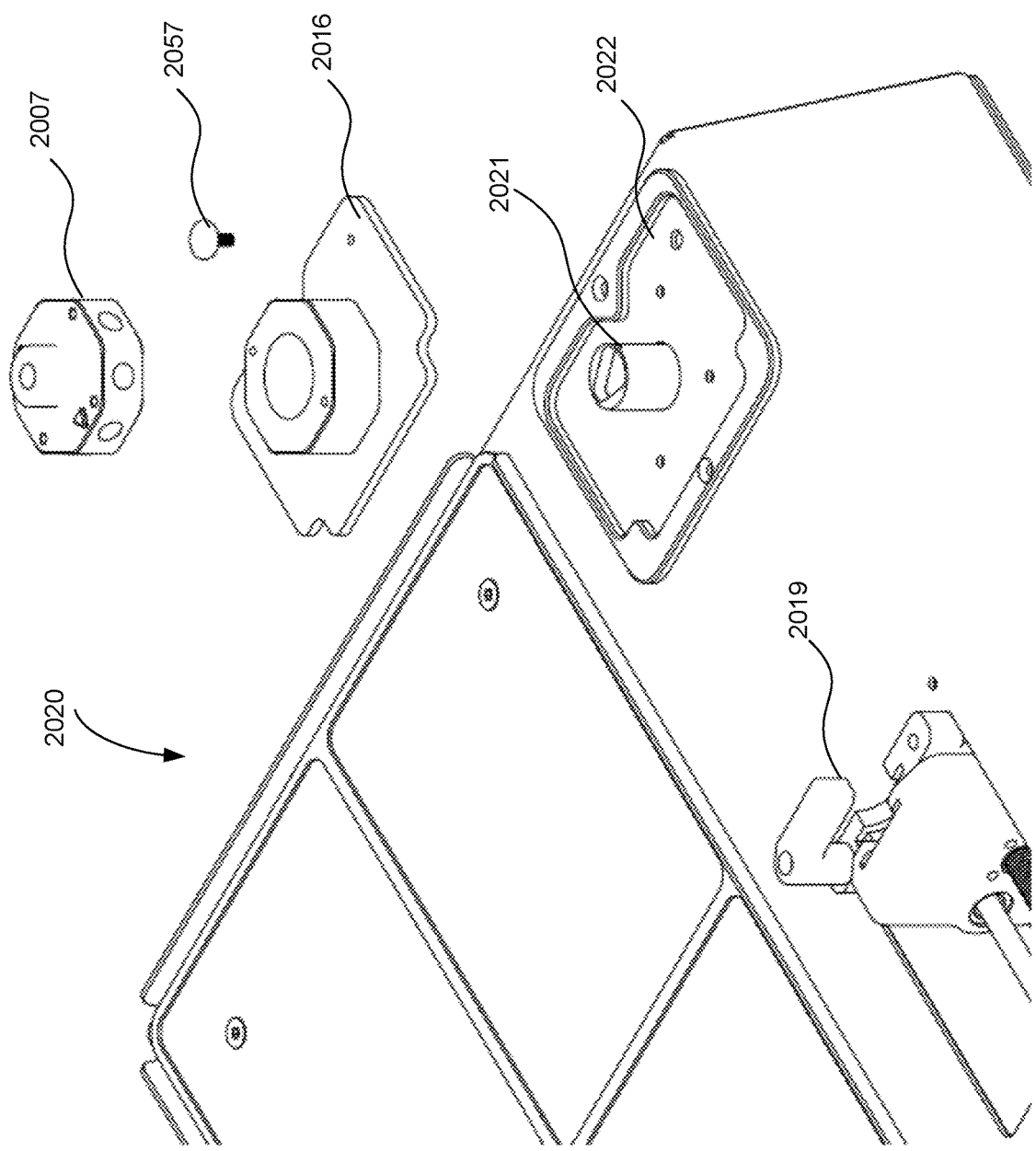
FIG. 41 is a partial exploded view of a portion of the base unit of FIG. 38, illustrating the multiport valve prior to being assembled to the base unit.

As described above for previous embodiments, the preassembled tray assembly 2001 can be removably coupled to the base unit 2020. FIGS. 38-44 illustrate the base unit 2020. The base unit 2020 includes a housing 2023, a pump actuator 2026 disposed partially within a recess or pocket 2025 of the housing 2023. The pump actuator 2026 (see, e.g., FIGS. 38-40) includes a pump holder 2019 to which the fluid pump 2013 can be locked in place and operatively connected to the pump actuator 2026. Although the pump holder 2019 is shown as slotted member that receives a syringe flange and a movable member to secure the syringe flange in place, in other embodiments, the pump holder 2019 can be any suitable structure or mechanism for securing the pump (which can be any suitable pump) to the pump actuator. The base unit 2020 also includes a valve connector 2022 configured to matingly couple to the multiport valve 2007 and a valve actuator 2021 configured to engage the multiport pump 2007 when coupled thereto. For example, as described above, when the tray assembly 2001 is coupled to the base unit 2020, the multiport valve 2007 can be uncoupled from the tray 2002 and coupled to the valve connector 2022 of the base unit 2020 such that the multiport valve 2007 operatively engages the valve actuator 2021 as shown in FIGS. 40 and 41. FIG. 41 is a partial exploded view illustrating the components of the multiport valve 2007 prior to being coupled to the valve connector 2022.

Figure 42:
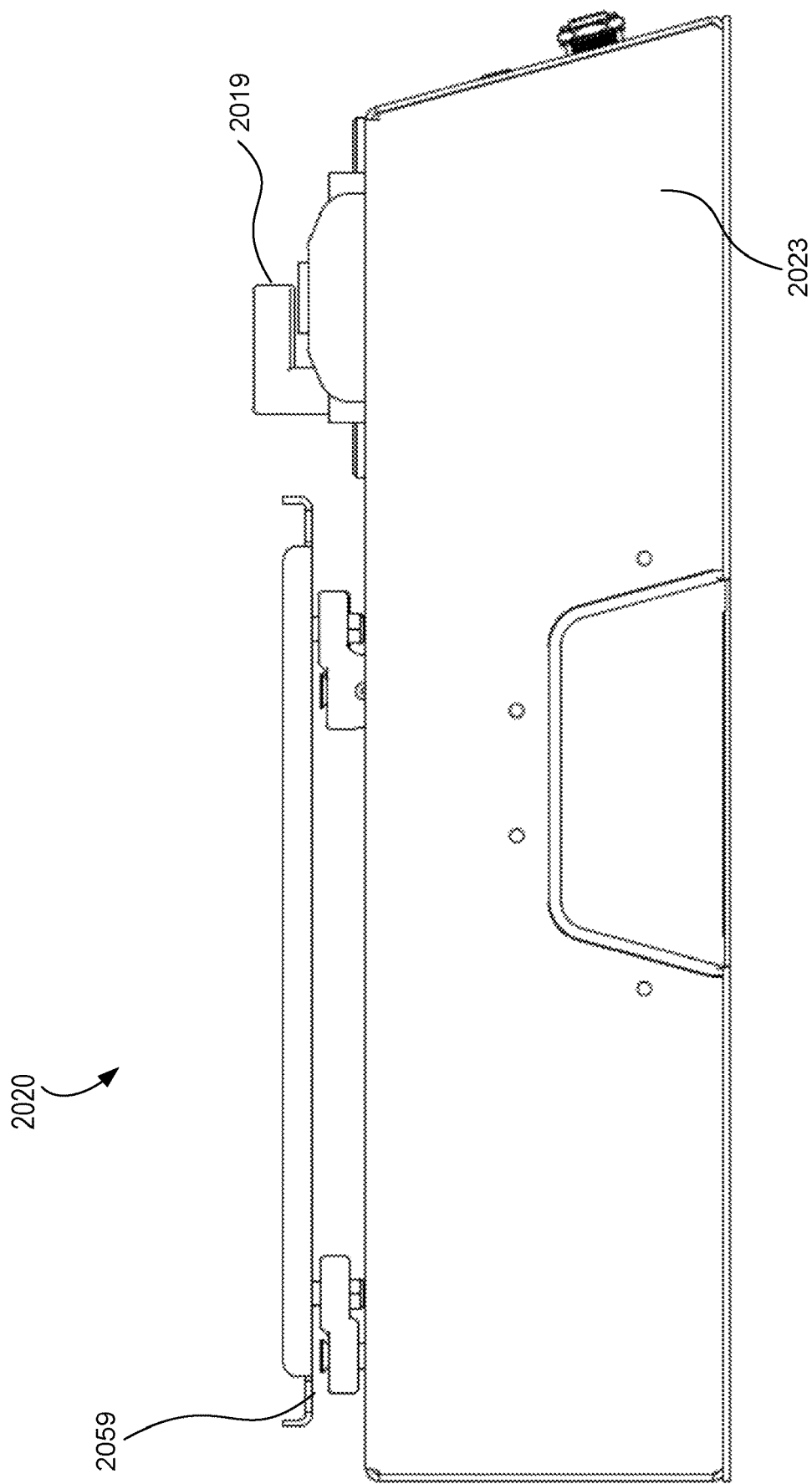
FIG. 42 is a side view of the base unit of FIG. 38.

In this embodiment, a support plate 2059 is coupled to the housing 2023 and provides a receiving portion 2024 on which the tray assembly 2001 can be placed. In this embodiment, the support plate 2059 is elevated above a top surface of the housing 2023. FIG. 42 is a side view illustrating the elevation of the support plate 2059. The support plate 2059 is coupled to an agitator 2028 (see FIG. 44) disposed within an interior of the housing 2023. As described above, the agitator 2028 can be used during a cell culturing procedure to agitate the tray assembly 2001 and the contents of the cell culture containers coupled thereto.

FIG. 40 illustrates the base unit 2020 with the syringe 2019 coupled to the syringe holder 2019 and the multiport valve 2007 coupled to the valve connector 2022. FIG. 40 also shows an optional mat 2070 disposed on the top surface of the support plate 2059. The mat 2070 can be, for example, a rubber mat configured to protect the surface of the support plate 2059 and/or provide dampening when the tray assembly 2001 is agitated by the agitator 2028. Similarly stated, in some embodiments, the support plate (or receiving portion) of a base unit can include a damping member that dampens any relative motion or contact between the support plate on the containers mounted thereto.

Figure 43:
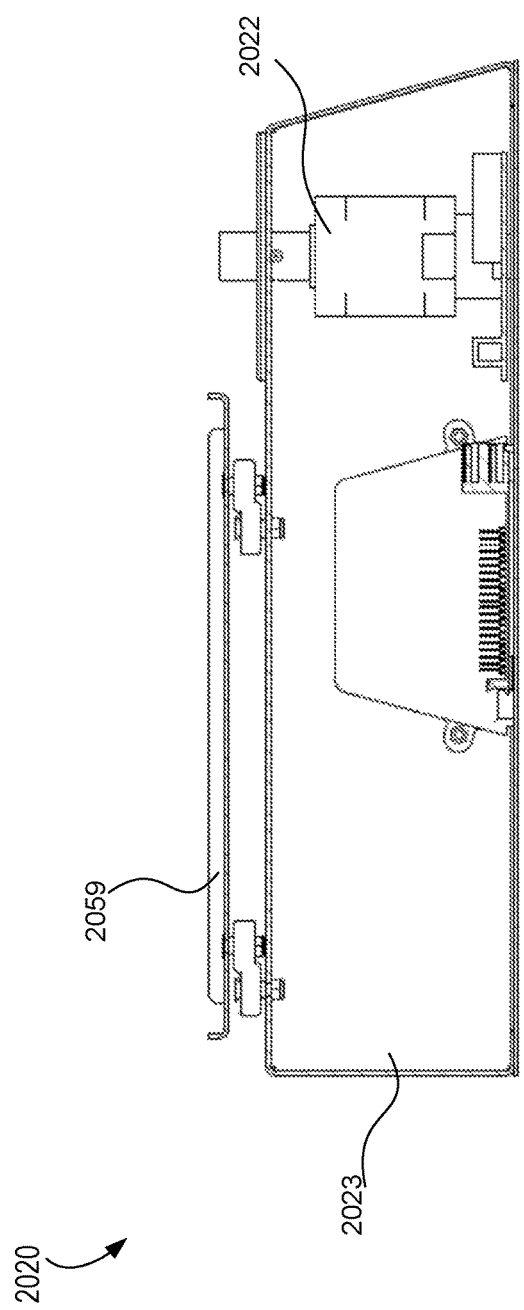
FIG. 43 is a side view and FIG. 44 is an opposite side view of the base unit of FIG. 38 illustrating the interior of the base unit.
Figure 44:
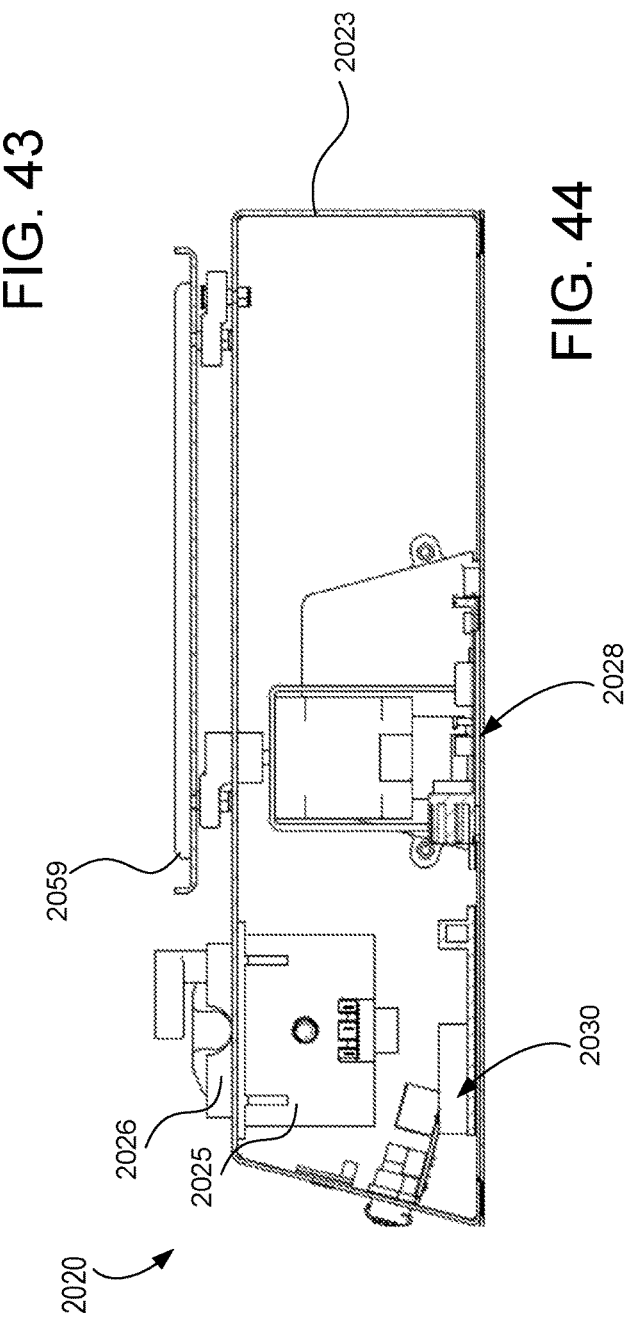
Figure 45:
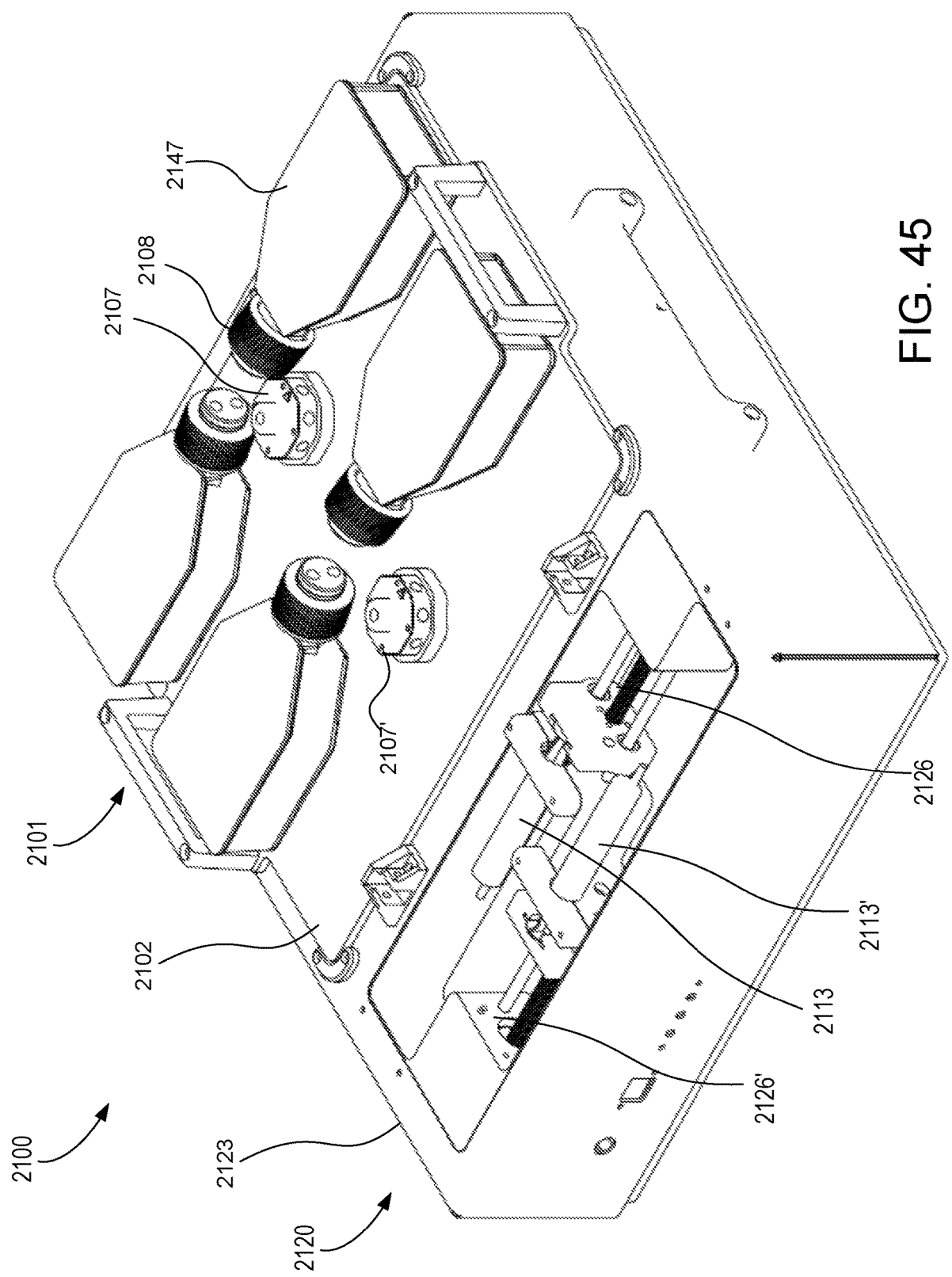
FIG. 45 is a perspective view of a cell culturing system, according to another embodiment.
Figure 46:
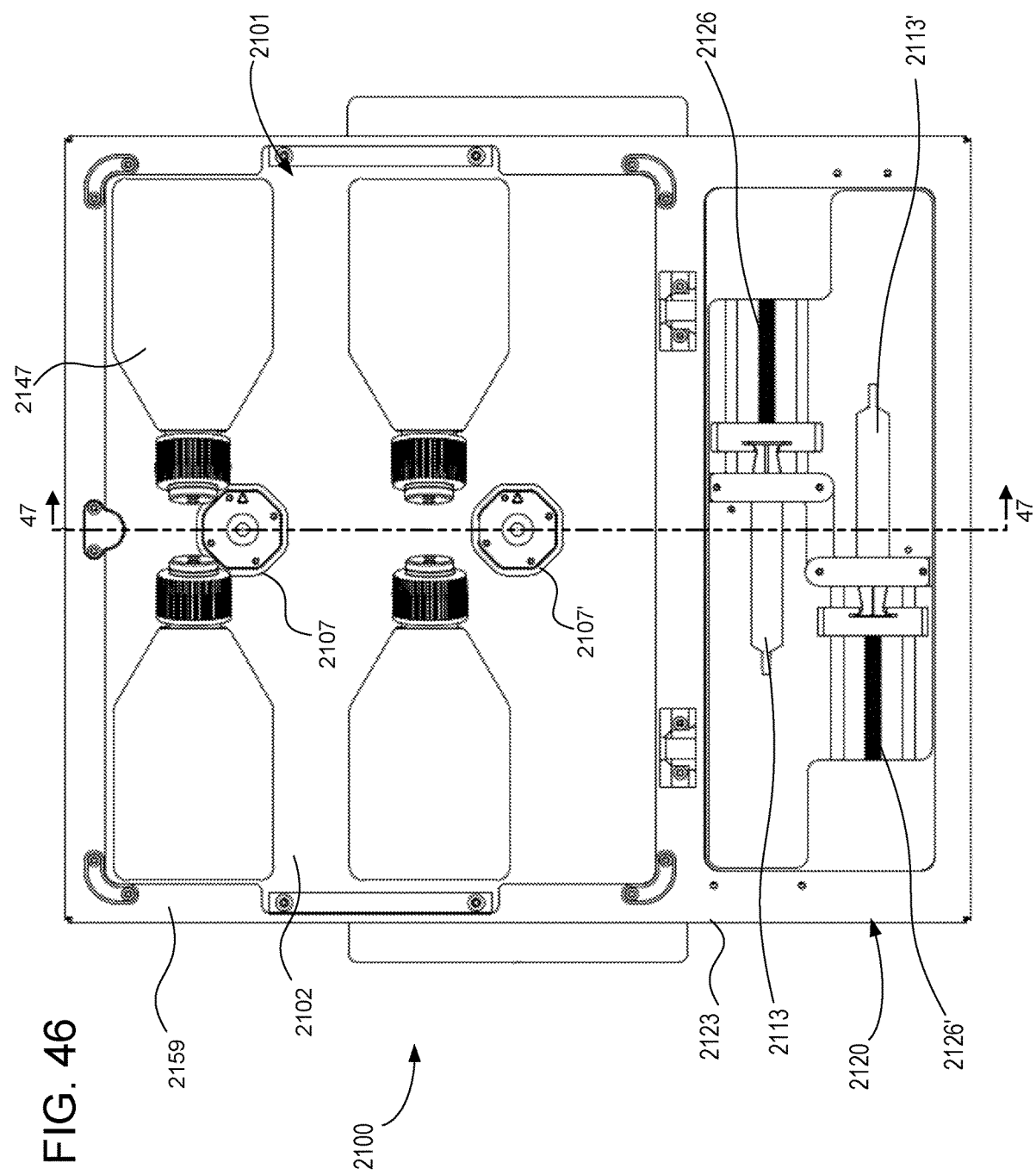
FIG. 46 is a top view of the cell culturing system of FIG. 45.

FIGS. 43 and 44 are opposite side views of the base unit 2020 showing the interior of the housing 2023. FIG. 43 shows the valve actuator 2022 and FIG. 44 shows the agitator 2028 and the pump actuator 2026 within the pocket 2025. Also shown in FIG. 44 is the electronic control system 2030. The electronic control system 2030 can be configured the same as or similar to and function the same as or similar to, the electronic control system 1630 described above. The electronic control system 2030 can optionally be capable of communicating with other computing devices and/or within a cloud computing environment and can include some or all of the components and features describe above with respect to FIG. 17. Although not shown, the system 2000 can also include one or more sensors and/or lights (e.g., microscope, imaging device, etc.), such as the microscope imaging device 1960 described herein.

FIGS. 45-51 illustrate another embodiment of a cell culture system that can be used in a cell culturing procedure. The cell culture system 2100 can include some of the same or similar components as other embodiments described herein and can have the same or similar functions as the previous embodiments described herein, and therefore, some details of the cell culturing system 2100 are not described with respect to this embodiment. In this embodiment, the cell culturing system 2100 does not include an agitator and includes two multiport valves/valve actuators, and two fluid pumps/fluid actuators.

The cell culturing system 2100 (also referred to herein as "system") includes a tray assembly 2101 and a base unit 2120. As shown, for example, in FIG. 45, the tray assembly 2101 includes a tray 2102 with two multiport valves 2107 and 2107', and four cell culture containers 2147 are shown disposed thereon. The containers 2147 can be preassembled on the tray assembly 2101 or added to the tray 2102 just prior to a cell culture procedure. For example, in some embodiments, the containers 2147 are preassembled on the tray 2102 as the tray assembly 2101 is provided within an overwrap. The preassembled containers can be coupled to or uncoupled from lids 2108 (described below) when disposed within the overwrap. During preparation for a cell culturing procedure, cells and reagent can be added to the containers, and the lids 2108 attached to the containers, prior to the tray assembly 2101 being coupled to the base unit 2120. In some embodiments, the containers 2147 are not preassembled on the tray 2102 (are not provided within the overwrap), but rather are added to the tray during preparation for the cell culture procedure, as described above. The containers are filled with cells and reagent (e.g., cell culture media), coupled to the lids 2108 and added to the tray assembly 2101.

The lids 2108 can be configured the same as the lids described above for previous embodiments, including the cell culture vessel lid 803 or the lid 2408. For example, the lids 2108 can include a liquid exchange port (also referred to as "fluid port") and a gas exchange port, and the fluid ports can be aseptically coupled to one of the multiport valves 2107, 2107' with tubing (not shown) as described above for previous embodiments. For example, two of the container 2147/lids 2008 can be fluidically coupled to the valve 2107 and two of the containers 2147/lids 2108 can be fluidically coupled to the valve 2107'. In this embodiment, the multiport valves 2107, 2107' are fixed to the tray 2102 and remain on the tray 2102 when the tray assembly 2101 is coupled to the base unit 2120. The multiport valves 2107, 2107 can each include a master port and multiple selectable ports to which the lids 2008 (and/or other lids/containers) can be selectively coupled via a length of tubing (not shown). The multiport valves 2107, 2107' can be coupled to the tray 2102 via a mounting portion (not shown) that matingly couples to and fits within a mounting pocket 2018 of the tray 2102.

Figure 47:
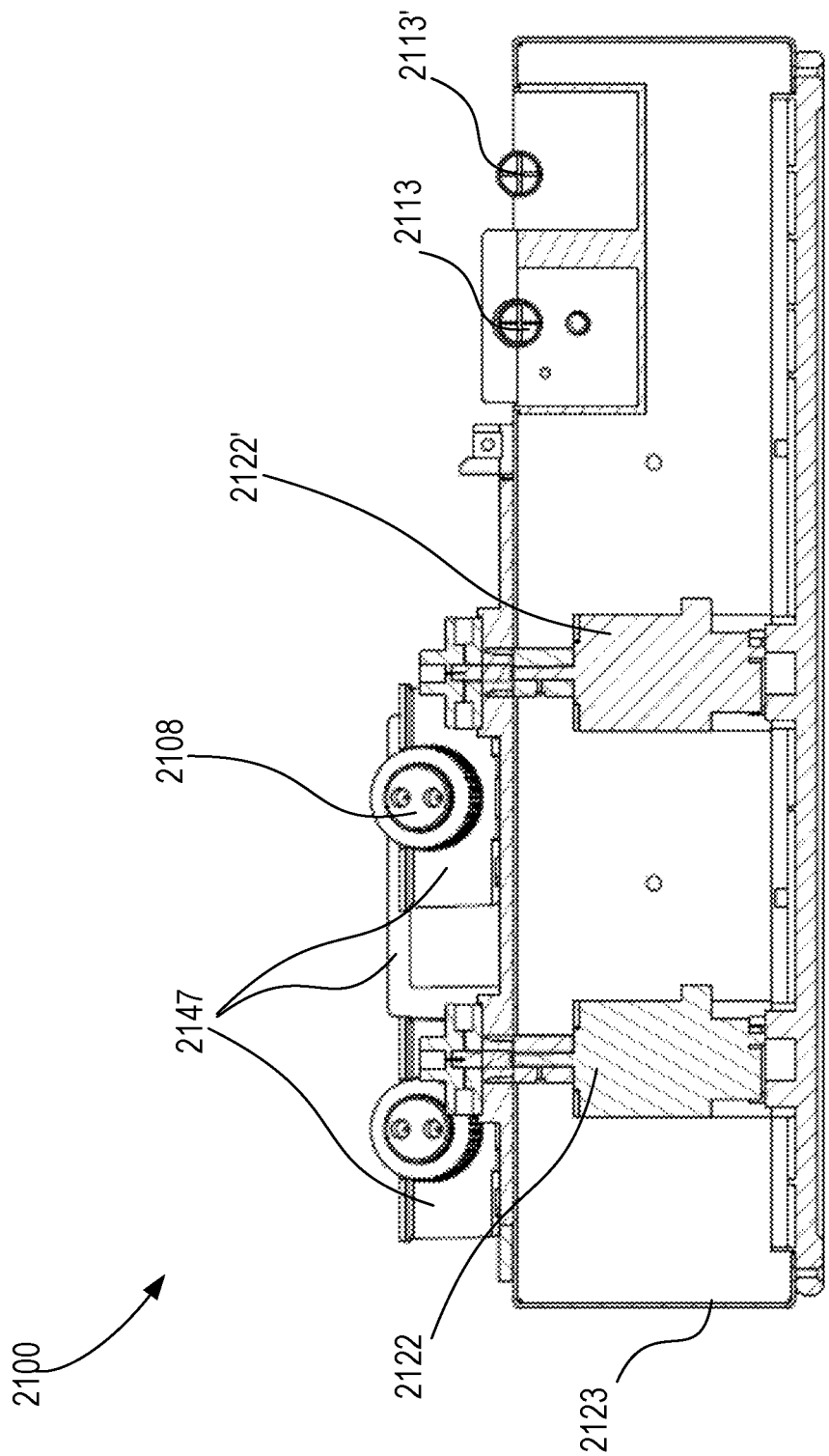
FIG. 47 is a cross-sectional view taken along line 47-47 in FIG. 46.
Figure 48:
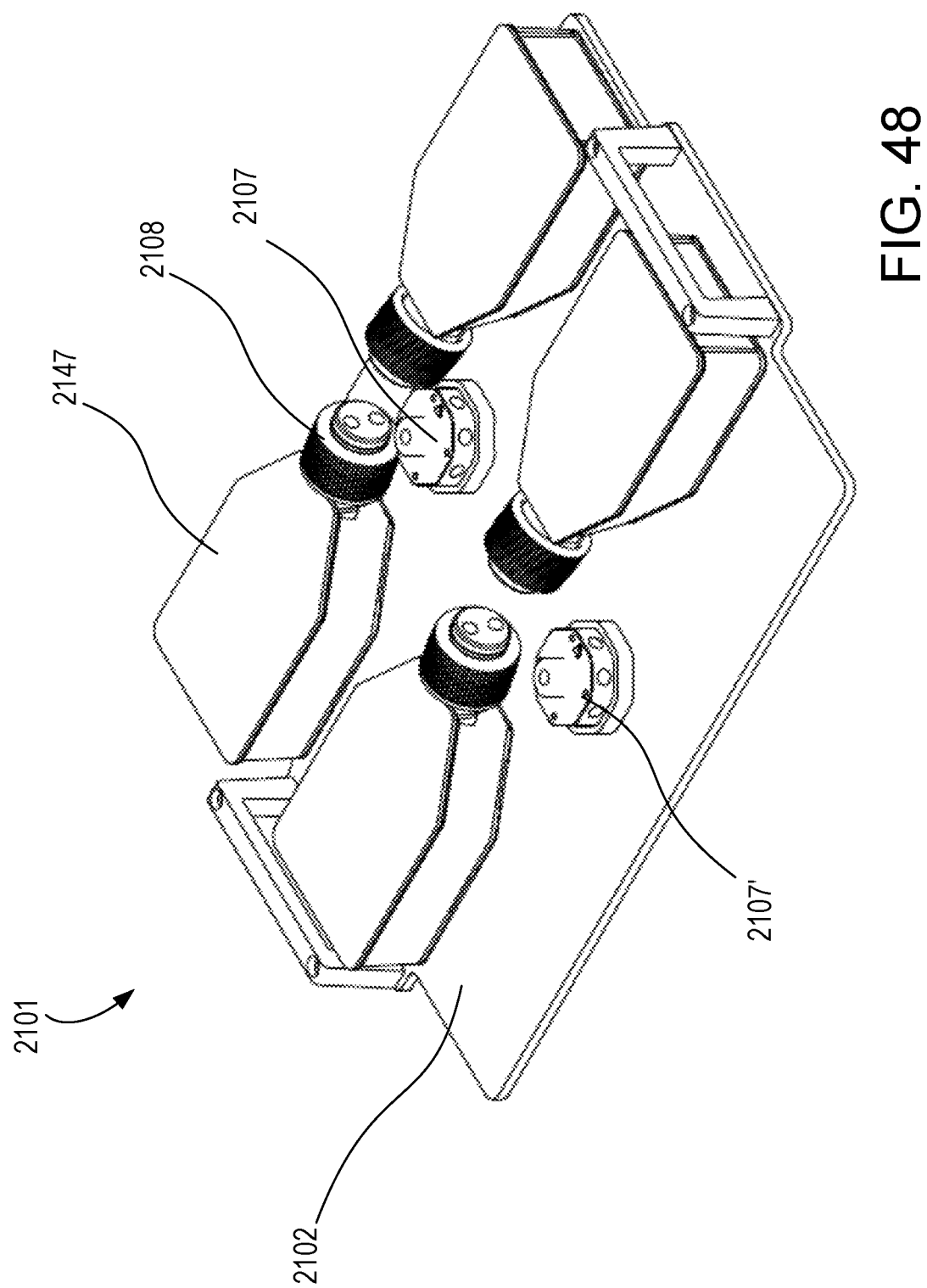
FIG. 48 is a perspective view of a tray assembly, according to an embodiment.
Figure 51:
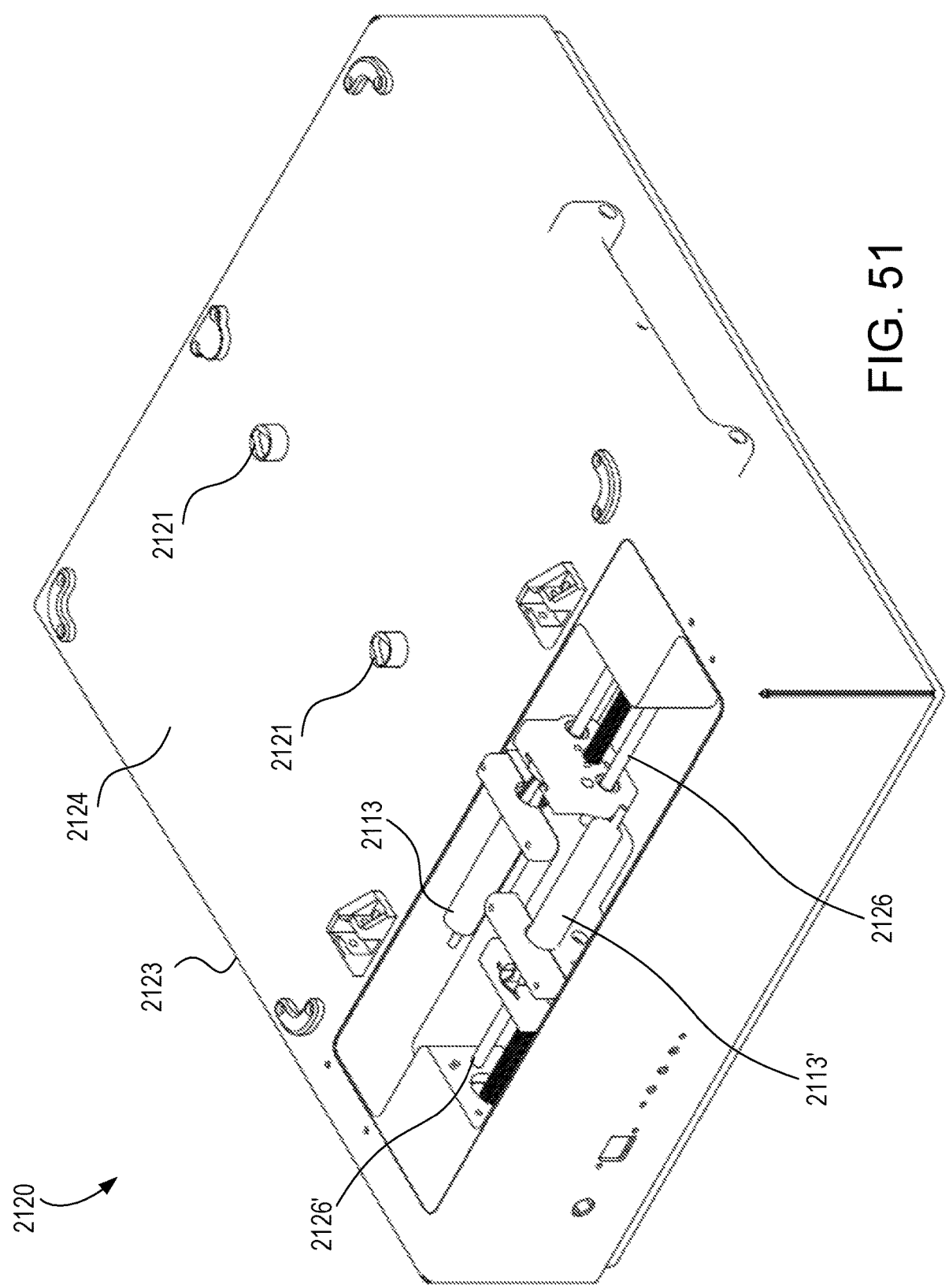
FIG. 51 is a perspective view of a base unit, according to an embodiment.

In this embodiment, the base unit 2120 includes a housing 2123 that defines a tray receiving portion 2124 and includes the two valve actuators 2122, 2122'. The valve actuators 2122, 2122' each include a valve connector portion 2171, 2171' that extends from a top surface of the base unit 2120 within the receiving portion 2124 as shown in FIG. 51. When the tray assembly 2101 is coupled to the base unit 2120, the multiport vales 2107, 2107' can operatively engage the valve actuators 2122 and 2122' of the base unit 2120 via the valve connector portions 2171 as shown in FIG. 47.

In this embodiment, the base unit 2120 also includes two fluid actuators 2126 and 2126' that are couplable to fluid pumps 2113 and 2113', respectively. The fluid pumps 2113, 2113' can be, for example, syringes, peristaltic pumps or another type of positive displacement fluid pump. The use of two pumps 2113, 2113' and two valves 2107 can provide for separate fluidic connections between the valves 2107, 2107' and the various containers of the system to allow; for example, separate fluid inputs and outputs to and from a particular container (e.g., containers 2147). For example, waste removal from one container can be separate from and not pass through the same fluidic channels as other fresh media. Two pumps can also allow for more inputs and outputs to the containers by replicating fluidics.

In this embodiment, the system 2100 does not include an agitator. Although not shown, the system 2100 can also include an electronic control system, one or more sensor (e.g., microscope, imaging device, etc.). The system 2100 can also include various other containers such as a waste container, reagent containers, cell harvest containers, etc., that can each be couplable to one of the multiport valves 2107, 2107".

FIGS. 52-58 illustrate another embodiment of a cell culture system that can be used in a cell culturing procedure. The cell culture system 2200 can include some of the same or similar components as other embodiments described herein and can have the same or similar functions as the previous embodiments described herein, and therefore, some details of the cell culturing system 2200 may not be illustrated and are not described in detail with respect to this embodiment. This embodiment illustrates an example cell culturing system that includes multiple separate tray assemblies that can each include lids and/or containers that can be fluidically coupled to a separate multiport valve and a separate fluid pump system. Said another way each tray assembly is fluidically coupled to its own multiport valve and fluid pump, but is fluidically isolated from the multiport valves and fluid pumps of the other trays. The separate tray assemblies can then be coupled to a single base unit. In some embodiments, each of the separate tray assemblies can be preassembled and disposed within a protective overwrap and shipped separately. In some embodiments, the separate tray assemblies can be preassembled and shipped together within a protective overwrap. By maintaining each of the tray assemblies in fluidic isolation from the other tray assemblies, the cell culture system is capable of culturing multiple different types of cells without the risk of cross-contamination. For example, each tray assembly can be configured for a different cell type. This embodiment also allows for more different types of cells to be cultured and incubated within a dimensionally smaller device. For example, with a multiple tray system as described below; the system can be used to grow three types of cells on a single shelf and/or within a single base unit of an incubator, without sharing fluidics between the three cell types. In some embodiments, a single, larger tray (the width of two or three of the smaller trays) can be used when desired to grow more of a single type of cell.

In this embodiment, the cell culturing system 2200 (also referred to herein as "system") includes a base unit 2220 and three tray assemblies 2201, 2201', 2201" that can be coupled to the base unit 2220 as described above for previous embodiments. The three tray assemblies (collectively referred to as tray assemblies 2201) and the base unit 2220 can include the same or similar features and components as described above for previous embodiments. This embodiment also includes three multiport valves 2207, 2207', 2207" (collectively referred to as multiport valves 2207) and three fluid pumps 2213, 2213', 2213" (collectively referred to as fluid pumps 2213).

In this embodiment, the tray assemblies 2201 can each include a tray 2202, 2202', 2202" (collectively referred to as trays 2202) (see e.g., FIG. 55), having a multiport valve 2207, 2207', 2207", a cell counting chip 2217, 2217', 2217" (collectively referred to as counting chips 2217), a first cell culture container 2247, 2247', 2247" (collectively referred to as cell culture containers 2247), and a second cell culture container 2248, 2248', 2248" (collectively referred to as cell culture containers 2248) disposed thereon. In this example embodiment, the containers 2247 are smaller than the containers 2248. It should be understood, however, that the tray assemblies 2201 can accommodate other sized containers not shown. In some embodiments, one or all of the tray assemblies 2201 can include the same two containers. The use of a larger container (e.g., 2247) and a smaller container (e.g., 2248) within the same tray assembly 2201 may be desirable, for example, to use for a cell expansion process. For example, the cells can be placed in the smaller container 2248 to promote better growth when there are fewer cells, and then the cells can be moved to the larger container as the growth surface of the smaller flask gets crowded during the expansion process. The use of the same sized containers within the same tray assembly 2201 may be desirable, for example, for a cell maintenance process, where a cell line is to be kept in culture for when it is next needed.

Figure 57:
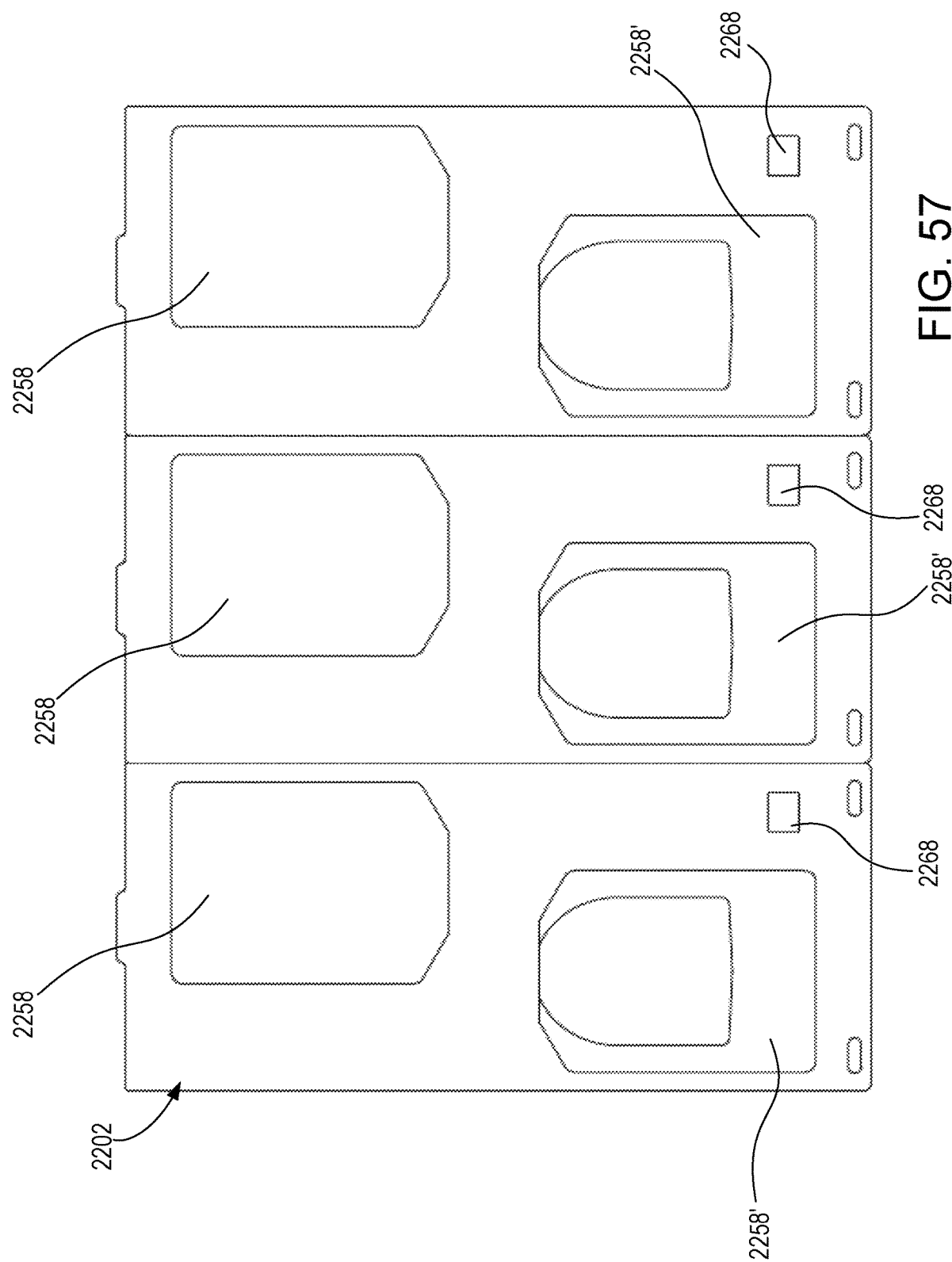
FIG. 57 is a top view of the tray of the tray assembly of FIG. 55.

The trays 2202 can include transparent portions or partial cut-outs 2258' and 2258", as shown in FIG. 57, on which the containers 2247 and 2248, respectively, can be disposed. As described above for previous embodiments, the transparent portions or partial cut-outs 2258, 2258' can provide for sensor data to be obtained associated with the cell culture containers 2247 and 2248. For example, an imaging device or other sensor can be movably disposed within the housing of the base unit 2220 (described below) and moved to a location below the transparent portions or cut-outs 2258, 2258'. As shown in FIG. 57, the transparent portions or cut-outs 2258' illustrate an optional container cradle that can accommodate two different sized containers. Similarly, the trays 2202 also include transparent portions or cut-outs 2268 at a location where the cell counting chips 2217 are disposed to provide for sensor data to be obtained associated with a sample fluid disposed on the cell counting chips 2217 as described above for previous embodiments.

The containers 2247 (and 2247', 2247") and 2248 (and 2248', 2248") can be preassembled on the trays 2202 or added to the trays 2202 prior to a cell culture procedure (e.g., in accordance with the methods described herein). For example, in some embodiments, the containers 2247 are preassembled on the tray 2202 and the tray assembly 2201 is provided within an overwrap (not shown, but similar to the overwraps described herein). The preassembled containers can be either coupled to or uncoupled from a lid 2208 (described below) within the preassembled tray 2202. During preparation for a cell culturing procedure, cells and reagent can be added to the containers 2247, 2248, and the lids 2208 attached to the containers 2247, 2248, prior to the tray assemblies 2201 being coupled to the base unit 2220. In some embodiments, the containers 2247 are not preassembled on the tray 2202 (are not provided within the overwrap), but rather are added to the trays 2202 during preparation for the cell culture procedure. The containers 2247, 2248 can be filled with cells and reagent, coupled to the lids and added to the tray assembly 2201.

The lids 2208 can be configured the same as the lids described above for previous embodiments. For example, the lids 2208 can include a liquid exchange port (also referred to as "fluid port") and a gas exchange port. The fluid ports can be aseptically coupled to one of the multiport valves 2207, 2207', 2207" with tubing (not shown) as described above for previous embodiments. For example, for each tray assembly 2201, the two containers 2247 and 2248 with lids 2208 coupled thereto can be fluidically coupled to a select port of the valve 2207 of that tray assembly 2201. The multiport valves 2207 can each include a master port and multiple selectable ports to which the lids 2208 (and/or other lids/containers) can be selectively coupled. The multiport valves 2207 can be coupled to the tray 2202 via a mounting portion (not shown) that matingly couples to and fits within a mounting pocket (not shown) of the trays 2202 in a puzzle-like manner, as described above for previous embodiments.

Figure 52:
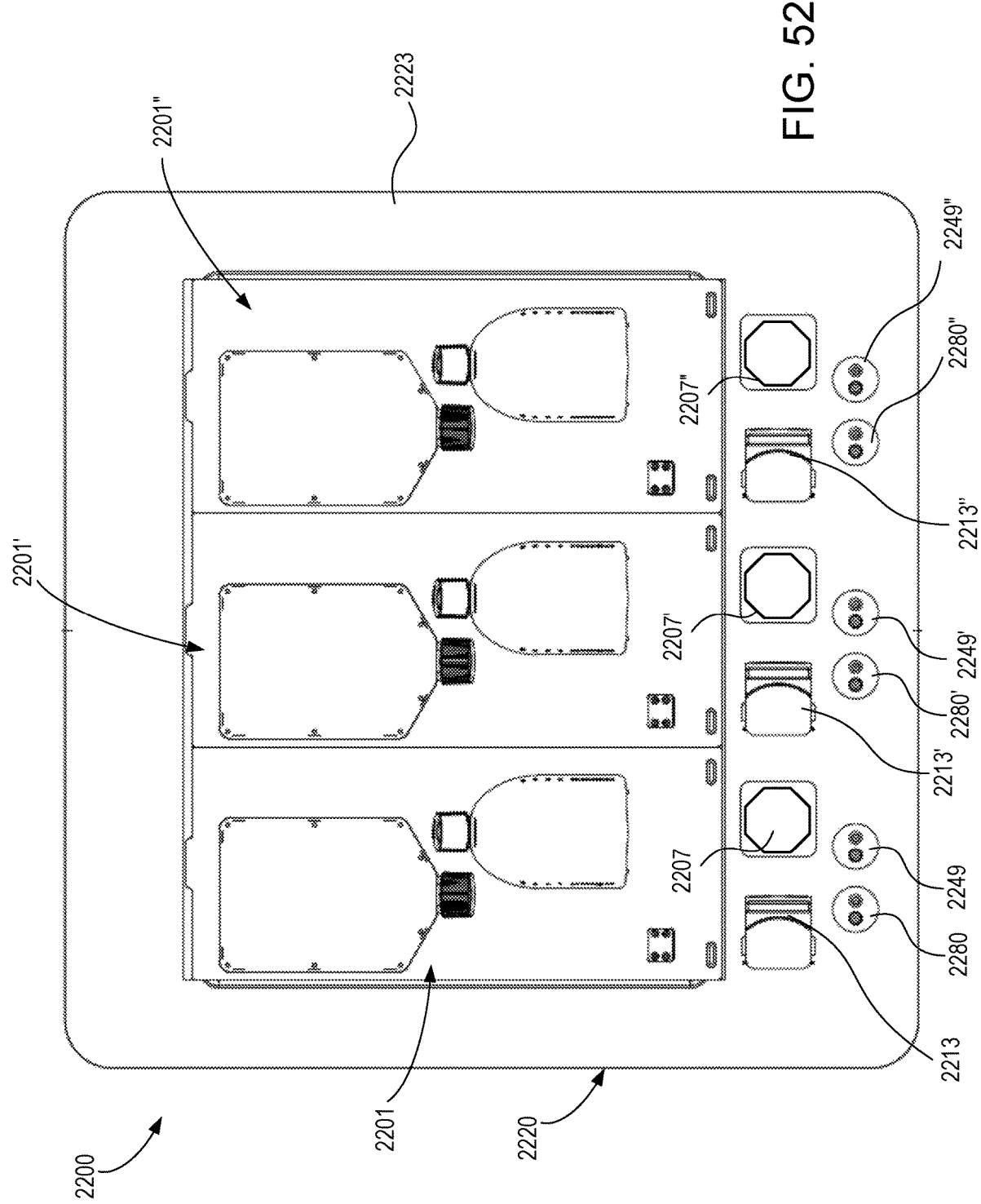
FIG. 52 is to view of a cell culturing system, according to another embodiment.
Figure 53:
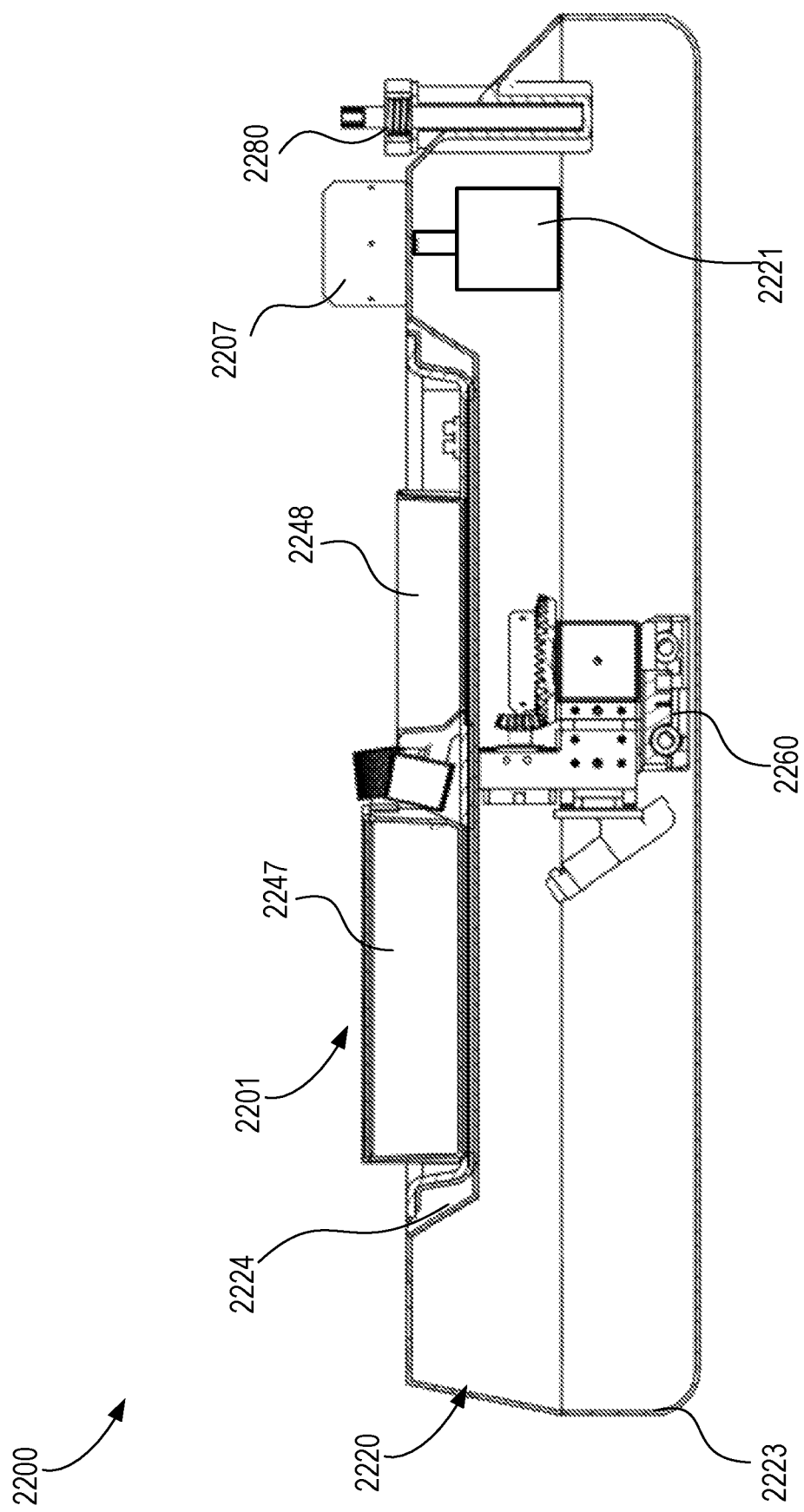
FIG. 53 is a side view of the cell culturing system of FIG. 52 illustrating an imaging system disposed within an interior of the base unit.
Figure 54:
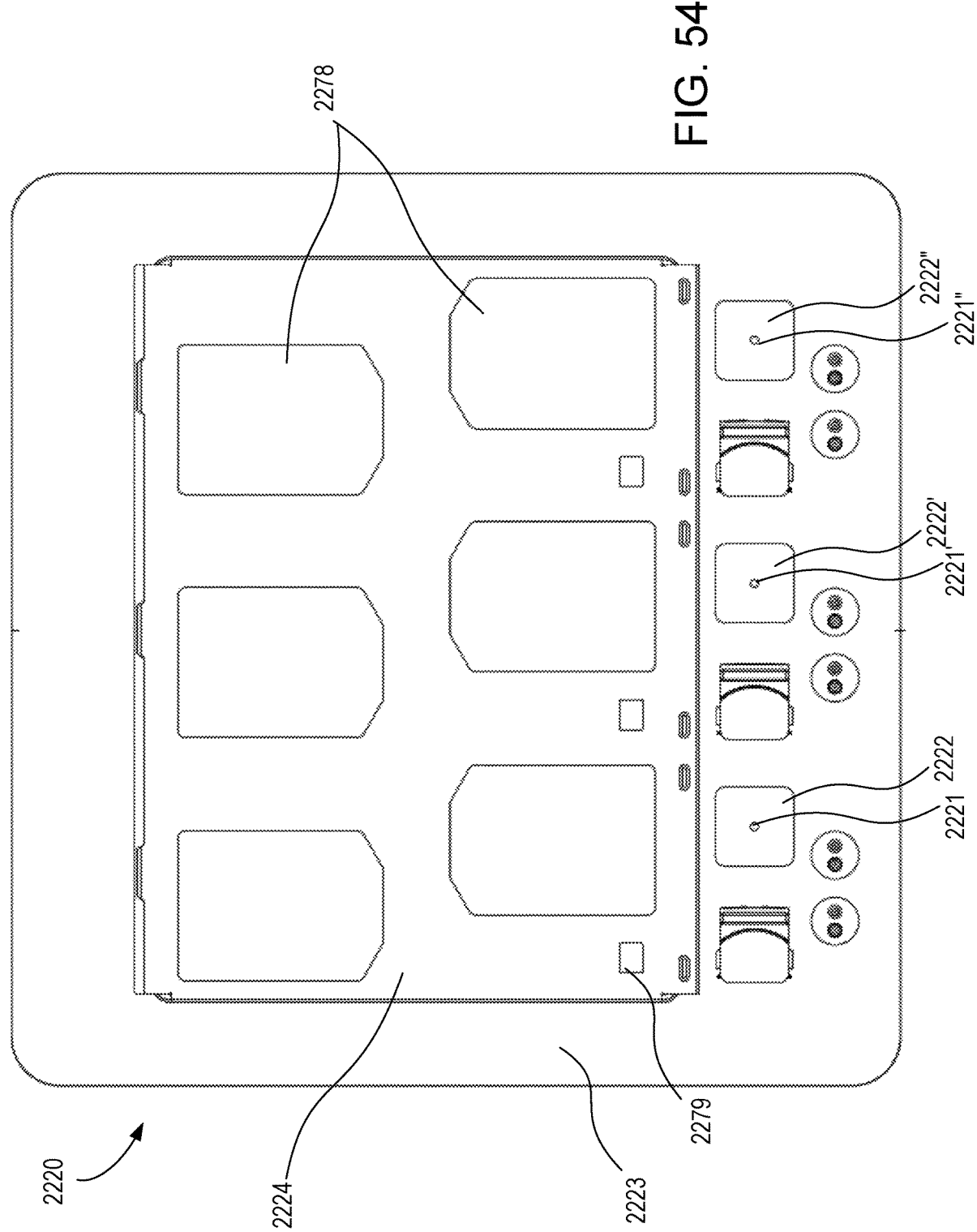
FIG. 54 is a top view of a base unit of the cell culturing system of FIG. 52.
Figure 55:
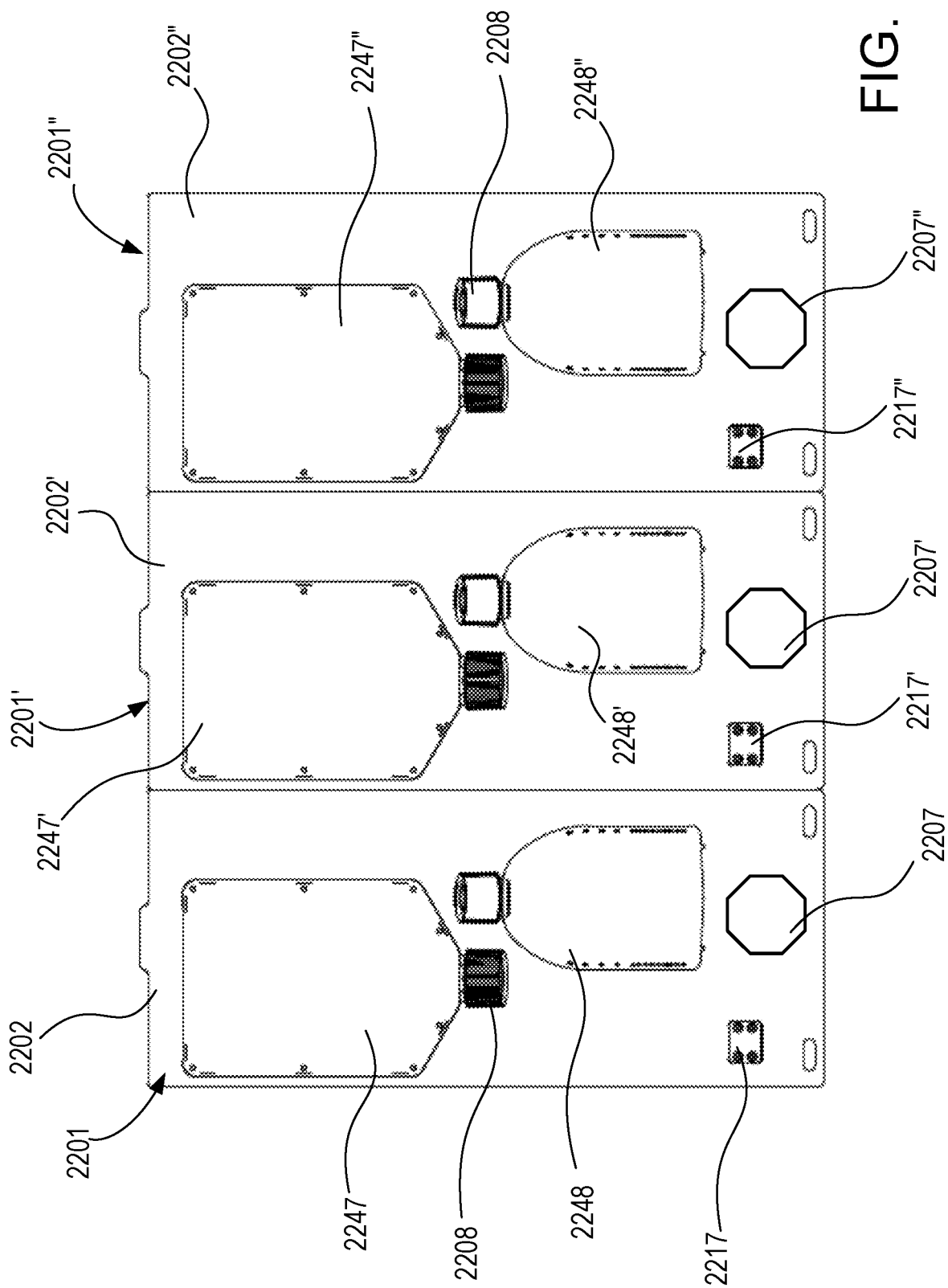
FIG. 55 is a top view of a tray assembly of the cell culturing system of FIG. 52.
Figure 56:
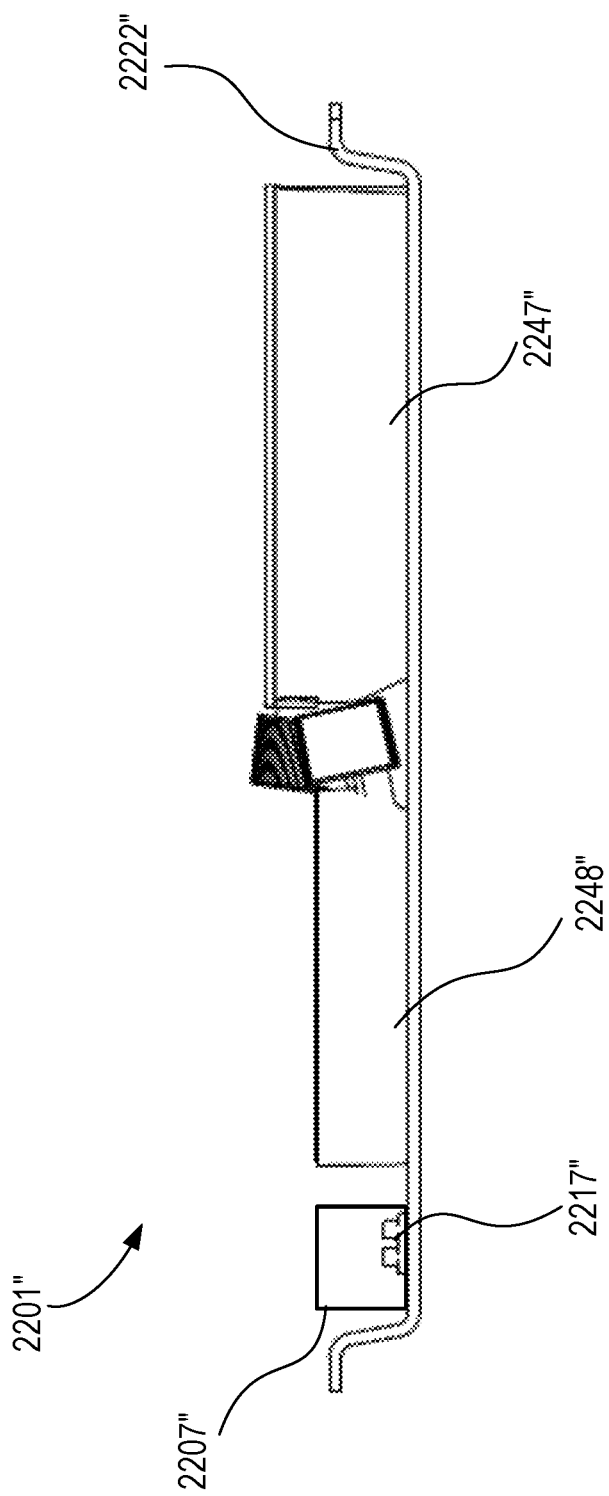
FIG. 56 is a side view of the tray assembly of FIG. 55.

In this embodiment, the base unit 2220 includes a housing 2223 that defines a tray receiving portion 2224 that can receive each of the three tray assemblies 2201. The housing 2223 also defines sections 2278 that can be transparent portions or cutouts that correspond to the transparent portions 2258 of the tray assemblies 2201. The housing 2223 also defines sections 2279 that can be transparent portions or cutouts that correspond to the transparent portions 2268 of the tray assemblies 2201 where the cell counting chips 2217 are located. As shown in FIGS. 52-54, the base unit 2220 can also optionally include multiple vials or vessels 2280 and multiple vials or vessels 2249. The vessels 2280 (2280', 2280") can be, for example, a holding vessel for an associated fluid pump 2213. For example, the fluid pumps 2213 can be, for example, peristaltic pumps, and the vessels 2280 can each serve as a holding vessel for one of the pumps such that the pump can function similar to a syringe type pump. More specifically, the vessel 2280' can be a holding vessel for the fluid pump 2213", and the vessel 2280" can be a holding vessel for the fluid pump 2213'". The holding vessels 2280 can receive a volume of fluid from a first location within the system where it is held until the pump is actuated to move the volume of fluid to a second location within the system. The vessels 2249 (2249', 2249") can be used to hold various other fluids that can be fluidically coupled to one of the separate fluid systems via one of the multiport valves 2207 (2207, 2207"). For example, the vessels 2249 can be used for waste, or to hold a fluid (e.g., a reagent) to warm the fluid after it has been refrigerated. For example, it may be desirable to refrigerate a container (or vessel) to keep the media therein at a desired temperature (e.g., 4 degrees Celsius). The media can be pumped from the refrigeration to a vessel, such as vessels 2249, such that the media can passively heat up to, for example, 37 degrees Celsius due to the temperature of the incubator in which the system 2200 is disposed.

Each tray assembly 2201 (2201', 2201"), when coupled to the base unit 2220, can be fluidically coupled to one of the fluid pumps 2213 (2213', 2213") to provide a separate closed fluid flow system. As described above, when the tray assemblies 2201 (2201, 2201") are coupled to the base unit 2220, the multiport valves 2207 (2207, 2207") can operatively engage valve actuators 2221, 2221', 2221"(collectively referred to as valve actuators 2221) of the base unit 2220 via the valve connector portions 2222, 2222' and 2222" (collectively referred to as valve connectors 2222), respectively. More specifically, in this embodiment, the multiport valves 2207 are removably coupled to the trays 2202 and can be coupled to a separate valve connector 2222 (2222, 2222") (see, e.g., FIG. 54) and valve actuator 2221 (2221', 2221") of the base unit 2220 as described above, for example, for multiport valve 2007. The fluid pumps 2213 can each be fluidically coupled to the master port of the corresponding multiport valve 2207. The fluid pumps 2213 (2213', 2213") can each be coupled to a pump actuator (not shown) within or coupled to the housing 2223 of the base unit 2220. Although the fluid pumps 2213 are described as peristaltic pumps, the fluid pumps 2213, can be other types of fluid pumps, such as syringes or another type of positive displacement fluid pump.

As shown in FIG. 53, the cell culturing system 2200 also includes an imaging device 2260 movably disposed within the housing 2223 such that it can be moved to locations aligned with the sections 2278 and 2279. The imaging device 2260 can be, for example, a microscope mounted to a gantry system to provide movement of the imaging device in multiple directions (similar to the microscope imaging device 1960 described above). Although not shown for this embodiment, the cell culturing system 2200 can also include an agitator, an electronic control system, and one or more additional sensor(s) (e.g., in addition to the imaging device 2260), as described herein.

In some embodiments, a single imaging device (e.g., 2260) and/or single agitator can be used to image cells on all three tray assemblies 2201. In some embodiments, separate imaging devices and/or separate agitators can be used for each tray assembly. The system 2200 can also include various other containers such as a waste container, reagent containers, cell harvest containers, etc., that can each be couplable to one of the fluidic systems via the multiport valves 2207, 2207, 2207". The cell culturing system 2200 can also include various couplers or coupling portions for holding cell culture containers (e.g., 2003, 2103) and holders for holding other containers, such as waste and reagent containers (e.g., 2005, 2006).

FIG. 58 illustrates an example of two incubators 2275 stacked on top of each other, and in which multiple cell culturing systems 2200 (i.e., tray and base unit) can be placed for a cell culturing procedure. As shown in FIG. 58, in this embodiment, three cell culturing systems 2200 can be placed on shelves within each incubator 2275.

Figure 59:
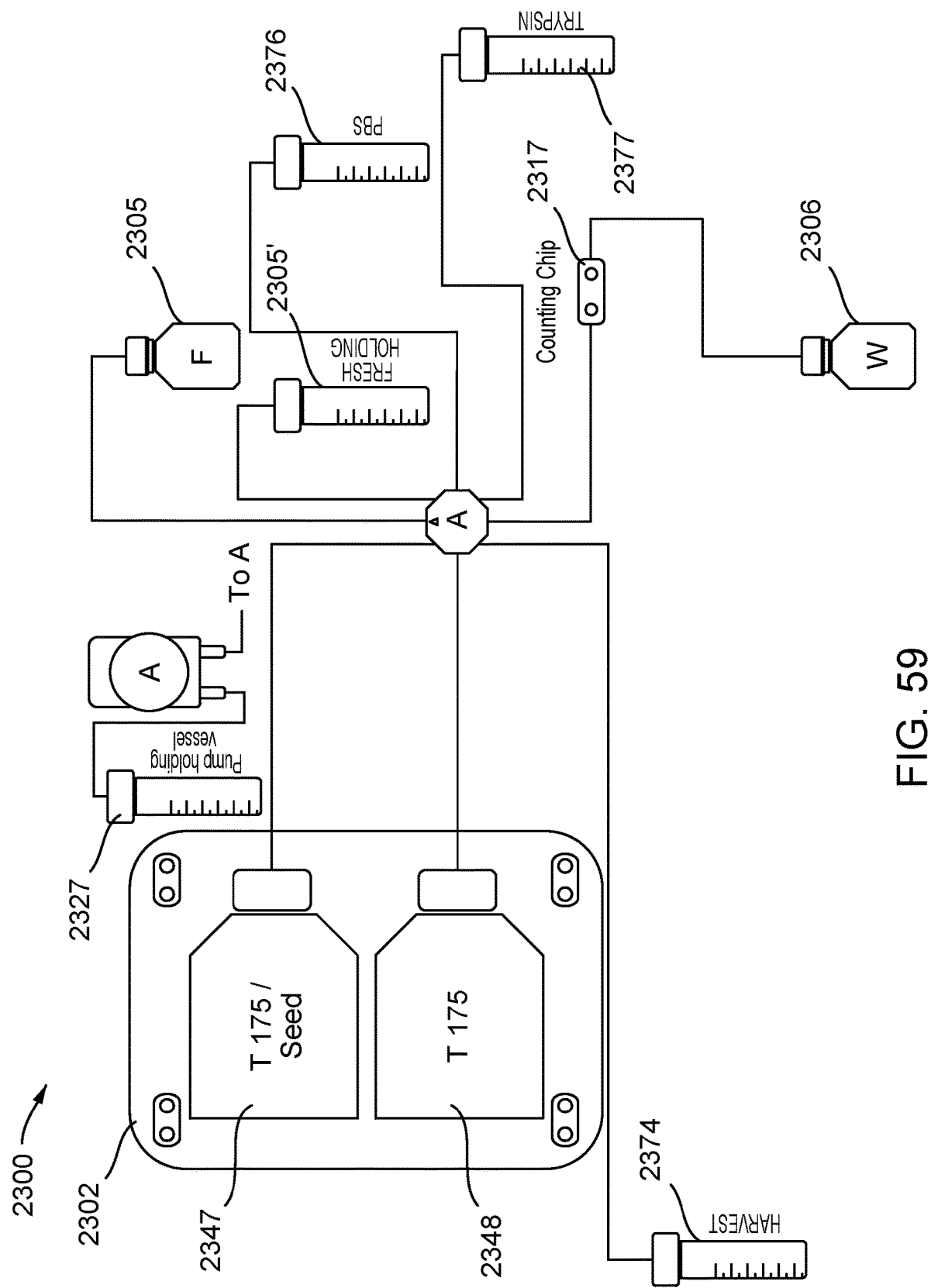
FIG. 59 is system diagram illustrating an example fluidic setup within a system during a cell culturing procedure.

FIG. 59 is a system diagram illustrating an example fluid flow within a system during cell culturing procedures and the various containers and other components that can be coupled within a cell culturing system as described herein. Thus, the system diagram is described with respect to various components of a cell culturing system 2300, but it should be understood that this example diagram can apply to any of the embodiments described herein.

FIG. 59 illustrates a tray 2302 with two cell culture containers 2347 and 2348 coupled thereto. The cell culture containers 2347 and 2348, and a cell counting chip 2317 are each fluidically coupled to a select port of a multiport valve 2307. A fluid pump with fluid holding vessel 2327 is fluidically coupled to a master port of the multiport valve 2307. Multiple other containers are also fluidically coupled to the multiport valve 2307 including reagent containers 2305 and 2305', a cell harvest container 2374, a waste container 2306, a container 2376 containing a cell buffer (e.g., PBS) and a container 2377 containing an enzyme (e.g., Trypsin).

During a cell culturing procedure, the pump holding vessel holds fluid solutions that are pumped in from a starting location (e.g., a reagent container 2305, 2305') within the system, the valve 2307 selects a destination channel (e.g., one of the containers 2347, 2348), and then the solution is pumped to that location. An isotonic and nontoxic buffer solution (e.g., PBS) is used for washing out components that get reused, such as, for example, the pump holding vessel. As shown in the supporting Table 1 in FIG. 60, in this example, the container 2305 can first be placed in a refrigerator to maintain the media within the container 2305 at a desired temperature (e.g., 4 degrees Celsius). Media from the container 2305 can then be pumped prior to a procedure (e.g., an hour before) into 2305' so that it can passively heat up to about 37 degrees Celsius due to the temperature in the incubator. For detaching cells, e.g., during passaging or harvesting, media can first be pumped out of the cell culture containers (2347, 2348) from which the cells are to be detached and pushed to waste. A buffer (e.g., in 2376) can be added to the cultures combined with optional agitation to wash the cells, and then the buffer removed from the culture and pushed to waste. The enzyme (e.g., in container 2377) can be pumped into the relevant cell culture containers, left for a while with optional agitation to aid the detachment, and then the solution diluted with fresh media (e.g., from 2305') to quench the enzyme, and then the cell suspension is passaged/harvested/with the enzyme diluted in the mixture. FIGS. 61A and 61B include a Table 2, which includes an example of a cell passaging procedure for maintaining an adherent cell line, listing for each step, the source for the fluid, the destination, the type of fluid and the volume within each of the cell culturing containers during the procedure. Although specific procedures are outlined in FIG. 61, the system 2300 can be used to perform any of the methods for cell culturing described herein (including the methods described above with reference to FIGS. 12-14).

Figure 62C:
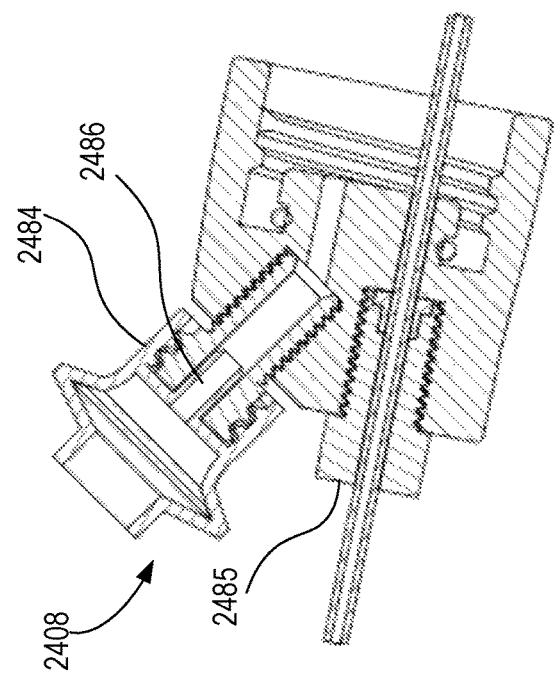
FIGS. 62A-62C illustrate a container lid according to an embodiment.
Figure 62A:
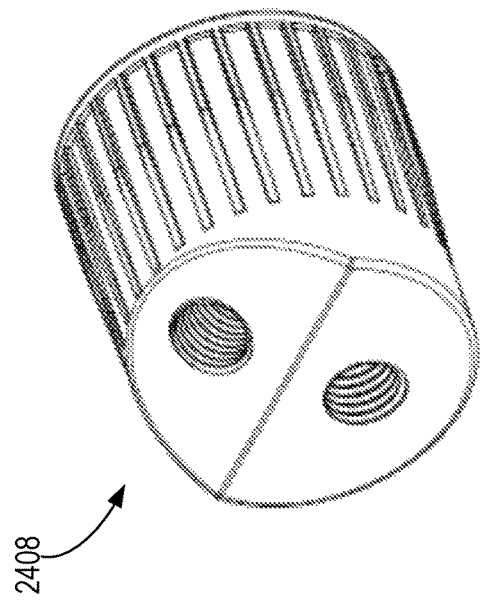
Figure 62B:
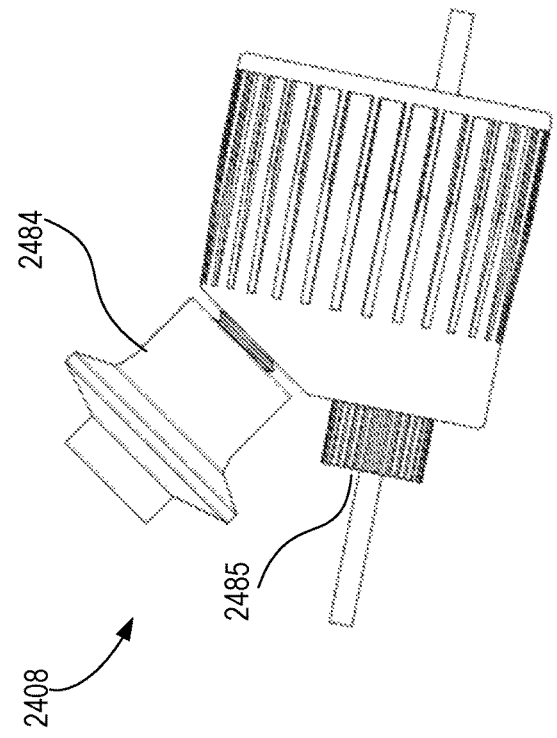

FIGS. 62A-62C illustrate container/vessel lid 2408 according to an embodiment.

The lid 2408 can be used in any of the embodiments of a cell culture system described herein. The lid 2408 can be screwed on to the mouth of a cell culture container or other container as described herein such that the lid 2408 engages with the threads of the mouth of cell culture container. In this example embodiment, the lid 2408 has a liquid port 2483 and a gas port 2484. A liquid channel 2485 is threadedly engaged with the liquid port 2483. A gas filter 2486 (see FIG. 62C) is threadedly engaged with gas port 2483. Gas filter 2486 may allow gas exchange in and out of the cell culture container while blocking any microbes or pathogens from entering the cell container. In an embodiment, the gas filter 2486 is a 0.22 micron filter.

Figure 64A:
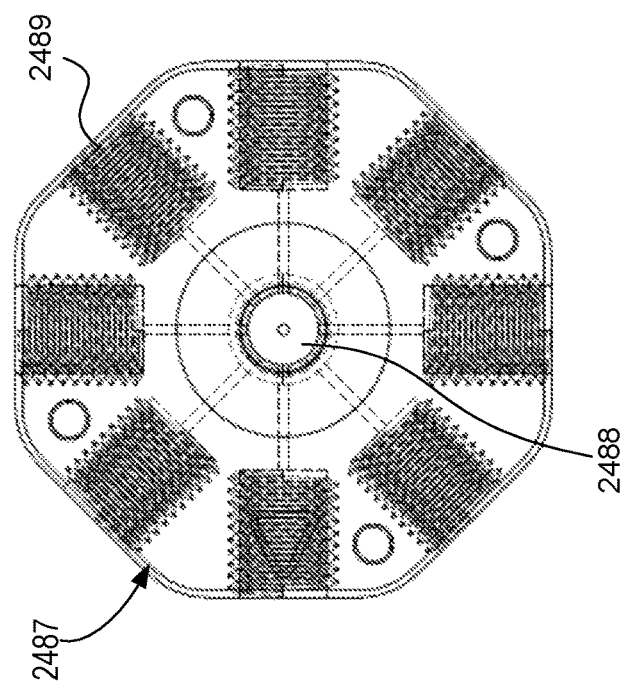
FIG. 64A is a cross-sectional view of the valve body of the multiport valve of FIGS. 63A-63D.
Figure 64C:
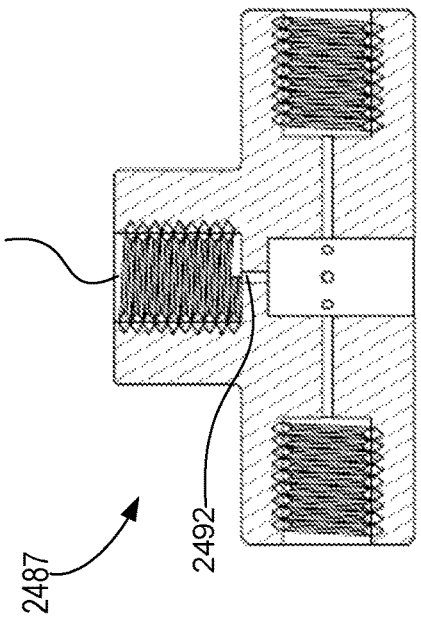
FIG. 64B is a side view and FIG. 64C is a cross-sectional side view of the valve body of FIG. 64A.
Figure 64B:
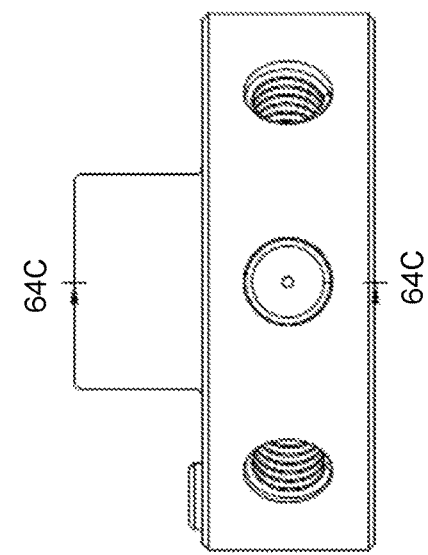

FIGS. 63A-63D illustrate an example embodiment of a multiport valve 2407 according to an embodiment. The multiport valve 2407 can be used in any of the embodiments of a cell culturing system described herein. In this embodiment, the multiport valve 2407 includes a valve body 2487 having a master port 2488 on a top side and multiple selectable ports 2489 dispersed around its circumference of the valve body 2487 (see, e.g., FIGS. 64A-64C).

The valve body 2487 has a cylindrical cavity on its underside to which a rotatable cylindrical valve rotor 2490 is inserted. Within rotatable cylindrical valve rotor 2490 is a fluid channel 2491 (see FIGS. 65A-65C). Within the valve body 2487 is a fluid channel 2492, which fluidly connects the master port 2488 to the fluid channel 2491 of the valve rotor 2490. The connection between fluid channel 2492 and fluid channel 2491 allows for the master port 2488 to be selectively fluidly connected to one of the side ports 2489 via rotation of the valve rotor 2490 (and therefore the fluid channel 2491). The valve rotor 2490 includes a mechanical coupler 2493 (see FIG. 65C), which is configured to mechanically couple to a valve actuator of the system, which can have a cavity shaped to accept the mechanical coupler 2493 and transfer rotational mechanical energy to the multiport valve 2407.

The multiport valve 2407 can be made of any appropriate material, and the valve body 2487 and valve rotor 2490 may be made of the same or different materials. Examples of materials that may be used include plastics, TFE-based materials such as polytetrafluoroethylene PTFE, metals, rubbers, or similar materials. In some embodiments, the valve body 2487 and valve rotor 2490 may be machined to fit with very close tolerances so that a fluid-tight seal is created between the two components. In some embodiments, additional gaskets, bearings, seals, and/or flanges may be incorporated into multiport valve 2407 to provide for a fluid-tight connection between valve body 2487 and valve rotor 2490.

As described for some of the embodiments herein, holders and/or couplers are provided on the tray assembly (e.g., for waste and/or reagent containers) for example, for transport purposes, then the containers are removed and placed in the incubator (e.g., waste container) or in a refrigerator (e.g., reagent container). In some embodiments, the cell culture containers are provided after the overwrap is removed from a tray during preparation for a cell culturing procedure. In some embodiments, the cell culture containers can be provided with the tray assembly within the overwrap (i.e., preassembled on the tray). For example, a sterilization method (e.g., an ethylene oxide) can be used to sterilize the tray with the cell culture containers connected.

In some embodiments, rather than adding the cells to a cell culture container within an aseptic environment (e.g., laminar flow hood), in some cases, the cells can be added outside of the hood. For example, a lid can be provided with an aseptic connector, such as, a septum-style connector on it. The lid can include a first portion of the aseptic connector, (e.g., the female or male portion) and a vial of cells can include a second portion of the septum connector (e.g., the other of the male or female portion). The vial of cells (e.g., defrosted cells) can be, for example, in the flow hood. The second portion of the connector of the vial can then be connected to the first portion of the aseptic connection of the lid, which can be disposed on a tray assembly within an incubator, or at a location outside the flow hood. Thus, the vial of cells can be coupled to the tray assembly outside the aseptic environment. In some embodiments, the lid with the septum could be put on the vial of cells before the cells are frozen. In some situations, a specialized "freezing medium" can be added to the vial before the cells are frozen in order to ensure the cells don't get burst by ice crystals during freezing. In another example, in some embodiments, cells are harvested on the system by transferring the cell suspension from a flask/container into a vial with a lid with a septum connection on it. For example, in some embodiments, the tray assembly can be shipped with a detachable harvesting vessel, which can have a lid with an aseptic connector as described above. After the cells have been harvested, the aseptic connection can then be disconnected and the vial removed from the tray assembly. Although not shown and described above for specific embodiments, lids and containers/vessels with septum-style connectors as described above can be used in any of the embodiments of a cell culturing system described herein.

In some embodiments, a cell culturing system as described herein can be self-incubating. In other words, the base unit can enclose and incubate the tray. For example, the system can include an enclosure with a heater, and appropriate gas and humidity control. Such a system can include temperature sensors, CO2 and/or O2 sensors, a humidity sensor and an electronic control system that includes a temperature module, gas modules, and a humidity module to monitor and control the functions of the incubator.

Some portions of the preceding detailed descriptions have been presented in terms of algorithms and symbolic representations of operations on data bits within a computer memory: These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general-purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general-purpose systems may be used with programs in accordance with the teachings herein, or it may prove convenient to construct a more specialized apparatus to perform the method. The structure for a variety of these systems will appear as set forth in the description below: In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape: optical storage media such as Compact Disc/Digital Video Discs (CD/DVDs), Compact Disc-Read Only Memories (CD-ROMs), and holographic devices: magneto-optical storage media such as optical disks: carrier wave signal processing modules: and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

A number of embodiments have been described. Nevertheless, it will be understood that various modifications may be made without departing from the spirit and scope of the invention. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above. Any of the components and sub-components described herein can be included in any of the embodiments unless mutually exclusive. For example, in some embodiments, an agitator, an electronic control system, sensors, lights, various containers, etc. are not shown or described, but it should be understood that any embodiment can include one or more of these components and/or features.

As another example, although the cell culture systems are described above as including a multiport valve, in some embodiments, a cell culture system may not include a multiport valve as described herein, but instead include one or more single port valves. For example, in some embodiments, a cell culture assembly can include a set of single port valves that control the flow into or out of each container and/or lid. The set of single port valves can be connected to a central pump by a manifold or other connected. The single port valves can be, for example, pinch valves (that pinch the tubing coupling a container to another element in the system), a needle valve, or the like.

What is claimed is:

1. An apparatus, comprising:
a tray assembly including
- a tray having a first transparent portion and a second transparent portion;
- a first container including a transparent portion, the first container coupled to the tray such that the transparent portion of the first container is aligned with the first transparent portion of the tray;
- a second container including a transparent portion, the second container coupled to the tray such that the transparent portion of the second container is aligned with the second transparent portion of the tray; and
- a valve coupled to the tray, to the first container and to the second container, the valve having a plurality of selectable ports;

the tray assembly configured to be removably coupled to a housing of an instrument with the first container, the second container and the valve coupled to the tray and
a cell counting chip coupled to the tray prior to the tray assembly being coupled to the housing of the instrument, the cell counting chip being a separate container from the first container and the second container, the cell counting chip configured to receive a portion of a fluid mixture from the first container, the portion of a fluid mixture being used to determine a cell count of a sample material within the first container.

2. The apparatus of claim 1, wherein the first transparent portion of the tray and the second transparent portion of the tray each include one of an opening defined by the tray or a transparent material.

3. The apparatus of claim 1, wherein:
the tray includes a third transparent portion, the cell counting chip includes a transparent window aligned with the third transparent portion of the tray.

4. The apparatus of claim 1, wherein the valve is configured to engage a valve actuator of the instrument when the tray assembly is coupled to the housing of the instrument.

5. The apparatus of claim 4, wherein the valve is removably coupled to the tray and configured to be removably coupled to the valve actuator of the instrument when removed from the tray.

6. The apparatus of claim 1, wherein the valve is configured to be coupled to a fluid pump.

7. The apparatus of claim 6, wherein the fluid pump is coupled to the tray prior to the tray assembly being coupled to the housing of the instrument.

8. The apparatus of claim 1, wherein the first container is a first cell culture container configured to receive a cell sample therein, the second container is one of a second cell culture container, a waste container, a reagent container, and a cell harvest container.

9. The apparatus of claim 1, wherein:
the tray assembly further includes at least one of a waste container or a reagent container coupled to the valve.

10. An apparatus, comprising:
a tray assembly including
- a tray having a first transparent portion and a second transparent portion;
- a first container including a transparent portion, the first container coupled to the tray such that the transparent portion of the first container is aligned with the first transparent portion of the tray;
- a second container including a transparent portion, the second container coupled to the tray such that the transparent portion of the second container is aligned with the second transparent portion of the tray; and
- a valve removably coupled to the tray and fluidically coupled to the first container and to the second container, the valve having a plurality of selectable ports;

the tray assembly configured to be removably coupled to a housing of an instrument with the first container, the second container and the valve coupled to the tray,
the valve configured to be removably coupled to a valve actuator of the instrument when removed from the tray while remaining fluidically coupled to the first container and the second container.

11. The apparatus of claim 10, wherein:
the tray assembly further includes a cell counting chip coupled to the tray prior to the tray assembly being coupled to the housing of the instrument, the cell counting chip configured to receive a portion of a fluid mixture from the first container.

12. The apparatus of claim 11, wherein:
the tray includes a third transparent portion, the cell counting chip includes a transparent window aligned with the third transparent portion of the tray.

13. The apparatus of claim 10, wherein the valve is configured to be coupled to a fluid pump.

14. The apparatus of claim 13, wherein the fluid pump is coupled to the tray prior to the tray assembly being coupled to the housing of the instrument.

* * * * *

UNITED STATES PATENT AND TRADEMARK OFFICE
CERTIFICATE OF CORRECTION

PATENT NO. : 12,221,600 B2
APPLICATION NO. : 17/238644
DATED : February 11, 2025
INVENTOR(S) : Ali Afshar et al.

Page 1 of 1

It is certified that error appears in the above-identified patent and that said Letters Patent is hereby corrected as shown below:

In the Specification

Column 38, Line 37, "coupler 2003" should be --coupler 2003'--

Column 38, Line 39, "couplers 2003" should be --couplers 2003'--

Column 40, Line 39, "2107" should be --2107'--

Column 41, Line 54, "2207, 2207, 2207'"" should be --2207, 2207', 2207"--

Column 41, Line 56, "2213, 2213, 2213'"" should be --2213, 2213', 2213"--

Column 41, Line 59, "2202, 2202", 2202'"" should be --2202, 2202', 2202"--

Column 41, Line 61, "2217, 2217, 2217'"" should be --2217, 2217', 2217"--

Column 41, Line 65, "2248, 2248, 2248'"" should be --2248, 2248', 2248"--

Column 42, Line 34, "(and 2247, 2247")" should be --(and 2247', 2247")--

Column 42, Line 35, "2248, 2248'"" should be --2248', 2248"--

Column 43, Line 31, "(2207, 2207")" should be --(2207', 2207")--

Column 43, Line 45, "(2201, 2201")" should be --(2201', 2201")--

Column 43, Line 53, "(2222, 2222")" should be --(2222', 2222")--

Column 44, Line 18, "2207, 2207, 2207'"" should be --2207, 2207', 2207"--

Signed and Sealed this
Sixteenth Day of September, 2025

Coke Morgan Stewart
*Acting Director of the United States Patent and Trademark Office*